(12) United States Patent
Thompson

(10) Patent No.: US 10,988,543 B2
(45) Date of Patent: Apr. 27, 2021

(54) HUMANIZED ANTI-TUMOR NECROSIS FACTOR ALPHA RECEPTOR 2 (ANTI-TNFR2) ANTIBODIES AND METHODS OF USE THEREOF TO ELICIT AN IMMUNE RESPONSE AGAINST A TUMOR

(71) Applicant: OPI VI—IP HoldCo LLC, New York, NY (US)

(72) Inventor: Peter Armstrong Thompson, Bellevue, WA (US)

(73) Assignee: OPI VI—IP HOLDCO LLC, New York, NY (US)

( * ) Notice: Subject to any disclaimer, the term of this patent is extended or adjusted under 35 U.S.C. 154(b) by 0 days.

(21) Appl. No.: 15/775,328

(22) PCT Filed: Nov. 10, 2016

(86) PCT No.: PCT/US2016/061343
§ 371 (c)(1),
(2) Date: May 10, 2018

(87) PCT Pub. No.: WO2017/083525
PCT Pub. Date: May 18, 2017

(65) Prior Publication Data
US 2019/0202925 A1    Jul. 4, 2019

Related U.S. Application Data

(60) Provisional application No. 62/254,127, filed on Nov. 11, 2015.

(51) Int. Cl.
*C07K 16/28* (2006.01)

(52) U.S. Cl.
CPC ...... *C07K 16/2878* (2013.01); *C07K 2317/21* (2013.01); *C07K 2317/24* (2013.01); *C07K 2317/33* (2013.01); *C07K 2317/71* (2013.01); *C07K 2317/74* (2013.01); *C07K 2317/76* (2013.01); *C07K 2317/92* (2013.01)

(58) Field of Classification Search
CPC ............ C07K 16/2878; C07K 2317/21; C07K 2317/24; C07K 2317/33; C07K 2317/71; C07K 2317/74; C07K 2317/76; C07K 2317/92
See application file for complete search history.

(56) References Cited

U.S. PATENT DOCUMENTS

| | | | |
|---|---|---|---|
| 5,582,998 A | 12/1996 | Adolf | |
| 5,730,975 A | 3/1998 | Hotamisligil et al. | |
| 6,015,558 A | 1/2000 | Hotamisligil et al. | |
| 6,054,297 A | 4/2000 | Carter et al. | |
| 6,171,586 B1 | 1/2001 | Lam et al. | |
| 6,232,446 B1 | 5/2001 | Wallach et al. | |
| 6,262,239 B1 | 7/2001 | Wallach et al. | |
| 6,267,958 B1 | 7/2001 | Andya et al. | |
| 6,677,436 B1 | 1/2004 | Sato et al. | |
| 6,913,756 B1 | 7/2005 | Kearney | |
| 7,057,022 B2 | 6/2006 | Smith et al. | |
| 7,527,791 B2 | 5/2009 | Adams et al. | |
| 7,727,528 B2 | 6/2010 | Adcock et al. | |
| 9,081,017 B2 | 7/2015 | Bradley et al. | |
| 9,663,587 B2 | 5/2017 | Hsieh et al. | |
| 9,669,093 B2 | 6/2017 | Medich et al. | |
| 9,670,276 B2 | 6/2017 | Lacy et al. | |
| 9,725,507 B2 | 8/2017 | Song | |
| 9,738,714 B2 | 8/2017 | Krause et al. | |
| 9,750,808 B2 | 9/2017 | Krause et al. | |
| 9,803,009 B2 | 10/2017 | Hsieh et al. | |
| 9,821,010 B2* | 11/2017 | Faustman | A61K 35/17 |
| 2004/0161858 A1 | 8/2004 | Wallach et al. | |
| 2004/0180817 A1 | 9/2004 | Sibson et al. | |
| 2005/0244371 A1 | 11/2005 | Lentz | |
| 2006/0039857 A1 | 2/2006 | Adcock et al. | |
| 2008/0019909 A1 | 1/2008 | Chan et al. | |
| 2008/0176796 A1 | 7/2008 | Bradley et al. | |
| 2010/0034808 A1 | 2/2010 | Nakazawa | |
| 2010/0297012 A1 | 11/2010 | Pfeifer et al. | |
| 2011/0171218 A1* | 7/2011 | Seehra | C07K 14/7151 424/134.1 |
| 2013/0251672 A1 | 9/2013 | Lentz | |
| 2016/0200833 A1 | 7/2016 | Amann et al. | |
| 2016/0340399 A1 | 11/2016 | Amann et al. | |
| 2017/0145087 A1 | 5/2017 | Krause et al. | |
| 2017/0145104 A1 | 5/2017 | Wang et al. | |
| 2017/0151329 A1 | 6/2017 | Krause et al. | |
| 2017/0158759 A1 | 6/2017 | Krause et al. | |
| 2017/0158771 A1 | 6/2017 | Glennie et al. | |
| 2017/0165335 A1 | 6/2017 | Weinschenk et al. | |

(Continued)

FOREIGN PATENT DOCUMENTS

EP    0398327 B1    3/1995
EP    0334165 B1    12/1995
(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
EP16865005.9 Extended European Search Report dated Mar. 15, 2019.
BD Pharmingen Technical Data Sheet Purified Rat Anti-Human CD120b. Dickinson and Company 2007. 2 Pages.
"Chang et al. Blockade of TNF-a signaling benefits cancer therapy by suppressing effector regulatory T cell expansion, OncoImmunology, Oct. 5, 2015, 4:10, e104021, 12 pages".

(Continued)

*Primary Examiner* — Robert S Landsman
(74) *Attorney, Agent, or Firm* — Seed IP Law Group LLP

(57) ABSTRACT

The composition of anti-TNFR2 antibodies are provided, as well as methods of their preparation and use. This includes methods for treating disorders associated with TNF and/or TNFR2, such as cancer.

17 Claims, 20 Drawing Sheets

Specification includes a Sequence Listing.

(56) References Cited

U.S. PATENT DOCUMENTS

| | | |
|---|---|---|
| 2017/0165337 A1 | 6/2017 | Mahr et al. |
| 2017/0166633 A1 | 6/2017 | Mueller et al. |
| 2017/0210795 A1 | 7/2017 | Medich et al. |
| 2017/0247463 A1 | 8/2017 | Ravetch et al. |
| 2017/0247467 A1 | 8/2017 | Amann et al. |
| 2018/0021407 A1 | 1/2018 | Gurney |

FOREIGN PATENT DOCUMENTS

| | | |
|---|---|---|
| EP | 0866131 A2 | 9/1998 |
| EP | 0866131 A3 | 12/1999 |
| EP | 0846169 B1 | 3/2003 |
| EP | 1227843 B1 | 10/2009 |
| EP | 1875247 B1 | 2/2011 |
| EP | 3190124 A1 | 7/2017 |
| EP | 3235509 A1 | 10/2017 |
| WO | WO-9409137 A1 | 4/1994 |
| WO | WO-0121837 A1 | 3/2001 |
| WO | WO-2006044908 A2 | 4/2006 |
| WO | WO-2006074370 A2 | 7/2006 |
| WO | WO-2007049043 A2 | 5/2007 |
| WO | WO-2008051306 A1 | 5/2008 |
| WO | WO-2014124134 A1 | 8/2014 |
| WO | WO-2016156291 A1 | 10/2016 |
| WO | WO-2016187068 A1 | 11/2016 |
| WO | WO-2017060144 A1 | 4/2017 |
| WO | WO-2017089894 A1 | 6/2017 |
| WO | WO-2017089895 A1 | 6/2017 |
| WO | WO-2017097602 A1 | 6/2017 |
| WO | WO-2017097699 A1 | 6/2017 |

OTHER PUBLICATIONS

Co et al. "Humanized antibodies for antiviral therapy", Proc. Natl.Acad. Sci. USA 88, (1992): 2869-2873.

Co, M.S. et al., "Chimeric and Humanized antibodies with specificity for the CD33 antigen," The Journal Immunology 148, (1992): 1149-1154.

Graziewicz, et al., An Endogenous TNF-a Antagonist Induced by Splice-switching Oligonucleotides Reduces Inflammation in Hepatitis and Arthritis Mouse Models. Molecular Therapy, Jul. 2008; 16(7):1316-1322.

Hsiao, et al. Peptides identify multiple hotspots within the ligand binding domain of the TNF receptor 2. Proteome science 1.1 (Jan. 2003): 1-10.

Jones et al. Replacing the complementarity-determining regions in a human antibody with those from a mouse. Nature, 321.6069 (1986): 522-5.

Loosbroock, et al. Inhibiting TNF-α signaling does not attenuate induction of endotoxin tolerance. Journal of inflammation research 7 (2014): 159-167.

LSBIO Anti-TNFRSF1B / TNFR2 Antibody (clone utr 1) LS-C96329. Requested date Sep. 22, 2015. 1 Page.

PCT/US2016/061343 International Search Report and Written Opinion dated Mar. 17, 2017.

Queen C., et al., "A humanized antibody that binds to the interleukin 2 receptor," Dec. 1989, Proceedings of the National Academy of Sciences, National Academy of Sciences, vol. 86, No. 24, pp. 10029-10033, XP002614478.

R&D Systems Human TNF RII/TNFRSF1B Antibody datasheet Clone 2210 Rev. Oct. 31, 2015. 2 Pages.

R&D Systems Human TNF RII/TNFRSF1B Antibody datasheet Clone 2221 Rev. Jul. 2, 2018, 2 Pages.

Riechmann et al. Reshaping human antibodies for therapy. Nature, 332.6162 (1988): 323-7.

Shalaby, et al. Binding and regulation of cellular functions by monoclonal antibodies against human tumor necrosis factor receptors. Journal of Experimental Medicine 172.5 (Nov. 1990): 1517-1520.

Tan et al. "Superhumanized" antibodies: reduction of immunogenic potential by complementarity-determining region grafting with human germline sequences: application to an anti-CD28. J Immunol 169:1119-1125 (2002).

Verhoeyen et al. Reshaping human antibodies: Grafting an antilysozyme activity. Science 239:1534-1536, 1988.

Ware, et al. Tumor necrosis factor (TNF) receptor expression in T lymphocytes. Differential regulation of the type I TNF receptor during activation of resting and effector T cells. The Journal of Immunology 147.12 (Dec. 1991): 4229-4238.

\* cited by examiner

US 10,988,543 B2

HUMANIZED ANTI-TUMOR NECROSIS FACTOR ALPHA RECEPTOR 2 (ANTI-TNFR2) ANTIBODIES AND METHODS OF USE THEREOF TO ELICIT AN IMMUNE RESPONSE AGAINST A TUMOR

CROSS REFERENCE

This Application is a U.S. National Phase Application under 35 U.S.C. § 371 of International Application No. PCT/US2016/061343 filed Nov. 10, 2016, which claims the benefit of U.S. Provisional Application No. 62/254,127 filed Nov. 11, 2015, which are incorporated herein by reference in their entireties.

SEQUENCE LISTING

The instant application contains a Sequence Listing which has been filed electronically in ASCII format and is hereby incorporated by reference in its entirety. Said ASCII copy, created on Nov. 28, 2016, is named 50358-703_601_SL.txt and is 28,882 bytes in size.

BACKGROUND OF THE INVENTION

One main cause of death in the United States is cancer, which can involve an inflammatory immune response. The various response organs, such as the gut, skin, lungs, bone marrow, thymus, and spleen can react with the production of special messenger substances that can activate or cause proliferation of macrophages, T cells, B cells and NK cells, which can have specific functions to protect the body from both foreign invasion and uncontrolled growth of the body's own cells. Some of these messenger substances can include cytokines such as TNFα, C-reactive protein, lymphotoxins, and leukotrienes. TNFα, for example, can act through interaction with TNFα Receptor 1 (TNFR1) and TNFα Receptor 2 (TNFR2). The activity of TNFα through TNFR1 and TNFR2 has been shown to be important in various diseases, including cancer.

INCORPORATION BY REFERENCE

Each patent, publication, and non-patent literature cited in the application is hereby incorporated by reference in its entirety as if each was incorporated by reference individually.

SUMMARY OF THE INVENTION

Provided herein is a brief summary. This summary can be used to provide an understanding of embodiments provided herein, but the embodiments are not limited to what is provided in this summary.

In some embodiments, a composition is a pharmacological composition comprising an antibody that binds to TNFR2 and blocks TNFα binding to TNFR2, wherein said antibody is a humanized antibody.

In other embodiments, a composition is a pharmacological composition comprising an antibody that binds to TNFR2 and blocks TNFα binding to TNFR2, wherein said antibody is a chimeric antibody.

The pharmacological composition of any one of the preceding embodiments, wherein the antibody is an antagonist of TNFR2. The pharmacological composition of any one of the preceding embodiments, wherein said antibody binds to soluble TNFR2 or membrane-bound TNFR2. The pharmacological composition of any one of the preceding embodiments, wherein said TNFR2 is human TNFR2. The pharmacological composition of any one of the preceding embodiments, wherein said antibody binds to cynomolgus monkey TNFR2. The pharmacological composition of any one of the preceding embodiments, wherein said antibody has a dissociation constant ($K_d$) for TNFR2 that is less than 10 nM $K_d$. The pharmacological composition of any one of the preceding embodiments, wherein said antibody has a dissociation constant ($K_d$) for TNFR2 that is less than 100 nM, 75 nM, 50 nM, 30 nM, 20 nM, 10 nM, 5 nM or 1 nM $K_d$. The pharmacological composition of any one of the preceding embodiments, wherein said antibody comprises a human IgG1 Fc domain. In some aspects, said human IgG1 Fc domain is null for binding to an Fcγ receptor. In some aspects, said human IgG1 Fc domain is null for binding to one or more Fcγ receptors. The pharmacological composition of any one of the preceding embodiments, wherein said TNFα is human TNFα. The pharmacological composition of any one of the preceding embodiments, wherein said antibody is purified. The pharmacological composition of any one of the preceding embodiments, wherein said antibody inhibits death of Jurkat cells expressing TNFR2 when cultured with TNFα. The pharmacological composition of any one of the preceding embodiments, wherein said antibody suppresses expansion of a regulatory T cells. The pharmacological composition of any one of the preceding embodiments, wherein said antibody decreases regulatory T cell immunosuppression. The pharmacological composition of any one of the preceding embodiments, wherein said antibody reverses suppression caused by myeloid-derived suppressor cells.

The pharmacological composition of any one of the preceding embodiments, wherein said antibody comprises: a) HCDR1 comprising an amino acid sequence of SEQ ID NO: 10; b) HCDR2 comprising an amino acid sequence of SEQ ID NO: 11; and c) HCDR3 comprising an amino acid sequence of SEQ ID NO: 12. In some aspects, said antibody further comprises: d) LCDR1 comprising an amino acid sequence of SEQ ID NO: 13; e) LCDR2 comprising an amino acid sequence of SEQ ID NO: 14; and f) LCDR3 comprising an amino acid sequence of SEQ ID NO: 15.

The pharmacological composition of any one of the preceding embodiments, wherein said antibody comprises: a) HCDR1 comprising an amino acid sequence of SEQ ID NO: 16; b) HCDR2 comprising an amino acid sequence of SEQ ID NO: 17; and c) HCDR3 comprising an amino acid sequence of SEQ ID NO: 18. In some aspects, said antibody further comprises: d) LCDR1 comprising an amino acid sequence of SEQ ID NO: 19; e) LCDR2 comprising an amino acid sequence of SEQ ID NO: 20; and f) LCDR3 comprising an amino acid sequence of SEQ ID NO: 21.

The pharmacological composition of any one of the preceding embodiments, wherein said antibody comprises: a) HCDR1 comprising an amino acid sequence of SEQ ID NO: 22; b) HCDR2 comprising an amino acid sequence of SEQ ID NO: 23; and c) HCDR3 comprising an amino acid sequence of SEQ ID NO: 24. In some aspects, said antibody further comprises: d) LCDR1 comprising an amino acid sequence of SEQ ID NO: 25; e) LCDR2 comprising an amino acid sequence of SEQ ID NO: 26; and f) LCDR3 comprising an amino acid sequence of SEQ ID NO: 27.

The pharmacological composition of any one of the preceding embodiments, wherein said antibody comprises: a) HCDR1 comprising an amino acid sequence of SEQ ID NO: 28; b) HCDR2 comprising an amino acid sequence of SEQ ID NO: 29; and c) HCDR3 comprising an amino acid sequence of SEQ ID NO: 30. In some aspects, said antibody further comprises: d) LCDR1 comprising an amino acid sequence of SEQ ID NO: 31; e) LCDR2 comprising an amino acid sequence of SEQ ID NO: 32; and f) LCDR3 comprising an amino acid sequence of SEQ ID NO: 33.

The pharmacological composition of any one of the preceding embodiments, wherein said antibody comprises: a) HCDR1 comprising an amino acid sequence of SEQ ID NO: 34; b) HCDR2 comprising an amino acid sequence of SEQ ID NO: 35; and c) HCDR3 comprising an amino acid sequence of SEQ ID NO: 36. In some aspects, said antibody further comprises: d) LCDR1 comprising an amino acid sequence of SEQ ID NO: 37; e) LCDR2 comprising an amino acid sequence of SEQ ID NO: 38; and f) LCDR3 comprising an amino acid sequence of SEQ ID NO: 39.

The pharmacological composition of any one of the preceding embodiments, wherein said antibody comprises: a) HCDR1 comprising an amino acid sequence of SEQ ID NO: 40; b) HCDR2 comprising an amino acid sequence of SEQ ID NO: 41; and c) HCDR3 comprising an amino acid sequence of SEQ ID NO: 42. In some aspects, said antibody further comprises: d) LCDR1 comprising an amino acid sequence of SEQ ID NO: 43; e) LCDR2 comprising an amino acid sequence of SEQ ID NO: 44; and f) LCDR3 comprising an amino acid sequence of SEQ ID NO: 45.

The pharmacological composition of any one of the preceding embodiments, wherein said antibody comprises: a) HCDR1 comprising an amino acid sequence of SEQ ID NO: 46; b) HCDR2 comprising an amino acid sequence of SEQ ID NO: 47; and c) HCDR3 comprising an amino acid sequence of SEQ ID NO: 48. In some aspects, said antibody further comprises: d) LCDR1 comprising an amino acid sequence of SEQ ID NO: 49; e) LCDR2 comprising an amino acid sequence of SEQ ID NO: 50; and f) LCDR3 comprising an amino acid sequence of SEQ ID NO: 51. In some aspects, said antibody further comprises: d) LCDR1 comprising an amino acid sequence of SEQ ID NO: 52; e) LCDR2 comprising an amino acid sequence of SEQ ID NO: 53; and f) LCDR3 comprising an amino acid sequence of SEQ ID NO: 54.

The pharmacological composition of any one of the preceding embodiments, wherein said antibody comprises: a) HCDR1 comprising an amino acid sequence of SEQ ID NO: 55; b) HCDR2 comprising an amino acid sequence of SEQ ID NO: 56; and c) HCDR3 comprising an amino acid sequence of SEQ ID NO: 57. In some aspects, said antibody further comprises: d) LCDR1 comprising an amino acid sequence of SEQ ID NO: 58; e) LCDR2 comprising an amino acid sequence of SEQ ID NO: 59; and f) LCDR3 comprising an amino acid sequence of SEQ ID NO: 60. In some aspects, said antibody further comprises: d) LCDR1 comprising an amino acid sequence of SEQ ID NO: 61; e) LCDR2 comprising an amino acid sequence of SEQ ID NO: 62; and f) LCDR3 comprising an amino acid sequence of SEQ ID NO: 63.

The pharmacological composition of any one of the preceding embodiments, wherein said antibody comprises: a) HCDR1 comprising an amino acid sequence of SEQ ID NO: 10; b) HCDR2 comprising an amino acid sequence of SEQ ID NO: 11; c) HCDR3 comprising an amino acid sequence of SEQ ID NO: 12; d) LCDR1 comprising an amino acid sequence of SEQ ID NO: 13; e) LCDR2 comprising an amino acid sequence of SEQ ID NO: 14; and f) LCDR3 comprising an amino acid sequence of SEQ ID NO: 15.

The pharmacological composition of any one of the preceding embodiments, wherein said antibody comprises: a) HCDR1 comprising an amino acid sequence of SEQ ID NO: 16; b) HCDR2 comprising an amino acid sequence of SEQ ID NO: 17; c) HCDR3 comprising an amino acid sequence of SEQ ID NO: 18; d) LCDR1 comprising an amino acid sequence of SEQ ID NO: 19; e) LCDR2 comprising an amino acid sequence of SEQ ID NO: 20; and f) LCDR3 comprising an amino acid sequence of SEQ ID NO: 21.

The pharmacological composition of any one of the preceding embodiments, wherein said antibody comprises: a) HCDR1 comprising an amino acid sequence of SEQ ID NO: 22; b) HCDR2 comprising an amino acid sequence of SEQ ID NO: 23; c) HCDR3 comprising an amino acid sequence of SEQ ID NO: 24; d) LCDR1 comprising an amino acid sequence of SEQ ID NO: 25; e) LCDR2 comprising an amino acid sequence of SEQ ID NO: 26; and f) LCDR3 comprising an amino acid sequence of SEQ ID NO: 27.

The pharmacological composition of any one of the preceding embodiments, wherein said antibody comprises: a) HCDR1 comprising an amino acid sequence of SEQ ID NO: 28; b) HCDR2 comprising an amino acid sequence of SEQ ID NO: 29; c) HCDR3 comprising an amino acid sequence of SEQ ID NO: 30; d) LCDR1 comprising an amino acid sequence of SEQ ID NO: 31; e) LCDR2 comprising an amino acid sequence of SEQ ID NO: 32; and f) LCDR3 comprising an amino acid sequence of SEQ ID NO: 33.

The pharmacological composition of any one of the preceding embodiments, wherein said antibody comprises: a) HCDR1 comprising an amino acid sequence of SEQ ID NO: 34; b) HCDR2 comprising an amino acid sequence of SEQ ID NO: 35; c) HCDR3 comprising an amino acid sequence of SEQ ID NO: 36; d) LCDR1 comprising an amino acid sequence of SEQ ID NO: 37; e) LCDR2 comprising an amino acid sequence of SEQ ID NO: 38; and f) LCDR3 comprising an amino acid sequence of SEQ ID NO: 39.

The pharmacological composition of any one of the preceding embodiments, wherein said antibody comprises: a) HCDR1 comprising an amino acid sequence of SEQ ID NO: 40; b) HCDR2 comprising an amino acid sequence of SEQ ID NO: 41; c) HCDR3 comprising an amino acid sequence of SEQ ID NO: 42; d) LCDR1 comprising an amino acid sequence of SEQ ID NO: 43; e) LCDR2 comprising an amino acid sequence of SEQ ID NO: 44; and f) LCDR3 comprising an amino acid sequence of SEQ ID NO: 45.

The pharmacological composition of any one of the preceding embodiments, wherein said antibody comprises: a) HCDR1 comprising an amino acid sequence of SEQ ID NO: 46; b) HCDR2 comprising an amino acid sequence of SEQ ID NO: 47; c) HCDR3 comprising an amino acid sequence of SEQ ID NO: 48; d) LCDR1 comprising an amino acid sequence of SEQ ID NO: 49; e) LCDR2 comprising an amino acid sequence of SEQ ID NO: 50; and f) LCDR3 comprising an amino acid sequence of SEQ ID NO: 51.

The pharmacological composition of any one of the preceding embodiments, wherein said antibody comprises: a) HCDR1 comprising an amino acid sequence of SEQ ID NO: 46; b) HCDR2 comprising an amino acid sequence of SEQ ID NO: 47; c) HCDR3 comprising an amino acid sequence of SEQ ID NO: 48; d) LCDR1 comprising an amino acid sequence of SEQ ID NO: 52; e) LCDR2 comprising an amino acid sequence of SEQ ID NO: 53; and f) LCDR3 comprising an amino acid sequence of SEQ ID NO: 54.

The pharmacological composition of any one of the preceding embodiments, wherein said antibody comprises: a) HCDR1 comprising an amino acid sequence of SEQ ID NO: 55; b) HCDR2 comprising an amino acid sequence of SEQ ID NO: 56; c) HCDR3 comprising an amino acid sequence of SEQ ID NO: 57; d) LCDR1 comprising an amino acid sequence of SEQ ID NO: 58; e) LCDR2 comprising an amino acid sequence of SEQ ID NO: 59; and f) LCDR3 comprising an amino acid sequence of SEQ ID NO: 60.

The pharmacological composition of any one of the preceding embodiments, wherein said antibody comprises: a) HDCDR1 comprising an amino acid sequence of SEQ ID NO: 55; b) HCDR2 comprising an amino acid sequence of SEQ ID NO: 56; c) HCDR3 comprising an amino acid sequence of SEQ ID NO: 57; d) LCDR1 comprising an amino acid sequence of SEQ ID NO: 61; e) LCDR2 comprising an amino acid sequence of SEQ ID NO: 62; and f) LCDR3 comprising an amino acid sequence of SEQ ID NO: 63.

The pharmacological composition of any one of the preceding embodiments, wherein said antibody comprises at least 80% sequence identity to a) HCDR1 comprising an amino acid sequence of SEQ ID NO: 10; b) HCDR2 comprising an amino acid sequence of SEQ ID NO: 11; c) HCDR3 comprising an amino acid sequence of SEQ ID NO: 12; d) LCDR1 comprising an amino acid sequence of SEQ ID NO: 13; e) LCDR2 comprising an amino acid sequence of SEQ ID NO: 14; and f) LCDR3 comprising an amino acid sequence of SEQ ID NO: 15.

The pharmacological composition of any one of the preceding embodiments, wherein said antibody comprises at least 80% sequence identity to: a) HCDR1 comprising an amino acid sequence of SEQ ID NO: 16; b) HCDR2 comprising an amino acid sequence of SEQ ID NO: 17; c) HCDR3 comprising an amino acid sequence of SEQ ID NO: 18; d) LCDR1 comprising an amino acid sequence of SEQ ID NO: 19; e) LCDR2 comprising an amino acid sequence of SEQ ID NO: 20; and f) LCDR3 comprising an amino acid sequence of SEQ ID NO: 21.

The pharmacological composition of any one of the preceding embodiments, wherein said antibody comprises at least 80% sequence identity to: a) HCDR1 comprising an amino acid sequence of SEQ ID NO: 22; b) HCDR2 comprising an amino acid sequence of SEQ ID NO: 23; c) HCDR3 comprising an amino acid sequence of SEQ ID NO: 24; d) LCDR1 comprising an amino acid sequence of SEQ ID NO: 25; e) LCDR2 comprising an amino acid sequence of SEQ ID NO: 26; and f) LCDR3 comprising an amino acid sequence of SEQ ID NO: 27.

The pharmacological composition of any one of the preceding embodiments, wherein said antibody comprises at least 80% sequence identity to: a) HCDR1 comprising an amino acid sequence of SEQ ID NO: 28; b) HCDR2 comprising an amino acid sequence of SEQ ID NO: 29; c) HCDR3 comprising an amino acid sequence of SEQ ID NO: 30; d) LCDR1 comprising an amino acid sequence of SEQ ID NO: 31; e) LCDR2 comprising an amino acid sequence of SEQ ID NO: 32; and f) LCDR3 comprising an amino acid sequence of SEQ ID NO: 33.

The pharmacological composition of any one of the preceding embodiments, wherein said antibody comprises at least 80% sequence identity to: a) HCDR1 comprising the amino acid sequence of SEQ ID NO: 34; b) HCDR2 comprising an amino acid sequence of SEQ ID NO: 35; c) HCDR3 comprising an amino acid sequence of SEQ ID NO: 36; d) LCDR1 comprising an amino acid sequence of SEQ ID NO: 37; e) LCDR2 comprising an amino acid sequence of SEQ ID NO: 38; and f) LCDR3 comprising an amino acid sequence of SEQ ID NO: 39.

The pharmacological composition of any one of the preceding embodiments, wherein said antibody comprises at least 80% sequence identity to: a) HCDR1 comprising an amino acid sequence of SEQ ID NO: 40; b) HCDR2 comprising an amino acid sequence of SEQ ID NO: 41; c) HCDR3 comprising an amino acid sequence of SEQ ID NO: 42; d) LCDR1 comprising an amino acid sequence of SEQ ID NO: 43; e) LCDR2 comprising an amino acid sequence of SEQ ID NO: 44; and f) LCDR3 comprising an amino acid sequence of SEQ ID NO: 45.

The pharmacological composition of any one of the preceding embodiments, wherein said antibody comprises at least 80% sequence identity to: a) HCDR1 comprising an amino acid sequence of SEQ ID NO: 46; b) HCDR2 comprising an amino acid sequence of SEQ ID NO: 47; c) HCDR3 comprising an amino acid sequence of SEQ ID NO: 48; d) LCDR1 comprising an amino acid sequence of SEQ ID NO: 49; e) LCDR2 comprising an amino acid sequence of SEQ ID NO: 50; and f) LCDR3 comprising an amino acid sequence of SEQ ID NO: 51.

The pharmacological composition of any one of the preceding embodiments, wherein said antibody comprises at least 80% sequence identity to: a) HCDR1 comprising an amino acid sequence of SEQ ID NO: 46; b) HCDR2 comprising an amino acid sequence of SEQ ID NO: 47; c) HCDR3 comprising an amino acid sequence of SEQ ID NO: 48; d) LCDR1 comprising an amino acid sequence of SEQ ID NO: 52; e) LCDR2 comprising an amino acid sequence of SEQ ID NO: 53; and f) LCDR3 comprising an amino acid sequence of SEQ ID NO: 54.

The pharmacological composition of any one of the preceding embodiments, wherein said antibody comprises at least 80% sequence identity to: a) HCDR1 comprising an amino acid sequence of SEQ ID NO: 55; b) HCDR2 comprising an amino acid sequence of SEQ ID NO: 56; c) HCDR3 comprising an amino acid sequence of SEQ ID NO: 57; d) LCDR1 comprising an amino acid sequence of SEQ ID NO: 58; e) LCDR2 comprising an amino acid sequence of SEQ ID NO: 59; and f) LCDR3 comprising an amino acid sequence of SEQ ID NO: 60.

The pharmacological composition of any one of the preceding embodiments, wherein said antibody comprises at least 80% sequence identity to: a) HCDR1 comprising an amino acid sequence of SEQ ID NO: 55; b) HCDR2 comprising an amino acid sequence of SEQ ID NO: 56; c) HCDR3 comprising an amino acid sequence of SEQ ID NO: 57; d) LCDR1 comprising an amino acid sequence of SEQ ID NO: 61; e) LCDR2 comprising an amino acid sequence of SEQ ID NO: 62; and f) LCDR3 comprising an amino acid sequence of SEQ ID NO: 63.

The pharmacological composition of any one of the preceding embodiments, wherein said antibody comprises at least 80% sequence identity to 6 contiguous amino acids between amino acid 20 and amino acid 110 of SEQ ID NO: 1. In some aspects, said antibody further comprises at least 80% sequence identity to 6 contiguous amino acids between amino acid 20 and amino acid 100 of SEQ ID NO: 2.

The pharmacological composition of any one of the preceding embodiments, wherein said antibody comprises at least 80% sequence identity to 6 contiguous amino acids between amino acid 20 and amino acid 110 of SEQ ID NO:

3. In some aspects, said antibody further comprises at least 80% sequence identity to 6 contiguous amino acids between amino acid 20 and amino acid 100 of SEQ ID NO: 4.

The pharmacological composition of any one of the preceding embodiments, wherein said antibody comprises at least 80% sequence identity to 6 contiguous amino acids between amino acid 20 and amino acid 110 of SEQ ID NO: 5. In some aspects, said antibody further comprises at least 80% sequence identity to 6 contiguous amino acids between amino acid 20 and amino acid 100 of SEQ ID NO: 6.

The pharmacological composition of any one of the preceding embodiments, wherein said antibody comprises at least 80% sequence identity to 6 contiguous amino acids between amino acid 20 and amino acid 110 of SEQ ID NO: 7. In some aspects, said antibody further comprises at least 80% sequence identity to 6 contiguous amino acids between amino acid 20 and amino acid 100 of SEQ ID NO: 8. In some aspects, said antibody further comprises at least 80% sequence identity to 6 contiguous amino acids between amino acid 20 and amino acid 100 of SEQ ID NO: 9.

The pharmacological composition of any one of the preceding embodiments, comprising a) a $V_H$ sequence having at least 80% sequence identity to an amino acid sequence of SEQ ID NO: 1; and b) a $V_L$ sequence having at least 80% sequence identity to an amino acid sequence of SEQ ID NO: 2.

The pharmacological composition of any one of the preceding embodiments, comprising a) a $V_H$ sequence having at least 90%, 95%, or 98% sequence identity to the amino acid sequence of SEQ ID NO: 1; and b) a $V_L$ sequence having at least 90%, 95%, or 98% sequence identity to the amino acid sequence of SEQ ID NO: 2.

The pharmacological composition of any one of the preceding embodiments, comprising a) a $V_H$ sequence having at least 80% sequence identity to the amino acid sequence of SEQ ID NO: 3; and b) a $V_L$ sequence having at least 80% sequence identity to the amino acid sequence of SEQ ID NO: 4.

The pharmacological composition of any one of the preceding embodiments, comprising a) a $V_H$ sequence having at least 90%, 95%, or 98% sequence identity to the amino acid sequence of SEQ ID NO: 3; and b) a $V_L$ sequence having at least 90%, 95%, or 98% sequence identity to the amino acid sequence of SEQ ID NO: 4.

The pharmacological composition of any one of the preceding embodiments, comprising a) a $V_H$ sequence having at least 80% sequence identity to the amino acid sequence of SEQ ID NO: 5; and b) a $V_L$ sequence having at least 80% sequence identity to the amino acid sequence of SEQ ID NO: 6.

The pharmacological composition of any one of the preceding embodiments, comprising a) a $V_H$ sequence having at least 90%, 95%, or 98% sequence identity to the amino acid sequence of SEQ ID NO: 5; and b) a $V_L$ sequence having at least 90%, 95%, or 98% sequence identity to the amino acid sequence of SEQ ID NO: 6.

The pharmacological composition of any one of the preceding embodiments, comprising a) a $V_H$ sequence having at least 80% sequence identity to the amino acid sequence of SEQ ID NO: 7; and b) a $V_L$ sequence having at least 80% sequence identity to the amino acid sequence of SEQ ID NO: 8.

The pharmacological composition of any one of the preceding embodiments, comprising a) a $V_H$ sequence having at least 90%, 95%, or 98% sequence identity to the amino acid sequence of SEQ ID NO: 7; and b) a $V_L$ sequence having at least 90%, 95%, or 98% sequence identity to the amino acid sequence of SEQ ID NO: 8.

The pharmacological composition of any one of the preceding embodiments, comprising a) a $V_H$ sequence having at least 80% sequence identity to the amino acid sequence of SEQ ID NO: 7; and b) a $V_L$ sequence having at least 80% sequence identity to the amino acid sequence of SEQ ID NO: 9.

The pharmacological composition of any one of the preceding embodiments, comprising a) a $V_H$ sequence having at least 90%, 95%, or 98% sequence identity to the amino acid sequence of SEQ ID NO: 7; and b) a $V_L$ sequence having at least 90%, 95%, or 98% sequence identity to the amino acid sequence of SEQ ID NO: 9.

The pharmacological composition of any one of the preceding embodiments wherein said antibody comprises at least 80% sequence identity to 6 contiguous amino acids from amino acid 1 to amino acid 119 of SEQ ID NO: 64.

The pharmacological composition of any one of the preceding embodiments, wherein said antibody comprises at least 80% sequence identity to 6 contiguous amino acids from amino acid 1 to amino acid 106 of SEQ ID NO: 65.

The pharmacological composition of any one of the preceding embodiments, wherein said antibody comprises at least 80% sequence identity to 6 contiguous amino acids from amino acid 1 to amino acid 119 of SEQ ID NO: 66.

The pharmacological composition o of any one of the preceding embodiments, wherein said antibody comprises at least 80% sequence identity to 6 contiguous amino acids from amino acid 1 to amino acid 106 of SEQ ID NO: 67.

The pharmacological composition of any one of the preceding embodiments, wherein said antibody comprises at least 80% sequence identity to 6 contiguous amino acids from amino acid 1 to amino acid 119 of SEQ ID NO: 68.

The pharmacological composition of any one of the preceding embodiments, wherein said antibody comprises at least 80% sequence identity to 6 contiguous amino acids from amino acid 1 to amino acid 106 of SEQ ID NO: 69.

The pharmacological composition of any one of the preceding embodiments, comprising a) a $V_H$ sequence having at least 80% sequence identity to an amino acid sequence of SEQ ID NO: 64; and b) a $V_L$ sequence having at least 80% sequence identity to an amino acid sequence of SEQ ID NO: 65. The pharmacological composition of any one of the preceding embodiments, comprising a) a $V_H$ sequence having at least 90%, 95%, or 98% sequence identity to the amino acid sequence of SEQ ID NO: 64; and b) a $V_L$ sequence having at least 90%, 95%, or 98% sequence identity to the amino acid sequence of SEQ ID NO: 65.

The pharmacological composition of any one of the preceding embodiments, comprising a) a $V_H$ sequence having at least 80% sequence identity to the amino acid sequence of SEQ ID NO: 66; and b) a $V_L$ sequence having at least 80% sequence identity to the amino acid sequence of SEQ ID NO: 67. The pharmacological composition of any one of the preceding embodiments, comprising a) a $V_H$ sequence having at least 90%, 95%, or 98% sequence identity to the amino acid sequence of SEQ ID NO: 66; and b) a $V_L$ sequence having at least 90%, 95%, or 98% sequence identity to the amino acid sequence of SEQ ID NO: 67.

The pharmacological composition of of any one of the preceding embodiments, comprising a) a $V_H$ sequence having at least 80% sequence identity to the amino acid sequence of SEQ ID NO: 66; and b) a $V_L$ sequence having at least 80% sequence identity to the amino acid sequence of SEQ ID NO: 69. The pharmacological composition of any one of the preceding embodiments, comprising a) a $V_H$ sequence having at least 90%, 95%, or 98% sequence identity to the amino acid sequence of SEQ ID NO: 66; and b) a $V_L$ sequence having at least 90%, 95%, or 98% sequence identity to the amino acid sequence of SEQ ID NO: 69.

The pharmacological composition of any one of the preceding embodiments, comprising a) a $V_H$ sequence having at least 80% sequence identity to the amino acid sequence of SEQ ID NO: 68; and b) a $V_L$ sequence having at least 80% sequence identity to the amino acid sequence of SEQ ID NO: 67. The pharmacological composition of any one of the preceding embodiments, comprising a) a $V_H$ sequence having at least 90%, 95%, or 98% sequence identity to the amino acid sequence of SEQ ID NO: 68; and b) a $V_L$ sequence having at least 90%, 95%, or 98% sequence identity to the amino acid sequence of SEQ ID NO: 67.

The pharmacological composition of any one of the preceding embodiments, comprising a) a $V_H$ sequence having at least 80% sequence identity to the amino acid sequence of SEQ ID NO: 68; and b) a $V_L$ sequence having at least 80% sequence identity to the amino acid sequence of SEQ ID NO: 69. The pharmacological composition of any one of the preceding embodiments, comprising a) a $V_H$ sequence having at least 90%, 95%, or 98% sequence identity to the amino acid sequence of SEQ ID NO: 68; and b) a $V_L$ sequence having at least 90%, 95%, or 98% sequence identity to the amino acid sequence of SEQ ID NO: 69.

An isolated nucleic acid encoding the antibody of any one of the preceding embodiments. A vector comprising the nucleic acid of the preceding embodiment. A host cell comprising the vector of the preceding embodiment. In some aspects, the host cell is a mammalian cell.

A method of producing an antibody comprising culturing the host cell of any of the two preceding embodiments so that the antibody is produced.

An immunoconjugate comprising said antibody of any one of the preceding pharmacological embodiments and a therapeutic agent. A pharmaceutical composition comprising said pharmacological composition of any one of the pharmacological embodiments and a pharmaceutically acceptable carrier.

A method of treatment for a subject in need thereof, comprising administering a therapeutic dose of said antibody of any one of the preceding pharmacological composition embodiments and a pharmaceutical carrier. A method of treatment for a subject in need thereof, comprising administering a therapeutic dose of said pharmacological composition of any one of the preceding pharmacological composition embodiments. In some aspects, the subject has cancer. In some aspects, the cancer is a tumor comprising a ratio of regulatory T cells to effector T cells that is greater than 1:10. In some aspects, the cancer secretes TNFα. In some aspects, the cancer expresses membrane-bound TNFα. In some aspects, the subject has colorectal cancer, hepatocellular cancer, pancreatic cancer, breast cancer, melanoma, ovarian cancer, lung cancer, renal cancer, glioblastoma leukemia, or lymphoma. In some aspects, said pharmacological composition is administered intravenously, cutaneously, subcutaneously, or injected at a site of affliction. A kit comprising a pharmaceutically acceptable dosage unit of a pharmaceutically effective amount of an antibody according to any one of the preceding pharmacological composition embodiments.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
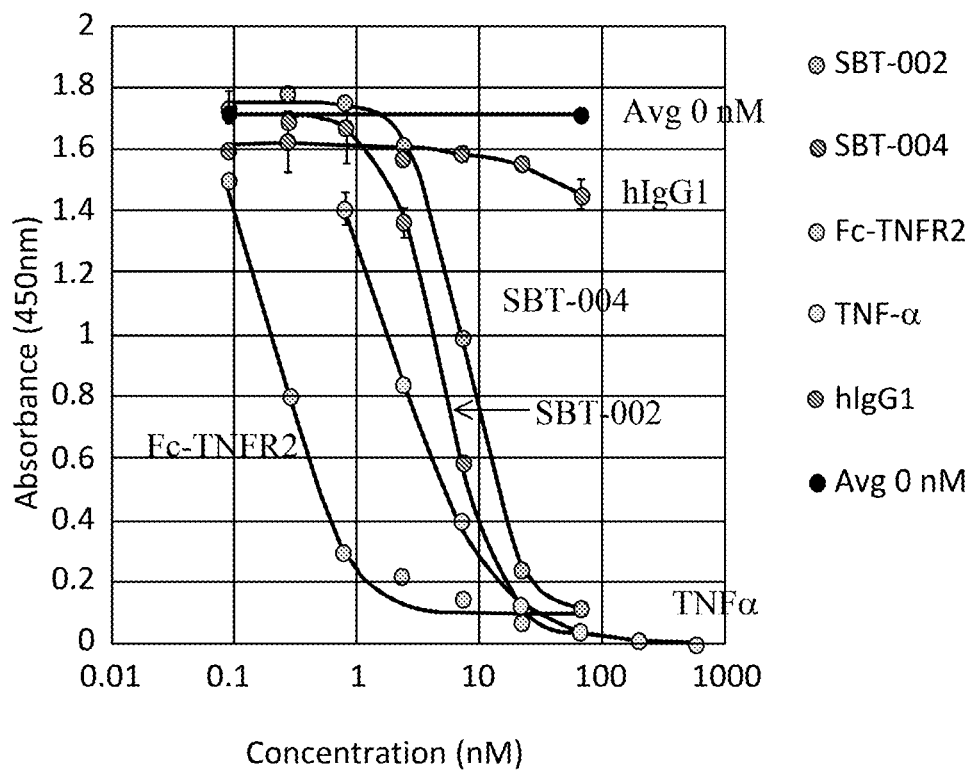
FIG. 1 shows the binding of SBT-002, SBT-004, Fc-TNFR2, TNFα, and hIgG1 to TNFR2. The results indicate that SBT-002 had an $IC_{50}$ of 5.12 nM, SBT-004 had an $IC_{50}$ of 7.88 nM, Fc-TNFR2 had an $IC_{50}$ of 0.23 nM, and TNF-alpha had an $IC_{50}$ of 1.64 nM. The hIgG1 negative control had close to no binding to TNFR2.

Tumor Necrosis Factor (TNFα) is a pleiotropic pro-inflammatory cytokine that can be produced mainly by macrophages and T cells, but can also be expressed by tumor cells. Additionally, TNFα can be produced either as soluble TNFα and/or membrane bound TNFα. The amount of TNFα can be crucial to an immune response; too much can cause cachexia and septic shock, while too little can allow for an infection to progress.

The body's white cells can recognize a cancer cell, bind to the cancer cell if the body's defense systems are not blocked or inhibited, and kill the cancer cell. This reaction can be inhibited by immunosuppressants, either from outside the body, such as by medications, radiation, or environmental toxins, or from within the body, such as by cytokines secreted in the tumor microenvironment. If the inhibitors or blockers of the normal white cell response can be removed, then the immune system can attack and kill the affected cells.

The importance of TNFα in human disease can be highlighted by the efficacy of anti-TNFα antibodies in controlling disease activity in rheumatoid arthritis and other inflammatory conditions. TNFα can interact with two distinct receptors, designated TNFα Receptor 1 (TNFR1) and TNFα Receptor 2 (TNFR2), and understanding the specific role of each receptor in TNFα signaling is important for rational use of TNFα blockade. The signaling events initiated by each TNFα Receptor (TNFR) can vary among cell types in culture.

The cytoplasmic sequences of TNFR1 and TNFR2 can share no homology and both can be devoid of intrinsic enzyme activity. Instead, TNFR1 and TNFR2 can initiate signaling by recruitment of cytosolic proteins through protein-protein interaction domains in their cytoplasmic regions. TNFR1 can signal by recruitment to its death domain of TNFR-associated-death-domain protein (TRADD), which can serve as a supporting structure for recruitment of TNFα-receptor associated factor 2 (TRAF2) and receptor-interacting protein-1 (RIP-1). This signaling complex can lead to activation of transcription factors such as NFκB and AP-1. TNFR2 may not contain a cytoplasmic death domain although it can interact directly with TRAF2, providing a mechanism for some shared activity of TNFRs.

TNFR1 and TNFR2 can differentially activate Apoptosis signaling kinase-1 (ASK1) and endothelial/epithelial tyrosine kinase (Etk). ASK1 is a kinase which can be activated by TNFα through TNFR1 and can activate multiple pro-apoptotic pathways in cultured cells. ASK1 activity can be controlled by several mechanisms, including protein-protein interactions with thioredoxin, the dimeric phosphoserine-binding molecule 14-3-3, and TRAF2. ASK1 activation can be assessed by loss of phosphorylation at Ser 967 coupled with de novo phosphorylation at Thr845.

Etk (i.e., Bmx; bone marrow tyrosine kinase in chromosome X) is a kinase which can be activated by TNFα through TNFR2 and has been implicated in cell adhesion, migration, proliferation, and survival. In epithelial cells, Etk can be a regulator of cell junctions. In vascular endothelial cells (EC), Etk can be involved in TNFα-induced angiogenic events and can mediate activation of the phosphatidylinositol 3 kinase (PI3K)-Atk angiogenic pathway, which can be involved in growth factor stimulated cell migration. The appearance and phosphorylation of Etk in EC can be indicative of TNFR2 signaling.

In conjunction with TNFα, T cells can play a critical role in immune responses. More specifically, regulatory T cells, which are a distinct subpopulation of T cells, can be critical in maintaining peripheral tolerance under normal physiological conditions. They can have the capacity to dominantly suppress the proliferation of CD8+ T cells and inhibit autoimmune disease in vivo, but can also play a role in suppressing anti-tumor responses in cancer. This subpopulation of T cells was originally identified as a CD4+ CD25+ cell population, but were later also characterized by the expression of the forkhead family transcription factor FoxP3. These Foxp3+ CD4+ CD25+ regulatory T cells (Treg cells) can express high levels of cytotoxic T lymphocyte-associated antigen-4 (CTLA-4), OX-40, 4-1BB and glucocorticoid inducible TNF receptor associated protein (GITR). Additionally, Treg cells are among the many different types of cells that express TNFR2.

Tumors can express tumor-associated antigens, which can result in an immune reaction. However, such tumor-associated antigen specific immune responses have not typically been observed. Treg cells have been implicated as major contributors to the ultimate failure of anti-tumor responses in humans. For example, in ovarian cancer, Treg cells can suppress tumor-specific T cells and high numbers of tumor-associated Treg cells can be associated with reduced survival time. Furthermore, an increased number of intratumoral effector T cells in ovarian cancer can be associated with a better prognosis. A similar observation has been made with respect to colorectal cancer. Lung tumors can also be shown to have a high number of Treg cells, and these Treg cells can selectively inhibit the host immune response and may thereby contribute to cancer progression. Treg cells can also be shown to be elevated in tumor samples from glioblastoma mutliforme patients.

Treg cells can also play a role in some viral and parasitic infections. For instance, an overabundance of Treg cells and resultant immune suppression can be detected in retroviral infections. Immune suppression by Treg cells can also be found in *Leishmania* and malaria mouse models. In a filarial-infected mouse model, reduction in the number of Treg cells by antibody therapy can result in a dramatic reduction in parasite numbers.

Treg cells can constitutively express TNFR2. Membrane-bound TNFα expressed by CD8+ T cells can activation of TNFR2 signaling on Treg cells. Activation of TNFR2 signaling can make a Treg more suppressive, and can additionally induce Treg cell proliferation and expansion. Therefore, the loss of TNFR2 or inhibition of TNFR2 function could prevent the accumulation of Treg cells and would make the Tregs less immunosuppressive, resulting in a less tolerogenic environment and thus enabling the immune system to more effectively control tumor metastasis and growth.

I. Anti-TNFR2 Antibody

An anti-TNFR2 antibody can be an antibody that can bind TNFR2. An anti-TNFR2 antibody can be a humanized antibody that can bind TNFR2. An anti-TNFR2 antibody can be a chimeric antibody that can bind TNFR2. An anti-TNFR2 antibody can be a humanized antibody that can bind TNFR2 and can block TNFα binding. An anti-TNFR2 antibody can be a chimeric antibody that can bind TNFR2 and can block TNFα binding. An anti-TNFR2 antibody can be a humanized antibody that can be an antagonist of TNFR2. An anti-TNFR2 antibody can be a humanized antibody that can be an antagonist of TNFR2 activity by TNFα. An anti-TNFR2 antibody can be a chimeric antibody that can be an antagonist of TNFR2. An anti-TNFR2 antibody can be a chimeric antibody that can be an antagonist of TNFR2 activity by TNFα. The TNFα can be human TNFα. The anti-TNFR2 antibody can suppress expansion of regulatory T cells. The anti-TNFR2 antibody can decrease regulatory T cell immunosuppression. The anti-TNFR2 antibody can inhibit death of Jurkat cells expressing TNFR2 when cultured with TNFα.

An antibody molecule can consist of two identical light protein chains and two identical heavy protein chains, which can be held together covalently by disulfide linkages. The N-terminal regions of the light and heavy chains can form the antigen recognition site of an antibody. Structurally, various functions of an antibody can be confined to discrete protein domains (i.e., regions). The sites that can recognize and can bind antigen can consist of three complementarity determining regions (CDRs) that can lie within the variable heavy chain regions and the variable light chain regions at the N-terminal ends of the two heavy and two light chains. The constant domains, which can also be referred to as Fc domains, can provide the general framework of the antibody and may not be involved directly in binding the antibody to an antigen, but can be involved in various effector functions, such as participation of the antibody in antibody-dependent cellular cytotoxicity.

The domains of natural light and heavy chains can have the same general structures, and each domain can comprise four framework regions (FRs), whose sequences can be somewhat conserved, connected by three hyper-variable regions or CDRs. The four FRs can largely adopt a β-sheet conformation and the CDRs can form loops connecting, and in some cases forming part of, the β-sheet structure. The CDRs in each chain can be held in close proximity by the FRs and, with the CDRs from the other chain, can contribute to the formation of the antigen binding site.

The domains of natural light and heavy chains can have the same general structures, and each domain can comprise four framework regions, whose sequences can be somewhat conserved, connected by three hyper-variable regions or CDRs. The four framework regions can largely adopt a β-sheet conformation and the CDRs can form loops connecting, and in some aspects forming part of, the β-sheet structure. The CDRs in each chain can be held in close proximity by the framework regions and, with the CDRs from the other chain, can contribute to the formation of the antigen binding site. The heavy chain CDRs can be referred to as HCDR1, HCDR2, and HCDR3. The light chain CDRs can be referred to as LCDR1, LCDR2, and LCDR3.

An antibody can include an antibody of any type, which can be assigned to different classes of immunoglobins, e.g., IgA, IgD, IgE, IgG, and IgM. Several different classes can be further divided into isotypes, e.g., IgG1, IgG2, IgG3, IgG4, IgA1, and IgA2. An antibody can further comprise a light chain and a heavy chain, often more than one chain. The heavy-chain constant regions (Fc) that corresponds to the different classes of immunoglobulins can be α, δ, ε, γ, and μ, respectively. The light chains can be one of either kappa or κ and lambda or λ, based on the amino acid sequences of the constant domains. The Fc region can contain an Fc domain. An Fc receptor can bind an Fc domain. An antibody can also include any fragment or recombinant forms thereof, including but not limited to scFvs, 'T-bodies', anti-calins, centyrins, affibodies, domain antibodies, or peptibodies.

An antibody can comprise an antigen binding domain which can refer to a portion of an antibody comprising the antigen recognition portion, i.e., an antigenic determining variable region of an antibody sufficient to confer recognition and binding of the antigen recognition portion to a target, such as an antigen, i.e., the epitope. Examples of antibody binding domains can include, but are not limited to, Fab, variable Fv fragment and other fragments, combinations of fragments or types of fragments known or knowable to one of ordinary skill in the art.

An antibody construct can comprise an antigen binding domain of an antibody. An antigen binding domain of an antibody can comprise one or more light chain (LC) CDRs and one or more heavy chain (HC) CDRs. For example, an antibody binding domain of an antibody can comprise one or more of the following: a light chain complementary determining region 1 (LCDR1), a light chain complementary determining region 2 (LCDR2), or a light chain complementary determining region 3 (LCDR3). As another example, an antibody binding domain can comprise one or more of the following: a heavy chain complementary determining region 1 (HCDR1), a heavy chain complementary determining region 2 (HCDR2), or a heavy chain complementary determining region 3 (HCDR3).

An antibody can comprise an antibody fragment. An antibody fragment can include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; and (iii) a Fv fragment consisting of the $V_L$ and $V_H$ domains of a single arm of an antibody. Although the two domains of the Fv fragment, $V_L$ and $V_H$, can be coded for by separate genes, they can be linked by a synthetic linker to be made as a single protein chain in which the $V_L$ and $V_H$ regions pair to form monovalent molecules.

F(ab')2 and Fab' moieties can be produced by treating immunoglobulin (monoclonal antibody) with a protease such as pepsin and papain, and can include an antibody fragment generated by digesting immunoglobulin near the disulfide bonds existing between the hinge regions in each of the two H chains. The Fab fragment can also contain the constant domain of the light chain and the first constant domain (CH1) of the heavy chain. Fab' fragments can differ from Fab fragments by the addition of a few residues at the carboxyl terminus of the heavy chain CH1 domain including one or more cysteine(s) from the antibody hinge region.

An Fv can be the minimum antibody fragment which contains a complete antigen-recognition and antigen-binding site. This region can consist of a dimer of one heavy chain and one light chain variable domain in tight, non-covalent association. In this configuration the three hypervariable regions of each variable domain can interact to define an antigen-binding site on the surface of the $V_H$-$V_L$ dimer. A single variable domain (or half of an Fv comprising only three hypervariable regions specific for an antigen) can recognize and bind antigen, although at a lower affinity than the entire binding site.

As used herein, the abbreviations for the natural 1-enantiomeric amino acids are conventional and can be as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Unless otherwise specified, X can indicate any amino acid. In some aspects, X can be asparagine (N), glutamine (Q), histidine (H), lysine (K), or arginine (R).

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

An anti-TNFR2 antibody can bind to soluble TNFR2. An anti-TNFR2 antibody can bind to membrane-bound TNFR2. The TNFR2 can be human TNFR2. An anti-TNFR2 antibody can bind to cynomolgus monkey TNFR2. An anti-TNFR2 antibody can be derived from mammal. For example, an anti-TNFR2 antibody can be derived from a mouse, rat, hamster, goat, sheep, rabbit, non-human primate, or human. Some exemplary murine variable region heavy chain ($V_H$) sequences, as shown in TABLE 1, can be SEQ ID NO: 1, SEQ ID NO: 3, and SEQ ID NO: 5. An exemplary rat $V_H$ sequence, also shown in TABLE 1, can be SEQ ID NO: 7. These exemplary murine $V_H$ sequences can be paired with exemplary murine variable region light chain ($V_L$) sequences, as shown in Table 2, which can be SEQ ID NO: 2, SEQ ID NO: 4, and SEQ ID NO: 6 to produce an anti-TNFR2 antibody that can bind to TNFR2, respectively. The exemplary rat $V_H$ sequence can be paired with exemplary rat variable region light chain ($V_L$) sequences, as shown in TABLE 2, which can be SEQ ID NO: 8, and SEQ ID NO: 9. For example, SEQ ID NO: 1 can be paired with SEQ ID NO: 2; SEQ ID NO: 3 can be paired with SEQ ID NO: 4; SEQ ID NO: 5 can be paired with SEQ ID NO: 6;

SEQ ID NO: 7 can be paired with SEQ ID NO: 8; and SEQ ID NO: 7 can be paired with SEQ ID NO: 9.

TABLE 1

Exemplary anti-TNFR2 antibody Variable Region Heavy Chain Sequences

| SEQ ID NO: | Sequence |
|---|---|
| SEQ ID NO: 1 | EVQLQQSGAELVKPGASVKISCKASGYTFTDYNMDWVKQSHGKSLEWIGDINPNYESTSYNQKFKGKATLTVDKSSSTAYMEVRSLTSEDTAVFYCARDKGWYFDVWGAGTTVTVSS |
| SEQ ID NO: 3 | QVTLKESGPGILQPSQTLSLTCSFSGFSLSTSGMGVGWIRQPSGKGLEWLAHIWWDDDKFYNPSLKSQLTISKDTSRNQVFLKLTSVVTADTATYYCARLTGTRYFDYWGQGTTLTVSS |
| SEQ ID NO: 5 | QIQLVQSGPELKKPGETVKISCKASGYTFTDYSMHWVKQAPGKGLKWMGWINTETGEPTYADDFKGRFAFSSETSTSTAYLQINNLKNDDTTTYFCATYYGSSYVPDYWGQGTSLTVSS (SEQ ID NO: 5) |
| SEQ ID NO: 7 | EVQLQQSGPEVGRPGSSVKISCKASGYTFTDYIMHWVKQSPGQGLEWIGWVDPEYGSTDYAEKFKKKATLTADTSSNTAYIQLSSLTSEDTATYFCARDDGSYSPFDYWGQGVMVTVSS (SEQ ID NO: 7) |

TABLE 2

Exemplary anti-TNFR2 antibody Variable Region Light Chain Sequences

| SEQ ID NO: | Sequence |
|---|---|
| SEQ ID NO: 2 | ENVLTQSPAIMSASLGEKVTMSCRASSSVKNMYWYQQKSDASPKLWIYYTSNLAPGVPARFSGSGSGNSYSLTISSMEGEDAATYYCQQFTSSPYTFGGGTKLELK |
| SEQ ID NO: 4 | DVQMTQSPSSLSASLGGKVTITCKASQDINKFIAWYQHKPGKGPRLLIHYTSTLQPGIPSKFSGSGSGRDYSFSISNLEPEDIATYYCLQYGNLWTFGGGTKLEIT |
| SEQ ID NO: 6 | DIVMTQSHKFMSTSVGDRVSITCKASQNVGTAVAWYQHKPGQSPKLLIYWTSSRHTGVPDRFTGSGSGTEFTLTISNVQSEDLADYFCHQYSDYPYTFGGGTKLEIK |
| SEQ ID NO: 8 | DIQMTQSPPSLSASLGDKVTITCQASQNINKYIAWYQQKPGKAPRLLIRYTSTLESGTPSRFSGSGSGRDYSFSISNVESEDIASYYCLQYVNLLTFGAGTKLEIK |
| SEQ ID NO: 9 | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIK |

An antibody that can bind to a receptor protein can be generated by standard techniques such as immunization using human receptor proteins. These antibodies can be generated by immunization of an animal using an adjuvant such as Freund's adjuvant in combination with an immunogenic amount of the protein administered over a period of weeks in two to three week intervals. Antibodies against the administered protein can then be isolated from the serum. Antibodies can also be generated from hybridomas made from immunoglobulin producing cells from the immunized animals, which can express the antibodies in culture. However, because these methods yield antibody which is not of human origin, these antibodies may elicit an adverse effect if administered to humans. Therefore, it can be advantageous to make a non-human antibody a chimeric antibody or to humanize the non-human antibody. A chimeric antibody can comprise the heavy chain variable region and the light chain variable region of the non-human antibody fused with the constant region (Fc domain) of a human antibody, such as a human IgG1 Fc domain. The whole Fc domain or part of the Fc domain can be from a human Fc domain. Amino acid residues in the Fc domain can be substituted to increase or decrease affinity to Fcγ receptors. Amino acid residues in the Fc domain can be substituted to be null, meaning the Fc domain does not bind Fc receptors or can bind with such low affinity and/or avidity as to not cause any Fc receptor signaling as a result of binding. The Fc domain can be null for binding to Fcγ receptors. Some example Fcγ receptors for which the Fc domain can be null for binding can be, but not limited to, FcγRI (CD64), FcγRIIA (CD32a), FcγRIIB (CD32b), FcγRIIIA (CD16a), FcγRIIIA (CD16a) F158 variant, FcγRIIIA (CD16a) V158 variant, or FcγRIIIB (CD16b). Humanized forms of antibodies can be chimeric antibodies that can comprise at least some sequence from a human and at least some sequence from a non-human. For example, a non-human sequence can be obtained from a mouse, rat, hamster, goat, sheep, rabbit, or non-human primate. A humanized antibody can be a human immunoglobulin (i.e., recipient antibody) in which residues from a hypervariable region of the recipient can be replaced by residues from a hypervariable region of a non-human species (i.e., donor antibody) such as mouse, rat, hamster, goat, sheep, rabbit, or non-human primate having the desired specificity, affinity, and capacity for binding an antigen. In some instances, the FR residues of the human immunoglobulin can be replaced by corresponding non-human residues. Furthermore, a humanized antibody can comprise residues that are not found in the recipient antibody or in the donor antibody. These modifications can be made to further refine antibody performance. As in a chimeric antibody, the humanized antibody also can comprise at least a portion of an immunoglobulin constant region (Fc domain). The entire Fc domain or part of the Fc domain can be from a human Fc domain. Amino acid residues in the Fc domain can be substituted to increase or decrease affinity and/or affinity to Fc receptors. Amino acid residues in the Fc domain can be substituted to be null, meaning the Fc domain does not bind Fc receptors or can bind with such low affinity and/or avidity as to not cause any Fc receptor signaling as a result of binding. The Fc domain can be null for binding to Fcγ receptors. Some example Fcγ receptors for which the Fc domain can be null for binding can be, but not limited to, FcγRI (CD64), FcγRIIA (CD32a), FcγRIIB (CD32b), FcγRIIIA (CD16a), FcγRIIIA (CD16a) F158 variant, FcγRIIIA (CD16a) V158 variant, or FcγRIIIB (CD16b). Therefore, an anti-TNFR2 antibody can be a chimeric, humanized, or fully human antibody. The anti-TNFR2 antibody can comprise a human IgG1 Fc domain. The anti-TNFR2 antibody can comprise a human IgG1 Fc domain wherein the human IgG1 Fc domain is null for binding to an Fcγ receptor, such as FcγRI (CD64), FcγRIIA (CD32a), FcγRIIB (CD32b), FcγRIIIA (CD16a), FcγRIIIA (CD16a) F158 variant, FcγRIIIA (CD16a) V158 variant, or FcγRIIIB (CD16b). A chimeric anti-TNFR2 antibody can comprise at least 80% sequence identity to 6 contiguous amino acids between amino acid 20 and amino acid 110 of SEQ ID NO. 1. A chimeric anti-TNFR2 antibody can be comprise at least 80% sequence identity to 6 contiguous amino acids between amino acid 20 and amino acid 100 of SEQ ID NO. 2. A chimeric anti-TNFR2 antibody can comprise at least 80% sequence identity to 6 contiguous amino acids between amino acid 20 and amino acid 110 of SEQ ID NO. 3. A chimeric anti-TNFR2 antibody can comprise at least 80% sequence identity to 6 contiguous amino acids between amino acid 20 and amino acid 100 of SEQ ID NO. 4. A chimeric anti-TNFR2 antibody can comprise at least 80% sequence identity to 6 contiguous amino acids between amino acid 20 and amino acid 110 of SEQ ID NO. 5. A chimeric anti-TNFR2 antibody can comprise at least 80% sequence identity to 6 contiguous amino acids between amino acid 20 and amino acid 100 of SEQ ID NO. 6. A chimeric anti-TNFR2 antibody can comprise at least 80% sequence identity to 6 contiguous amino acids between amino acid 20 and amino acid 110 of SEQ ID NO. 7. A chimeric anti-TNFR2 antibody can comprise at least 80% sequence identity to 6 contiguous amino acids between amino acid 20 and amino acid 100 of SEQ ID NO. 8. A chimeric anti-TNFR2 antibody can comprise at least 80% sequence identity to 6 contiguous amino acids between amino acid 20 and amino acid 100 of SEQ ID NO. 9. A chimeric anti-TNFR2 antibody can be comprise a $V_H$ sequence having at least 80% sequence identity to an amino acid sequence of SEQ ID NO: 1; and a $V_L$ sequence having at least 80% sequence identity to an amino acid sequence of SEQ ID NO: 2. A chimeric anti-TNFR2 antibody can comprise a $V_H$ sequence having at least 90%, 95%, or 98% sequence identity to the amino acid sequence of SEQ ID NO: 1; and a $V_L$ sequence having at least 90%, 95%, or 98% sequence identity to the amino acid sequence of SEQ ID NO: 2. A chimeric anti-TNFR2 antibody can comprise a $V_H$ sequence having at least 80% sequence identity to the amino acid sequence of SEQ ID NO: 3; and a $V_L$ sequence having at least 80% sequence identity to the amino acid sequence of SEQ ID NO: 4. A chimeric anti-TNFR2 antibody can comprise a $V_H$ sequence having at least 90%, 95%, or 98% sequence identity to the amino acid sequence of SEQ ID NO: 3; and a $V_L$ sequence having at least 90%, 95%, or 98% sequence identity to the amino acid sequence of SEQ ID NO: 4. A chimeric anti-TNFR2 antibody can comprise a $V_H$ sequence having at least 80% sequence identity to the amino acid sequence of SEQ ID NO: 5; and a $V_L$ sequence having at least 80% sequence identity to the amino acid sequence of SEQ ID NO: 6. A chimeric antibody can comprise a $V_H$ sequence having at least 90%, 95%, or 98% sequence identity to the amino acid sequence of SEQ ID NO: 5; and a $V_L$ sequence having at least 90%, 95%, or 98% sequence identity to the amino acid sequence of SEQ ID NO: 6. A chimeric anti-TNFR2 antibody can comprise a $V_H$ sequence having at least 80% sequence identity to the amino acid sequence of SEQ ID NO: 7; and a $V_L$ sequence having at least 80% sequence identity to the amino acid sequence of SEQ ID NO: 8. A chimeric anti-TNFR2 antibody can comprise a $V_H$ sequence having at least 90%, 95%, or 98% sequence identity to the amino acid sequence of SEQ ID NO: 7; and a $V_L$ sequence having at least 90%, 95%, or 98% sequence identity to the amino acid sequence of SEQ ID NO: 8. A chimeric anti-TNFR2 antibody can comprise a $V_H$ sequence having at least 80% sequence identity to the amino acid sequence of SEQ ID NO: 7; and a $V_L$ sequence having at least 80% sequence identity to the amino acid sequence of SEQ ID NO: 9. A chimeric anti-TNFR2 antibody can comprise a $V_H$ sequence having at least 90%, 95%, or 98% sequence identity to the amino acid sequence of SEQ ID NO: 7; and a $V_L$ sequence having at least 90%, 95%, or 98% sequence identity to the amino acid sequence of SEQ ID NO: 9.

Humanized forms of antibodies can be chimeric antibodies that can comprise at least some sequence from a human and at least some sequence from non-human. A humanized antibody can be a monoclonal antibody. It can be constructed with antigen-binding regions (i.e., CDRs) that can be derived, at least in part, from a non-human source. The humanized antibody can contain at least one CDR that can be derived, at least in part, from a non-human source. The CDR can be derived from a light chain of an antibody or a heavy chain of an antibody. The remainder of the variable regions can be derived from a human source. The constant regions can be derived from a human source. A humanized anti-TNFR2 antibody can be a human antibody in which a CDR or fragment thereof can be replaced with a CDR or fragment thereof from a non-human anti-TNFR2 antibody. Alternatively, a humanized anti-TNFR2 antibody can be a non-human anti-TNFR2 antibody in which the constant region or fragment thereof can be replaced with a constant region or fragment thereof from a human antibody. For example, a non-human anti-TNFR2 CDR or fragment thereof can comprise at least in part a mouse anti-TNFR2 CDR or fragment thereof. Some exemplary CDRs from a murine anti-TNFR2 antibody can be isolated from SEQ ID NO: 1-SEQ ID NO: 9. For example, a CDR in SEQ ID NO: 1 can be SEQ ID NO: 10, SEQ ID NO: 11, or SEQ ID NO: 12 according to Kabat, or can be SEQ ID NO: 16, SEQ ID NO: 17, or SEQ ID NO: 18 according to the international ImMunoGeneTics information system (IMGT); a CDR in SEQ ID NO: 2 can be SEQ ID NO: 13, SEQ ID NO: 14, or SEQ ID NO: 15 according to Kabat, or can be SEQ ID NO: 19, SEQ ID NO: 20, and SEQ ID NO: 21 according to IMGT; a CDR in SEQ ID NO: 3 can be SEQ ID NO: 22, SEQ ID NO: 23, or SEQ ID NO: 24 according to Kabat, or can be SEQ ID NO: 28, SEQ ID NO: 29, or SEQ ID NO: 30 according to IMGT; a CDR in SEQ ID NO: 4 can be SEQ ID NO: 25, SEQ ID NO: 26, or SEQ ID NO: 27 according to Kabat, or can be SEQ ID NO: 31, SEQ ID NO: 32, or SEQ ID NO: 33 according to IMGT; a CDR in SEQ ID NO: 5 can be SEQ ID NO: 34, SEQ ID NO: 35, or SEQ ID NO: 36 according to Kabat, or can be SEQ ID NO: 40, SEQ ID NO: 41, or SEQ ID NO: 42 according to IMGT; a CDR in SEQ ID NO: 6 can be SEQ ID NO: 37, SEQ ID NO: 38, or SEQ ID NO: 39 according to Kabat, or can be SEQ ID NO: 43, SEQ ID NO: 44, or SEQ ID NO: 45 according to IMGT; a CDR in SEQ ID NO: 7 can be SEQ ID NO: 46, SEQ ID NO: 47, or SEQ ID NO: 48 according to Kabat, or can be SEQ ID NO: 55, SEQ ID NO: 56, or SEQ ID NO: 57 according to IMGT; a CDR in SEQ ID NO: 8 can be SEQ ID NO: 49, SEQ ID NO: 50, or SEQ ID NO: 51 according to Kabat, or can be SEQ ID NO: 58, SEQ ID NO: 59, or SEQ ID NO: 60 according to IMGT; and a CDR in SEQ ID NO: 9 can be SEQ ID NO: 52, SEQ ID NO: 53, or SEQ ID NO: 54 according to Kabat, or can be SEQ ID NO: 61, SEQ ID NO: 62, or SEQ ID NO: 63 according to IMGT. The sequences for SEQ ID NO: 10-SEQ ID NO: 63 are shown in the below TABLE 3 and TABLE 4.

TABLE 3

Exemplary Anti-TNFR2 antibody Heavy Chain CDR Sequences

| SEQ ID NO: | Sequence |
| --- | --- |
| SEQ ID NO: 10 | DYNMD |
| SEQ ID NO: 11 | DINPNYESTSYNQKFK |
| SEQ ID NO: 12 | DKGWYFDV |
| SEQ ID NO: 16 | GYTFTDYN |
| SEQ ID NO: 17 | INPNYEST |
| SEQ ID NO: 18 | RDKGWYFDV |
| SEQ ID NO: 22 | TSGMGVG |
| SEQ ID NO: 23 | HIWWDDDKFYNPSLKS |
| SEQ ID NO: 24 | TGTRYFDY |
| SEQ ID NO: 28 | GFSLSTSGMG |
| SEQ ID NO: 29 | HIWWDDDK |
| SEQ ID NO: 30 | ARLTGTRYFDY |
| SEQ ID NO: 34 | DYSMH |
| SEQ ID NO: 35 | WINTETGEPTYADDFKG |
| SEQ ID NO: 36 | YYGSSYVPDY |
| SEQ ID NO: 40 | GYTFTDYS |
| SEQ ID NO: 41 | INTETGEP |
| SEQ ID NO: 42 | ATYYGSSYVPDY |
| SEQ ID NO: 46 | DYIMH |
| SEQ ID NO: 47 | WVDPEYGSTDYAEKFKKK |
| SEQ ID NO: 48 | DDGSYSPFDY |
| SEQ ID NO: 55 | GYTFTDY |
| SEQ ID NO: 56 | WVDPEYGS |
| SEQ ID NO: 57 | ARDDGSYSPFDY |

TABLE 4

Exemplary anti-TNFR2 Antibody Light Chain CDR Sequences

| SEQ ID NO: | Sequence |
| --- | --- |
| SEQ ID NO: 13 | RASSSVKNMY |
| SEQ ID NO: 14 | YTSNLAP |
| SEQ ID NO: 15 | QQFTSSPYT |
| SEQ ID NO: 19 | SSVKN |
| SEQ ID NO: 20 | YTS |
| SEQ ID NO: 21 | QQFTSSPYT |
| SEQ ID NO: 25 | KASQDINKFIA |
| SEQ ID NO: 26 | YTSTLQP |
| SEQ ID NO: 27 | LQYGNLWT |
| SEQ ID NO: 31 | QDINKFI |
| SEQ ID NO: 32 | YTS |
| SEQ ID NO: 33 | LQYGNLWT |
| SEQ ID NO: 37 | KASQNVGTAVA |
| SEQ ID NO: 38 | WTSSRHT |
| SEQ ID NO: 39 | HQYSDYPYTF |
| SEQ ID NO: 43 | QNVGTA |
| SEQ ID NO: 44 | WTS |
| SEQ ID NO: 45 | QYSDYPYT |
| SEQ ID NO: 49 | QASQNINKYIA |
| SEQ ID NO: 50 | YTSTLES |
| SEQ ID NO: 51 | LQYVNLLT |
| SEQ ID NO: 52 | KASENVVTYVS |
| SEQ ID NO: 53 | GASNRYT |
| SEQ ID NO: 54 | GQGYSYPYT |
| SEQ ID NO: 58 | QNINKY |
| SEQ ID NO: 59 | YTS |
| SEQ ID NO: 60 | LQYVNLLT |
| SEQ ID NO: 61 | ENVVTY |
| SEQ ID NO: 62 | GAS |
| SEQ ID NO: 63 | GQGYSYPYT |

A humanized anti-TNFR2 antibody can comprise HCDR1 comprising an amino acid sequence of SEQ ID NO: 10; HCDR2 comprising an amino acid sequence of SEQ ID NO: 11; and HCDR3 comprising an amino acid sequence of SEQ ID NO: 12. This humanized anti-TNFR2 antibody can further comprise LCDR1 comprising an amino acid sequence of SEQ ID NO: 13; LCDR2 comprising an amino acid sequence of SEQ ID NO: 14; and LCDR3 comprising an amino acid sequence of SEQ ID NO: 15. A humanized anti-TNFR2 antibody can comprise HCDR1 comprising an amino acid sequence of SEQ ID NO: 16; HCDR2 comprising an amino acid sequence of SEQ ID NO: 17; and HCDR3 comprising an amino acid sequence of SEQ ID NO: 18. This humanized anti-TNFR2 antibody can further comprise LCDR1 comprising an amino acid sequence of SEQ ID NO: 19; LCDR2 comprising an amino acid sequence of SEQ ID NO: 20; and LCDR3 comprising an amino acid sequence of SEQ ID NO: 21. A humanized anti-TNFR2 antibody can comprise HCDR1 comprising an amino acid sequence of SEQ ID NO: 22; HCDR2 comprising an amino acid sequence of SEQ ID NO: 23; and HCDR3 comprising an amino acid sequence of SEQ ID NO: 24. The humanized anti-TNFR2 antibody can further comprise LCDR1 comprising an amino acid sequence of SEQ ID NO: 25; LCDR2 comprising an amino acid sequence of SEQ ID NO: 26; and LCDR3 comprising an amino acid sequence of SEQ ID NO: 27. A humanized anti-TNFR2 antibody can comprise HCDR1 comprising an amino acid sequence of SEQ ID NO: 28; HCDR2 comprising an amino acid sequence of SEQ ID NO: 29; and HCDR3 comprising an amino acid sequence of SEQ ID NO: 30. This humanized anti-TNFR2 antibody can further comprise LCDR1 comprising an amino acid sequence of SEQ ID NO: 31; LCDR2 comprising an amino acid sequence of SEQ ID NO: 32; and LCDR3 comprising an amino acid sequence of SEQ ID NO: 33. A humanized anti-TNFR2 antibody can comprise HCDR1 comprising an amino acid sequence of SEQ ID NO: 34; HCDR2 comprising an amino acid sequence of SEQ ID NO: 35; and HCDR3 comprising an amino acid sequence of SEQ ID NO: 36. This humanized anti-TNFR2 antibody can further comprise LCDR1 comprising an amino acid sequence of SEQ ID NO: 37; LCDR2 comprising an amino acid sequence of SEQ ID NO: 38; and LCDR3 comprising an amino acid sequence of SEQ ID NO: 39. A humanized anti-TNFR2 antibody can comprise HCDR1 comprising an amino acid sequence of SEQ ID NO: 40; HCDR2 comprising an amino acid sequence of SEQ ID NO: 41; and HCDR3 comprising an amino acid sequence of SEQ ID NO: 42. This humanized anti-TNFR2 antibody can further comprise LCDR1 comprising an amino acid sequence of SEQ ID NO: 43; LCDR2 comprising an amino acid sequence of SEQ ID NO: 44; and LCDR3 comprising an amino acid sequence of SEQ ID NO: 45. A humanized anti-TNFR2 antibody can comprise HCDR1 comprising an amino acid sequence of SEQ ID NO: 46; HCDR2 comprising an amino acid sequence of SEQ ID NO: 47; and HCDR3 comprising an amino acid sequence of SEQ ID NO: 48. This humanized anti-TNFR2 antibody can further comprise LCDR1 comprising an amino acid sequence of SEQ ID NO: 49; LCDR2 comprising an amino acid sequence of SEQ ID NO: 50; and LCDR3 comprising an amino acid sequence of SEQ ID NO: 51. This humanized anti-TNFR2 antibody can further comprise LCDR1 comprising an amino acid sequence of SEQ ID NO: 52; LCDR2 comprising an amino acid sequence of SEQ ID NO: 53; and LCDR3 comprising an amino acid sequence of SEQ ID NO: 54. A humanized anti-TNFR2 antibody can comprise HCDR1 comprising an amino acid sequence of SEQ ID NO: 55; HCDR2 comprising an amino acid sequence of SEQ ID NO: 56; and HCDR3 comprising an amino acid sequence of SEQ ID NO: 57. This humanized anti-TNFR2 antibody can further comprise LCDR1 comprising an amino acid sequence of SEQ ID NO: 58; LCDR2 comprising an amino acid sequence of SEQ ID NO: 59; and LCDR3 comprising an amino acid sequence of SEQ ID NO: 60. Alternatively, this this humanized anti-TNFR2 antibody can comprise LCDR1 comprising an amino acid sequence of SEQ ID NO: 61; LCDR2 comprising an amino acid sequence of SEQ ID NO: 62; and LCDR3 comprising an amino acid sequence of SEQ ID NO: 63. A humanized anti-TNFR2 antibody can comprise HCDR1 comprising an amino acid sequence of SEQ ID NO: 10; HCDR2 comprising an amino acid sequence of SEQ ID NO: 11; HCDR3 comprising an amino acid sequence of SEQ ID NO: 12; LCDR1 comprising an amino acid sequence of SEQ ID NO: 13; LCDR2 comprising an amino acid sequence of SEQ ID NO: 14; and LCDR3 comprising an amino acid sequence of SEQ ID NO: 15. A humanized anti-TNFR2 antibody can comprise HCDR1 comprising an amino acid sequence of SEQ ID NO: 16; HCDR2 comprising an amino acid sequence of SEQ ID NO: 17; HCDR3 comprising an amino acid sequence of SEQ ID NO: 18; LCDR1 comprising an amino acid sequence of SEQ ID NO: 19; LCDR2 comprising an amino acid sequence of SEQ ID NO: 20; and LCDR3 comprising an amino acid sequence of SEQ ID NO: 21. A humanized anti-TNFR2 antibody can comprise HCDR1 comprising an amino acid sequence of SEQ ID NO: 22; HCDR2 comprising an amino acid sequence of SEQ ID NO: 23; HCDR3 comprising an amino acid sequence of SEQ ID NO: 24; LCDR1 comprising an amino acid sequence of SEQ ID NO: 25; LCDR2 comprising an amino acid sequence of SEQ ID NO: 26; and LCDR3 comprising an amino acid sequence of SEQ ID NO: 27. A humanized anti-TNFR2 antibody can comprise HCDR1 comprising an amino acid sequence of SEQ ID NO: 28; HCDR2 comprising an amino acid sequence of SEQ ID NO: 29; HCDR3 comprising an amino acid sequence of SEQ ID NO: 30; LCDR1 comprising an amino acid sequence of SEQ ID NO: 31; LCDR2 comprising an amino acid sequence of SEQ ID NO: 32; and LCDR3 comprising an amino acid sequence of SEQ ID NO: 33. A humanized anti-TNFR2 antibody can comprise HCDR1 comprising an amino acid sequence of SEQ ID NO: 34; HCDR2 comprising an amino acid sequence of SEQ ID NO: 35; HCDR3 comprising an amino acid sequence of SEQ ID NO: 36; LCDR1 comprising an amino acid sequence of SEQ ID NO: 37; LCDR2 comprising an amino acid sequence of SEQ ID NO: 38; and LCDR3 comprising an amino acid sequence of SEQ ID NO: 39. A humanized anti-TNFR2 antibody can comprise HCDR1 comprising an amino acid sequence of SEQ ID NO: 40; HCDR2 comprising an amino acid sequence of SEQ ID NO: 41; HCDR3 comprising an amino acid sequence of SEQ ID NO: 42; LCDR1 comprising an amino acid sequence of SEQ ID NO: 43; LCDR2 comprising an amino acid sequence of SEQ ID NO: 44; and LCDR3 comprising an amino acid sequence of SEQ ID NO: 45. A humanized anti-TNFR2 antibody can comprise HCDR1 comprising an amino acid sequence of SEQ ID NO: 46; HCDR2 comprising an amino acid sequence of SEQ ID NO: 47; HCDR3 comprising an amino acid sequence of SEQ ID NO: 48; LCDR1 comprising an amino acid sequence of SEQ ID NO: 49; LCDR2 comprising an amino acid sequence of SEQ ID NO: 50; and LCDR3 comprising an amino acid sequence of SEQ ID NO: 51. A humanized anti-TNFR2 antibody can comprise HCDR1 comprising an amino acid sequence of SEQ ID NO: 46; HCDR2 comprising an amino acid sequence of SEQ ID NO: 47; HCDR3 comprising an amino acid sequence of SEQ ID NO: 48; LCDR1 comprising an amino acid sequence of SEQ ID NO: 52; LCDR2 comprising an amino acid sequence of SEQ ID NO: 53; and LCDR3 comprising an amino acid sequence of SEQ ID NO: 54. A humanized anti-TNFR2 antibody can comprise HCDR1 comprising an amino acid sequence of SEQ ID NO: 55; HCDR2 comprising an amino acid sequence of SEQ ID NO: 56; HCDR3 comprising an amino acid sequence of SEQ ID NO: 57; LCDR1 comprising an amino acid sequence of SEQ ID NO: 58; LCDR2 comprising an amino acid sequence of SEQ ID NO: 59; and LCDR3 comprising an amino acid sequence of SEQ ID NO: 60. A humanized anti-TNFR2 antibody can comprise HDCDR1 comprising an amino acid sequence of SEQ ID NO: 55; HCDR2 comprising an amino acid sequence of SEQ ID NO: 56; HCDR3 comprising an amino acid sequence of SEQ ID NO: 57; LCDR1 comprising an amino acid sequence of SEQ ID NO: 61; LCDR2 comprising an amino acid sequence of SEQ ID NO: 62; and LCDR3 comprising an amino acid sequence of SEQ ID NO: 63. A humanized anti-TNFR2 antibody can comprise at least 80% sequence identity to HCDR1 comprising an amino acid sequence of SEQ ID NO: 10; HCDR2 comprising an amino acid sequence of SEQ ID NO: 11; HCDR3 comprising an amino acid sequence of SEQ ID NO: 12; LCDR1 comprising an amino acid sequence of SEQ ID NO: 13; LCDR2 comprising an amino acid sequence of SEQ ID NO: 14; and LCDR3 comprising an amino acid sequence of SEQ ID NO: 15. A humanized anti-TNFR2 antibody can comprise at least 80% sequence identity to HCDR1 comprising an amino acid sequence of SEQ ID NO: 16; HCDR2 comprising an amino acid sequence of SEQ ID NO: 17; HCDR3 comprising an amino acid sequence of SEQ ID NO: 18; LCDR1 comprising an amino acid sequence of SEQ ID NO: 19; LCDR2 comprising an amino acid sequence of SEQ ID NO: 20; and LCDR3 comprising an amino acid sequence of SEQ ID NO: 21. A humanized anti-TNFR2 antibody can comprise at least 80% sequence identity to HCDR1 comprising an amino acid sequence of SEQ ID NO: 22; HCDR2 comprising an amino acid sequence of SEQ ID NO: 23; HCDR3 comprising an amino acid sequence of SEQ ID NO: 24; LCDR1 comprising an amino acid sequence of SEQ ID NO: 25; LCDR2 comprising an amino acid sequence of SEQ ID NO: 26; and LCDR3 comprising an amino acid sequence of SEQ ID NO: 27. A humanized anti-TNFR2 antibody can comprise at least 80% sequence identity to HCDR1 comprising an amino acid sequence of SEQ ID NO: 28; HCDR2 comprising an amino acid sequence of SEQ ID NO: 29; HCDR3 comprising an amino acid sequence of SEQ ID NO: 30; LCDR1 comprising an amino acid sequence of SEQ ID NO: 31; LCDR2 comprising an amino acid sequence of SEQ ID NO: 32; and LCDR3 comprising an amino acid sequence of SEQ ID NO: 33. A humanized anti-TNFR2 antibody can comprise at least 80% sequence identity to HCDR1 comprising the amino acid sequence of SEQ ID NO: 34; HCDR2 comprising an amino acid sequence of SEQ ID NO: 35; HCDR3 comprising an amino acid sequence of SEQ ID NO: 36; LCDR1 comprising an amino acid sequence of SEQ ID NO: 37; LCDR2 comprising an amino acid sequence of SEQ ID NO: 38; and LCDR3 comprising an amino acid sequence of SEQ ID NO: 39. A humanized anti-TNFR2 antibody can comprise at least 80% sequence identity to HCDR1 comprising an amino acid sequence of SEQ ID NO: 40; HCDR2 comprising an amino acid sequence of SEQ ID NO: 41; HCDR3 comprising an amino acid sequence of SEQ ID NO: 42; LCDR1 comprising an amino acid sequence of SEQ ID NO: 43; LCDR2 comprising an amino acid sequence of SEQ ID NO: 44; and LCDR3 comprising an amino acid sequence of SEQ ID NO: 45. A humanized anti-TNFR2 antibody can comprise at least 80% sequence identity to HCDR1 comprising an amino acid sequence of SEQ ID NO: 46; HCDR2 comprising an amino acid sequence of SEQ ID NO: 47; HCDR3 comprising an amino acid sequence of SEQ ID NO: 48; LCDR1 comprising an amino acid sequence of SEQ ID NO: 49; LCDR2 comprising an amino acid sequence of SEQ ID NO: 50; and LCDR3 comprising an amino acid sequence of SEQ ID NO: 51. A humanized anti-TNFR2 antibody can comprise at least 80% sequence identity to HCDR1 comprising an amino acid sequence of SEQ ID NO: 46; HCDR2 comprising an amino acid sequence of SEQ ID NO: 47; HCDR3 comprising an amino acid sequence of SEQ ID NO: 48; LCDR1 comprising an amino acid sequence of SEQ ID NO: 52; LCDR2 comprising an amino acid sequence of SEQ ID NO: 53; and LCDR3 comprising an amino acid sequence of SEQ ID NO: 54. A humanized anti-TNFR2 antibody can comprise at least 80% sequence identity to HCDR1 comprising an amino acid sequence of SEQ ID NO: 55; HCDR2 comprising an amino acid sequence of SEQ ID NO: 56; HCDR3 comprising an amino acid sequence of SEQ ID NO: 57; LCDR1 comprising an amino acid sequence of SEQ ID NO: 58; LCDR2 comprising an amino acid sequence of SEQ ID NO: 59; and LCDR3 comprising an amino acid sequence of SEQ ID NO: 60. A humanized anti-TNFR2 antibody can comprise at least 80% sequence identity to HCDR1 comprising an amino acid sequence of SEQ ID NO: 55; HCDR2 comprising an amino acid sequence of SEQ ID NO: 56; HCDR3 comprising an amino acid sequence of SEQ ID NO: 57; LCDR1 comprising an amino acid sequence of SEQ ID NO: 61; LCDR2 comprising an amino acid sequence of SEQ ID NO: 62; and LCDR3 comprising an amino acid sequence of SEQ ID NO: 63.

A humanized anti-TNFR2 antibody variable region heavy chain ($V_H$) sequence, as shown in TABLE 5, can be SEQ ID NO: 64, SEQ ID NO: 66, or SEQ ID NO: 68. A humanized anti-TNFR2 antibody variable region light chain ($V_L$) sequence, as shown in TABLE 6, which can be SEQ ID NO: 65, SEQ ID NO: 67, or SEQ ID NO: 69. A humanized anti-TNFR2 antibody $V_H$ sequence can be paired with a humanized anti-TNFR2 antibody $V_L$ sequence to produce a humanized anti-TNFR2 antibody that can bind to TNFR2. For example, SEQ ID NO: 64 can be paired with SEQ ID NO: 65; SEQ ID NO: 66 can be paired with SEQ ID NO: 67; SEQ ID NO: 66 can be paired with SEQ ID NO: 69; SEQ ID NO: 68 can be paired with SEQ ID NO: 67; and SEQ ID NO: 68 can be paired with SEQ ID NO: 69.

TABLE 5

Exemplary Humanized Anti-TNFR2 Antibody Variable Region Heavy Chain Sequences

| SEQ ID NO: | Sequence |
| --- | --- |
| SEQ ID NO: 64 | QVTLKESGPALVKPTQTLTLTCTFSGFSLSTSGMGVGWIRQPPGKALEWLAHIW WDDDKFYNPSLKSRLTISKDTSKNQVVLTMTNMDPVDTATYYCARITGTRYFD YWGQGTTVTVSS |
| SEQ ID NO: 66 | QVTLKESGPALVKPTQTLTLTCTFSGFSLSTSGMGVGWIRQPPGKALEWLAHIW WDDDKFYNPSLKSQLTISKDTSKNQVVLTMTNMDPVDTATYYCARITGTRYFD YWGQGTTVTVSS |

TABLE 5-continued

Exemplary Humanized Anti-TNFR2 Antibody Variable Region Heavy Chain Sequences

| SEQ ID NO: | Sequence |
| --- | --- |
| SEQ ID NO: 68 | QVTLKESGPALVKPTQTLTLTCTFSGFSLSTSGMGVGWIRQPPGKALEWLAHIW WDDDKFYNPSLKSRLTISKDTSKNQVVLTMTNMDPVDTATYYCARLTGTRYFD YWGQGTTVTVSS |

TABLE 6

Exemplary Humanized Anti-TNFR2 Antibody Variable Region Light Chain Sequences

| SEQ ID NO: | Sequence |
| --- | --- |
| SEQ ID NO: 65 | DIQMTQSPSSLSASVGDRVTITCKASQDINKFIAWYQQKPGKAPKLLIYYTSTLQP GVPSRFSGSGSGTDFTFTISSLQPEDIATYYCLQYGNLWTFGGGTKVEIK |
| SEQ ID NO: 67 | DVQMTQSPSSLSASVGDRVTITCKASQDINKFIAWYQQKPGKAPKLLIHYTSTLQ PGIPSRFSGSGSGTDFTFTISSLQPEDIATYYCLQYGNLWTFGGGTKVEIK |
| SEQ ID NO: 69 | DVQMTQSPSSLSASVGDRVTITCKASQDINKFIAWYQQKPGKAPKLLIHYTSTLQ PGIPSRFSGSGSGRDYTFTISSLQPEDIATYYCLQYGNLWTFGGGTKVEIK |

A humanized anti-TNFR2 antibody can comprise at least 80% sequence identity to 6 contiguous amino acids from amino acid 1 to amino acid 119 of SEQ ID NO: 64. A humanized anti-TNFR2 antibody can comprise at least 80% sequence identity to 6 contiguous amino acids from amino acid 1 to amino acid 106 of SEQ ID NO: 65. A humanized anti-TNFR2 antibody can comprise at least 80% sequence identity to 6 contiguous amino acids from amino acid 1 to amino acid 119 of SEQ ID NO: 66. A humanized anti-TNFR2 antibody can comprise at least 80% sequence identity to 6 contiguous amino acids from amino acid 1 to amino acid 106 of SEQ ID NO: 67. A humanized anti-TNFR2 antibody can comprise at least 80% sequence identity to 6 contiguous amino acids from amino acid 1 to amino acid 119 of SEQ ID NO: 68. A humanized anti-TNFR2 antibody can comprise at least 80% sequence identity to 6 contiguous amino acids from amino acid 1 and amino acid 106 of SEQ ID NO: 69. A humanized anti-TNFR2 antibody can comprise a $V_H$ sequence having at least 80% sequence identity to an amino acid sequence of SEQ ID NO: 64; and a $V_L$ sequence having at least 80% sequence identity to an amino acid sequence of SEQ ID NO: 65. A humanized anti-TNFR2 antibody can comprise a $V_H$ sequence having at least 90%, 95%, or 98% sequence identity to the amino acid sequence of SEQ ID NO: 64; and a $V_L$ sequence having at least 90%, 95%, or 98% sequence identity to the amino acid sequence of SEQ ID NO: 65. A humanized anti-TNFR2 antibody can comprise a $V_H$ sequence having at least 80% sequence identity to the amino acid sequence of SEQ ID NO: 66; and a $V_L$ sequence having at least 80% sequence identity to the amino acid sequence of SEQ ID NO: 67. A humanized anti-TNFR2 antibody can comprise a $V_H$ sequence having at least 90%, 95%, or 98% sequence identity to the amino acid sequence of SEQ ID NO: 66; and a $V_L$ sequence having at least 90%, 95%, or 98% sequence identity to the amino acid sequence of SEQ ID NO: 67. A humanized anti-TNFR2 antibody can comprise a $V_H$ sequence having at least 80% sequence identity to the amino acid sequence of SEQ ID NO: 66; and a $V_L$ sequence having at least 80% sequence identity to the amino acid sequence of SEQ ID NO: 69. A humanized anti-TNFR2 antibody can comprise a $V_H$ sequence having at least 90%, 95%, or 98% sequence identity to the amino acid sequence of SEQ ID NO: 66; and a $V_L$ sequence having at least 90%, 95%, or 98% sequence identity to the amino acid sequence of SEQ ID NO: 69. A humanized anti-TNFR2 antibody can comprise a $V_H$ sequence having at least 80% sequence identity to the amino acid sequence of SEQ ID NO: 68; and a $V_L$ sequence having at least 80% sequence identity to the amino acid sequence of SEQ ID NO: 67. A humanized anti-TNFR2 antibody can comprise a $V_H$ sequence having at least 90%, 95%, or 98% sequence identity to the amino acid sequence of SEQ ID NO: 68; and a $V_L$ sequence having at least 90%, 95%, or 98% sequence identity to the amino acid sequence of SEQ ID NO: 67. A humanized anti-TNFR2 antibody can comprise a $V_H$ sequence having at least 80% sequence identity to the amino acid sequence of SEQ ID NO: 68; and a $V_L$ sequence having at least 80% sequence identity to the amino acid sequence of SEQ ID NO: 69. A humanized anti-TNFR2 antibody can comprise a $V_H$ sequence having at least 90%, 95%, or 98% sequence identity to the amino acid sequence of SEQ ID NO: 68; and a $V_L$ sequence having at least 90%, 95%, or 98% sequence identity to the amino acid sequence of SEQ ID NO: 69.

An anti-TNFR2 CDR or fragment thereof can comprise an amino acid sequence that can specifically bind to a TNFR2, wherein said TNFR2, when bound to said amino acid sequence can reduce TNFR2 signaling as compared to the TNFR2 signaling resulting from TNFα binding to TNFR2. An anti-TNFR2 CDR sequence can be any one of SEQ ID NO: 10-SEQ ID NO: 63. An anti-TNFR2 CDR sequence can have at least 90%, 95%, or 99% sequence identity with any one of SEQ ID NO: 10-SEQ ID NO: 63.

Receptor signaling that can occur when a ligand binds to the ligand's receptor can be measured in many different ways. For example, receptor signaling can be measured by the resulting biological effects. Some biological effects that can be measured can be an increase and/or decrease in proteins associated with cellular signaling pathways, cytokine production, cell proliferation, and/or cell apoptosis. An anti-TNFR2 CDR can comprise a sequence with 100% sequence identity with an amino acid sequence that can bind to a TNFR2, wherein said TNFR2, when bound to said amino acid sequence can reduce TNFR2 signaling as compared to the TNFR2 signaling resulting from TNFα binding to TNFR2. An anti-TNFR2 CDR can comprise a sequence with 100% sequence identity with an amino acid sequence that can specifically bind to a TNFR2, wherein said TNFR2, when bound to said amino acid sequence can reduce TNFR2 signaling as compared to the TNFR2 signaling resulting from TNFα binding to TNFR2. An anti-TNFR2 CDR can comprise a sequence with 100% sequence identity with any one of SEQ ID NO: 10-SEQ ID NO: 63 that can bind to a TNFR2, wherein said TNFR2, when bound to any one of SEQ ID NO: 10-SEQ ID NO: 63 can reduce TNFR2 signaling as compared to the TNFR2 signaling resulting from TNFα binding to TNFR2. An anti-TNFR2 CDR can comprise a sequence with 100% sequence identity with any one of SEQ ID NO: 10-SEQ ID NO: 63 that can specifically bind to a TNFR2, wherein said TNFR2, when bound to any one of SEQ ID NO: 10-SEQ ID NO: 63 can reduce TNFR2 signaling as compared to the TNFR2 signaling resulting from TNFα binding to TNFR2. An anti-TNFR2 CDR can comprise a sequence with 90%, 80%, 70%, or 60% sequence identity with an amino acid sequence that can bind to a TNFR2, wherein said TNFR2, when bound to said amino acid sequence has reduced TNFR2 signaling as compared to the TNFR2 signaling resulting from TNFα binding to TNFR2. An anti-TNFR2 CDR can comprise a sequence with 90%, 80%, 70%, or 60% sequence identity with an amino acid sequence that can specifically bind to a TNFR2, wherein said TNFR2, when bound to said amino acid sequence can reduce TNFR2 signaling as compared to the TNFR2 signaling resulting from TNFα binding to TNFR2. An anti-TNFR2 CDR can comprise a sequence with 90%, 80%, 70%, or 60% sequence identity with any one of SEQ ID NO: 10-SEQ ID NO: 63 that can bind to a TNFR2, wherein said TNFR2, when bound to said amino acid sequence has reduced TNFR2 signaling as compared to the TNFR2 signaling resulting from TNFα binding to TNFR2. An anti-TNFR2 CDR can comprise a sequence with 90%, 80%, 70%, or 60% sequence identity with any one of SEQ ID NO: 10-SEQ ID NO: 63 that can specifically bind to a TNFR2, wherein said TNFR2, when bound to said amino acid sequence can reduce TNFR2 signaling as compared to the TNFR2 signaling resulting from TNFα binding to TNFR2. The antibody can bind to the soluble form and/or to the membrane-bound form of TNFR2. In some aspects, the antibody can block TNFα (GenBank accession # NP 000585, incorporated herein) from binding to TNFR2. The antibody can completely or partially block TNFα from binding to TNFR2. Completely blocking TNFα from binding to TNFR2 can completely or partially inhibit any downstream signaling that would normally result from TNFα binding to TNFR2. Partially blocking TNFα from partially binding to TNFR2 can completely or partially inhibit any downstream signaling that would normally result from TNFα binding to TNFR2. Blocking can inhibit 100% of the TNFR2 downstream signaling. It can inhibit up to 100% of the TNFR2 downstream signaling. It can inhibit up to 90% of the TNFR2 downstream signaling. It can inhibit up to 80% of the TNFR2 downstream signaling. It can inhibit up to 70% of the TNFR2 downstream signaling. It can inhibit up to 60% of the TNFR2 downstream signaling. It can inhibit up to 50% of the TNFR2 downstream signaling. It can inhibit up to 40% of the TNFR2 downstream signaling. It can inhibit up to 30% of the TNFR2 downstream signaling. It can inhibit up to 20% of the TNFR2 downstream signaling. It can inhibit up to 10% of the TNFR2 downstream signaling. It can inhibit up to 5% of the TNFR2 downstream signaling. It can inhibit up to 1% of the TNFR2 downstream signaling. The binding of the anti-TNFR2 antibody to TNFR2 itself can prevent any downstream signaling that would normally result from an agonist binding to TNFR2. Additionally, the anti-TNFR antibody can have a dissociation constant ($K_d$) for TNFR2 that is less than 100 nM, 75 nM, 50 nM, 40 nM, 30 nM, 20 nM, 10 nM, 5 nM, or 1 nM. The anti-TNFR antibody can have a dissociation constant ($K_d$) for TNFR2 that is less than 10 nM. The anti-TNFR antibody can have a dissociation constant ($K_d$) for TNFR2 that is less than 100 pM. It can have a $K_d$ for TNFR2 that is less than 50 pM. It can have a $K_d$ for TNFR2 that is less than 10 pM. It can have a $K_d$ for TNFR2 that is less than 5 pM. It can have a $K_d$ for TNFR2 that is less than 1 pM. It can have a $K_d$ for TNFR2 that is less than 0.5 pM. It can have a $K_d$ for TNFR2 that is less than 0.1 pM. The anti-TNFR2 antibody can bind to human TNFR2. The antibody can bind to non-human primate TNFR2, such as to cynomolgus monkey TNFR2. The anti-TNFR antibody can be purified, and can be combined with a pharmaceutically acceptable carrier. Additionally, one skilled in the art would recognize that these same concepts could apply to an anti-TNFR2 antibody created for use in the veterinary sciences and/or in laboratory animals.

Various compositions of humanized antibody are contemplated. For example, an anti-TNFR2 antibody can be an antibody fragment, such as a Fab, a single chain variable fragment (scFv), or an entire antibody. An entire humanized antibody can have one or more CDRs replaced with a non-human anti-TNFR2 CDR sequence. For example, a humanized antibody can have one or more CDRs replaced with any one of SEQ ID NO: 10-SEQ ID NO: 63, or any combination thereof. An anti-TNFR2 antibody can be conjugated with one or more agent(s) in order to generate an immunoconjugate. For example, an anti-TNFR2 antibody can be conjugated to a cytotoxic agent to generate an immunoconjugate. An anti-TNFR2 antibody can be an intact antibody, such as an intact IgG1 antibody.

Other modifications of an anti-TNFR2 antibody can be made. For example, an anti-TNFR2 antibody can be linked to one of a variety of nonproteinaceous polymers, such as polyethylene glycol, polypropylene glycol, polyoxyalkylenes, or copolymers of polyethylene glycol, and polypropylene glycol. An anti-TNFR2 antibody can be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nanoparticles and nanocapsules), or in macroemulsions.

An anti-TNFR2 antibody can be formulated as immunoliposomes. Liposomes containing an anti-TNFR2 antibody can be prepared by methods known in the art. Liposomes with enhanced circulation time can also be formulated with anti-TNFR2 antibodies.

An antibody disclosed herein can be nonnatural, designed, and/or engineered.

II. Methods for Producing Anti-TNFR2 Antibody

An anti-TNFR2 antibody can be produced by several methods to produce, for example, a fully human anti-TNFR2 antibody or a humanized anti-TNFR2 antibody as described herein.

As one example, an anti-TNFR2 antibody can be produced by a method using an isolated nucleic acid sequence encoding an anti-TNFR2 antibody, vectors and host cells comprising the nucleic acid sequence, and recombinant techniques for the production of the antibody. The nucleic acid sequence encoding the TNFR2 can be isolated into a replicable DNA vector for further cloning or for expression. DNA encoding an anti-TNFR2 antibody can be readily isolated and sequenced using conventional procedures (e.g., by using oligonucleotide probes that are capable of binding specifically to genes encoding the heavy and light chains of the antibody). Many vectors known in the art can be used as a vector. The vector components generally can include, but are not limited to, one or more of the following: a signal sequence, an origin of replication, one or more marker genes, an enhancer element, a promoter, and a transcription-termination sequence.

i) Signal Sequence Component

An anti-TNFR2 antibody can be produced recombinantly directly or as a fusion polypeptide with a heterologous polypeptide, which can be a signal sequence or other polypeptide having a cleavage site. The cleavage site can be at the N-terminus of the mature protein or polypeptide. The heterologous signal sequence selected can be one that can be recognized and processed (i.e., cleaved by a signal peptidase) by the host cell. For prokaryotic host cells that may not recognize and process the native anti-TNFR2 antibody signal sequence, the signal sequence can be substituted by a prokaryotic signal sequence selected, for example, from a group of the alkaline phosphatase, penicillinase, lpp, or heat-stable enterotoxin II leaders. For yeast secretion, the native signal sequence can be substituted by, for example, the yeast invertase leader, α-factor leader including *Saccharomyces* and *Kluyveromyces* α-factor leaders, acid-phosphatase leader, or the *C. albicans* glucoamylase leader. In mammalian cell expression, mammalian signal sequences as well as viral secretory leaders, for example the herpes simplex gD signal can be used. The DNA for such precursor region can be ligated in reading frame to DNA encoding an anti-TNFR2 antibody.

ii) Origin of Replication Component

Both expression and cloning vectors can contain a nucleic acid sequence that can enable the vector to replicate in one or more selected host cells. Generally, in cloning vectors, this sequence can be one that can enable the vector to replicate independently of the host chromosomal DNA, and can include an origin of replication or autonomously replicating sequence. Such sequences are well known for a variety of bacteria, yeast, and viruses. The origin of replication from the plasmid pBR322 can be suitable for most Gram-negative bacteria, the 2μ plasmid origin can be suitable for yeast, and various origins (SV40, polyoma, adenovirus, VSV or BPV) can be used for cloning vectors in mammalian cells. Generally, the origin of replication component can be omitted for mammalian expression vectors (the SV40 origin can be used only because it contains the early promoter).

iii) Selection Gene Component

An expression and cloning vector can contain a selection gene, which can also be termed a selectable marker. A typical selection gene can encode a protein that can (a) confer resistance to antibiotics or other toxins, e.g., ampicillin, neomycin, methotrexate, or tetracycline, (b) complement an auxotrophic deficiency, or (c) supply a critical nutrient not available from complex media, such as the gene encoding D-alanine racemase for Bacilli.

One example of a selection scheme utilizes a drug to arrest growth of a host cell. Those cells that are successfully transformed with a heterologous gene can produce a protein conferring drug resistance and thus can survive the selection regimen. Examples of such dominant selection can include the drugs neomycin, mycophenolic acid, and hygromycin.

Another example of a suitable selectable marker for mammalian cells are those that enable the identification of cells competent to take up the anti-TNFR antibody encoding nucleic acid sequence, such as dihydrofolate reductase, thymidine kinase, metallothionein-I and —II, adenosine deaminase, ornithine decarboxylase, etc.

For example, cells transformed with a dihydrofolate reductase selection gene can be first identified by culturing all of the transformants in a culture medium that contains methotrexate, a competitive antagonist of dihydrofolate reductase. An appropriate host cell where wild-type dihydrofolate reductase can be employed can be the Chinese hamster ovary (CHO) cell line deficient in dihydrofolate reductase activity.

Alternatively, host cells, such as wild-type hosts that contain endogenous dihydrofolate reductase, can be transformed or co-transformed with DNA sequences encoding anti-TNFR2 antibody, wild-type dihydrofolate reductase protein, and another selectable marker, such as aminoglycoside 3'-phosphotransferase, which can be selected by cell growth in medium containing a selection agent for the selectable marker such as an aminoglycosidic antibiotic like kanamycin, neomycin, or G418.

A suitable selection gene for use in yeast can be the trp1 gene present in the yeast plasmid YRp7. The trp1 gene can provide a selection marker for a mutant strain of yeast lacking the ability to grow in tryptophan. The presence of the trp1 lesion in the yeast host cell genome then can provide an effective environment for detecting transformation by growth in the absence of tryptophan. Similarly, a Leu2-deficient yeast strain can be complemented by a known plasmid bearing the Leu2 gene. In addition, vectors derived from the 1.6-μm circular plasmid pKD1 can be used for transformation of *Kluyveromyces* yeast.

iv) Promoter Component

Expression and cloning vectors can contain a promoter that can be recognized by the host organism and can be operably linked to an anti-TNFR2 antibody-encoding nucleic acid sequence. A promoter suitable for use with a prokaryotic host can include the phoA promoter, β-lactamase and lactose promoter systems, alkaline phosphatase, a tryptophan (trp) promoter system, and hybrid promoters such as the tac promoter. However, other known bacterial promoters can be suitable. Promoters for use in bacterial systems also can contain a Shine-Dalgarno sequence operably linked to the DNA sequence encoding an anti-TNFR2 antibody.

Promoter sequences can be recognized by eukaryotes. Eukaryotic genes can have an AT-rich region located approximately 25 to 30 bases upstream from the site where transcription can be initiated. Another sequence found 70 to 80 bases upstream from the start of transcription of many genes can be a CNCAAT region where N can be any nucleotide. An AATAAA sequence at the 3' end of a eukaryotic gene can signal for addition of the poly A tail to the 3' end of the coding sequence. All of these sequences can be inserted into eukaryotic expression vectors.

Examples of suitable promoting sequences for use with yeast hosts can include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which can be inducible promoters having the additional advantage of transcription controlled by growth conditions, can be the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Yeast enhancers also can be used with yeast promoters.

The transcription of a DNA sequence encoding an anti-TNFR2 antibody from a vector in a mammalian host cell can be controlled, for example, by a promoter obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40); heterologous mammalian promoters, such as the actin promoter or an immunoglobulin promoter; and heatshock promoters, provided such promoters are compatible with the host cell systems.

The early and late promoters of the SV40 virus can be obtained as an SV40 restriction fragment that also contains the SV40 viral origin of replication. The immediate early promoter of the human cytomegalovirus can be obtained as a HindIII E restriction fragment. A system for expressing DNA in mammalian hosts using the bovine papilloma virus as a vector can be used. A thymidine kinase promoter from herpes simplex virus can be used as a promoter. Alternatively, the rous sarcoma virus long-terminal repeat can be used as the promoter.

v) Enhancer Element Component

Transcription of a DNA sequence encoding an anti-TNFR2 antibody by higher eukaryotes can be increased by inserting an enhancer sequence into the vector. Many enhancer sequences are now known from mammalian genes (e.g., globin, elastase, albumin, a-fetoprotein, and insulin). However, an enhancer from a eukaryotic cell virus can be used. Examples can include the SV40 enhancer on the late side of the replication origin (bp 100-270), the cytomegalovirus early-promoter enhancer, the polyoma enhancer on the late side of the replication origin, and adenovirus enhancers. The enhancer can be spliced into the vector at a position 5' or 3' to an anti-TNFR2 antibody-encoding sequence.

vi) Transcription Termination Component

Expression vectors used in eukaryotic host cells (e.g., yeast, fungi, insect, plant, animal, human, or nucleated cells from other multicellular organisms) can also contain sequences necessary for the termination of transcription and for stabilizing the mRNA. Such sequences can be found at the 5' end or 3' end of untranslated regions of eukaryotic or viral DNAs or cDNAs. These regions contain nucleotide segments transcribed as polyadenylated fragments in the untranslated portion of the mRNA encoding an anti-TNFR antibody. One useful transcription termination component can be the bovine growth hormone polyadenylation region.

vii) Selection and Transformation of Host Cells

Suitable host cells for cloning or expressing the DNA vectors herein can be prokaryote, yeast, or higher eukaryote cells described herein. Suitable prokaryotes for this purpose can be eubacteria, such as Gram-negative or Gram-positive organisms. Some examples include, but are not limited to, *Escherichia, Enterobacter, Erwinia, Klebsiella, Proteus, Salmonella, Serratia, Shigella*, Bacilli, and *Pseudomonas*.

In addition to prokaryotes, eukaryotic microbes such as filamentous fungi or yeast can be suitable cloning or expression hosts for anti-TNFR2 antibody-encoding vectors. Some examples include, but are not limited to, *Saccharomyces cerevisiae; Schizosaccharomyces pombe; Kluyveromyces* hosts such as *K. lactis, K. fragilis, K. bulgaricus, K. wickeramii, K waltii, K. drosophilarum, K. thermotolerans,* and *K. marxianus; yarrowia; Pichia pastoris; Candida; Trichoderma reesia; Neurospora crassa; Schwanniomyces* such as *Schwanniomyces occidentalis*; and filamentous fungi such *Neurospora, Penicillium, Tolypocladium*, and *Aspergillus* hosts such as *A. nidulans* and *A. niger.*

Suitable host cells for expression of glycosylated anti-TNFR2 antibody can be derived from multicellular organisms. Examples of invertebrate cells can include, but are not limited to, plant and insect cells. Numerous baculoviral strains and variants and corresponding permissive insect host cells from hosts such as *Spodoptera frugiperda* (i.e., caterpillar), *Aedes aegypti* (i.e., mosquito), *Aedes ablopictus* (i.e., mosquito), *Drosophila melanogaster* (i.e., fruitfly) and *Bombyx mori* (i.e., silkworm) can be used. A variety of viral strains for transfection are publicly available, such as the L-1 variant of *Autographa californica* NPV and the Bm-5 strain of *Bombyx mori* NPV, and such viruses can be used as the virus for transfection of host cells.

Plant cell cultures of cotton, corn, potato, soybean, *petunia*, tomato, and tobacco can also be utilized as hosts.

Vertebrate cells can serve as host cells. Examples of mammalian host cell lines can include, but are not limited to, monkey kidney CV1 line transformed by SV40; human embryonic kidney line; baby hamster kidney cells; Chinese hamster ovary cells/-DHFR; mouse sertoli cells; monkey kidney cells; African green monkey kidney cells; human cervical carcinoma cells; canine kidney cells; buffalo rat liver cells; human lung cells; human liver cells; mouse mammary tumor; TRI cells; MRC 5 cells; FS4 cells; and a human hepatoma line.

Host cells can be transformed as described herein with expression or cloning vectors for anti-TNFR2 antibody production and cultured in conventional nutrient media modified as appropriate for inducing promoters, selecting transformants, or amplifying the genes encoding the desired sequences.

viii) Culturing the Host Cells

Host cells used to produce an anti-TNFR2 antibody can be cultured in a variety of media. Some examples of commercially available media that can be suitable for culturing the host cells are Ham's F10 (Sigma), Minimal Essential Medium ((MEM) (Sigma), RPMI-1640 (Sigma), and Dulbecco's Modified Eagle's Medium ((DMEM), Sigma). Any of these media can be supplemented as necessary with hormones and/or other growth factors (e.g., insulin, transferrin, or epidermal growth factor), salts (e.g., sodium chloride, calcium, magnesium, and phosphate), buffers (e.g., HEPES), nucleotides (e.g., adenosine and thymidine), antibiotics (e.g., as Gentamycin™ drug), trace elements (e.g., inorganic compounds usually present at final concentrations in micromolar range), and glucose or an equivalent energy source. Any other necessary supplements can also be included at appropriate concentrations that are known to those skilled in the art. The culture conditions, such as temperature, pH, and the like, can be those previously used with the host cell selected for expression, and will be apparent to the ordinarily skilled artisan.

ix) Purification of Anti-TNFR2 Antibody

When using recombinant techniques, an anti-TNFR2 antibody can be produced intracellularly, in the periplasmic space, or directly secreted into the medium. If the antibody is produced intracellularly, the particulate debris, either host cells or lysed fragments, can be removed, for example, by centrifugation or ultrafiltration. Where the antibody is secreted into the medium, supernatants from such expression systems can be concentrated using a commercially available protein concentration filter, for example, an AMICON™ or MILLIPORE PELLICON™ ultrafiltration unit. A protease inhibitor such as phenylmethylsuphonyl fluoride can be included in any of the foregoing steps to inhibit proteolysis, and antibiotics can be included to prevent the growth of adventitious contaminants.

The antibody composition prepared from the cells can be purified using, for example, hydroxylapatite chromatography, gel electrophoresis, dialysis, and affinity chromatography. The suitability of a protein A as an affinity ligand can depend on the species and isotype of any immunoglobulin Fc domain that may be present in the antibody. For example, protein A can be used to purify antibodies that are based on human γ1, γ2, or γ4 heavy chains. Protein G can be used for all mouse isotypes and for human γ3. The matrix to which the affinity ligand is attached can be agarose, but other matrices are available. Mechanically stable matrices, such as controlled-pore glass or poly(styrenedivinyl)benzene, can allow for faster flow rates and shorter processing times than can be achieved with agarose. Other techniques for protein purification such as fractionation on the an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation can also be used to recover the antibody.

Following any preliminary purification step(s), the mixture comprising the anti-TNFR2 antibody and contaminants can be subjected to low-pH hydrophobic-interaction chromatography using an elution buffer at a pH between about 2.5-4.5, and performed at low-salt concentrations (e.g., from 0-0.25M salt).

III. Method of Producing Humanized Antibodies

An anti-TNFR2 antibody as described herein can be humanized. The methods for humanizing antibodies can include, for example, humanization uses CDR grafting (Jones et al., *Nature* 15 321:522 (1986)) and variants thereof, including "reshaping" (Verhoeyen, et al., 1988 *Science* 239: 1534-1536; Riechmann, et al., 1988 *Nature* 332:323-337; Tempest, et al., *Bio/Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., B W Metcalf, B J Dalton (Eds.) Cellular adhesion: molecular definition to therapeutic potential. Plenum Press, New York; 1994:291-312). Superhumanization (Tan, et al., 2002 *J Immunol* 169: 1119-25) is another variant humanization method that can be used to graft non-human CDRs into human germline antibody sequences having similar CDR canonical structures. A humanized antibody can contain one or more amino acid residues introduced into the antibody from a source that is non-human. This non-human amino acid residue can be referred to as an import residue, which can be obtained from a variable domain of a non-human antibody. The import residue can then be used to as a substitute for a hypervariable region amino acid residue of a corresponding residue in a human antibody. Accordingly, such humanized antibodies can be chimeric antibodies. A chimeric antibody can contain substantially less than an intact human variable domain, which can be substituted by the corresponding sequence from a non-human species. A chimeric antibody can also contain an FR residue substituted by a residue from an analogous site in a non-human antibody either to restore the binding of the chimeric antibody to the target, to reduce the chimeric antibody's heterogeneity, or to remove T-cell epitopes.

One method for making humanized antibodies can utilize transgenic non-human animals. The transgenic non-human animals can be genetically engineered to contain one or more humanized immunoglobulin loci that can undergo gene rearrangement and gene conversion in the transgenic non-human animals to produce diversified humanized immunoglobulins.

Another example of a method for making humanized antibodies can utilize a mouse hybridoma cell line. The desired non-human antibody can be expressed by a mouse hybridoma cell line. These cells can be harvested and total RNA can be isolated. Complementary DNA (cDNA) can be generated that codes for the variable domains of the mouse antibody to be humanized. This can be accomplished using polymerase chain reaction (PCR) primers that can hybridize to the 5' ends of the mouse leader sequences and to the 5' ends of the mouse constant regions. The light chain and heavy chain variable regions can be cloned. PCR amplification of the cDNA can be accomplished using light and heavy chain specific primers. The PCR product can be cloned directly into a vector. This vector can be transformed into bacteria. The bacteria can be selected for colonies containing the vector with the mouse variable regions. The mouse variable regions can then be modified at the 5' and 3' ends using PCR primers to create restriction enzyme sites for convenient insertion into expression vectors, and to incorporate splice-donor sites for RNA splicing of the variable and constant regions. The modified mouse variable regions can be inserted into the FRs of a human antibody. The final vector can encode the CDRs grafted or humanized into the FRs of the human variable region and the human constant region. These vectors can contain human cytomegalovirus enhancer and promoter for transcription, a gene for selection of transformed cells, and the simian virus 40 origin of replication for COS cells. Expression of the humanized antibody can then be accomplished by transfection of mammalian cells.

Alternatively, a fragment for humanizing an antibody can be derived via proteolytic digestion of intact non-human antibodies. A fragment can also be produced by a recombinant host cell by several different methods. For example, an antibody fragment can be isolated from an antibody phage library. A Fab'-SH fragment can be directly recovered from *E. coli* and then chemically coupled with another Fab'-SH to form a F(ab')$_2$ fragments. A F(ab')$_2$ fragment can be isolated directly from recombinant host cell culture. Other techniques for the production of antibody fragments will be apparent to the skilled practitioner. An antibody can be a single-chain Fv fragment (scFv). An antibody fragment can also be a linear antibody.

The choice of human domains, both light and heavy, to be used in making the humanized antibodies can be very important to reduce antigenicity. For example, the sequence of the variable domain of a non-human antibody can be screened against an entire library of known human variable-domain sequences. The human sequence that is closest to that of the non-human can then be accepted as the human FR for the humanized antibody. Another method can use a particular FR derived from the consensus sequence of all human antibodies of a particular subgroup of light or heavy chains. The same FR can be used for several different humanized antibodies.

To retain a high affinity for an antigen and other biological properties, a humanized antibody can be prepared by a process of analysis of parental sequences and various conceptual humanized products using three-dimensional models of the parental and humanized sequences. Three-dimensional immunoglobulin models are commonly available and are familiar to those skilled in the art. Computer programs are available that can illustrate and display probable three-dimensional conformational structures of selected candidate immunoglobulin sequences. Inspection of these displays can permit analysis of the likely role of the residues in the functioning of the candidate immunoglobulin sequence. For example, this inspection can permit the analysis of residues that influence the ability of the candidate immunoglobulin to bind its antigen. In this way, FR residues can be selected and combined from the recipient and import sequences so that a desired antibody characteristic, such as increased affinity for a target antigen, can be achieved.

The hypervariable region residues in the FR can directly influence antigen binding. An anti-TNFR2 antibody can have a dissociation constant for TNFR2 that can be less than 100 nM $K_d$. An anti-TNFR2 antibody can have a dissociation constant for TNFR2 that can be less than 75 nM $K_d$. An anti-TNFR2 antibody can have a dissociation constant for TNFR2 that can be less than 50 nM $K_d$. An anti-TNFR2 antibody can have a dissociation constant for TNFR2 that can be less than 40 nM $K_d$. An anti-TNFR2 antibody can have a dissociation constant for TNFR2 that can be less than 30 nM $K_d$. An anti-TNFR2 antibody can have a dissociation constant for TNFR2 that can be less than 10 nM $K_d$. An anti-TNFR2 antibody can have a dissociation constant for TNFR2 that can be less than 5 nM $K_d$. An anti-TNFR2 antibody can have a dissociation constant for TNFR2 that can be less than 1 nM $K_d$. An anti-TNFR2 antibody can have a dissociation constant for TNFR2 that can be less than 100 pM $K_d$. An anti-TNFR2 antibody can have a dissociation constant for TNFR2 that can be less than 50 pM $K_d$. An anti-TNFR2 antibody can have a dissociation constant for TNFR2 that can be less than 10 pM $K_d$. An anti-TNFR2 antibody can have a dissociation constant for TNFR2 that can be less than 5 pM $K_d$. An anti-TNFR2 antibody can have a dissociation constant for TNFR2 that can be less than 1 pM $K_d$. An anti-TNFR2 antibody can have a dissociation constant for TNFR2 that can be less than 0.5 pM $K_d$. An anti-TNFR2 antibody can have a dissociation constant for TNFR2 that can be less than 0.1 pM $K_d$.

Another exemplary method of producing an anti-TNFR2 antibody can comprise selecting a non-human anti-TNFR2 antibody having at least one complementarity determining region, selecting a human antibody heavy chain, selecting a human antibody light chain, introducing at least one complementarity determining region or fragment thereof from the non-human anti-TNFR2 antibody heavy chain to form a recombinant heavy chain, and introducing at least one complementarity determining region or fragment thereof from the non-human anti-TNFR2 antibody into the human antibody light chain to form a recombinant light chain, characterized in that the selection of each of the human antibody heavy and light chains can be determined solely by sequence homology with the non-human anti-TNFR2 antibody heavy and light chains, respectively. A humanized antibody can contain an amino acid residue modification that can be different from either the non-human or human amino acid source, where the modification can maintain or improve affinity of the antibody. For example, the antibody variant of interest can have from about one to about five or about seven amino acid substitutions in the recombinant heavy chain sequence. As another example, the antibody variant of interest can have from about one to about five or about seven amino acid substitutions in the recombinant light chain sequence. Such antibody variants can be prepared by affinity maturation.

The present application also contemplates affinity-matured antibodies that can bind TNFR2. A parent antibody can be a chimeric antibody, a humanized antibody, or human antibody. The affinity-matured antibody can bind to TNFR2 with an affinity superior to 100 pM $K_d$. The affinity-matured antibody can bind to TNFR2 with an affinity superior to 50 pM $K_d$. The affinity-matured antibody can bind to TNFR2 with an affinity superior to 10 pM $K_d$. The affinity-matured antibody can bind to TNFR2 with an affinity superior to 5 pM $K_d$. The affinity-matured antibody can bind to TNFR2 with an affinity superior to 1 pM $K_d$. The affinity-matured antibody can bind to TNFR2 with an affinity superior to 0.5 pM $K_d$. The affinity-matured antibody can bind to TNFR2 with an affinity superior to 0.1 pM $K_d$.

IV. Pharmaceutical Composition

The compositions and methods described herein can be considered useful as pharmaceutical compositions for administration to a subject in need thereof. Pharmaceutical compositions can comprise at least the compositions described herein and one or more pharmaceutically acceptable carriers, diluents, excipients, stabilizers, dispersing agents, suspending agents, and/or thickening agents. A therapeutic composition of an anti-TNFR2 antibody as described herein can be prepared for storage by mixing an antibody having the desired degree of purity with a pharmaceutically acceptable carrier, excipient, and/or stabilizer. This formulation can be in the form of a lyophilized formulation or aqueous solution. An acceptable carrier, excipient, and/or stabilizer can be nontoxic to a recipient at the dosage and concentration employed. An acceptable carrier, excipient, and/or stabilizer can be a buffer such as phosphate, citrate, and other organic acids; an antioxidant including ascorbic acid and methionine; a preservative, (e.g., octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); a low-molecular-weight (e.g., less than about 10 residues) polypeptide; a protein, such as serum albumin, gelatin, or immunoglobulin; a hydrophilic polymer such as polyvinylpyrrolidone; an amino acid such as glycine, glutamine, asparagine, histidine, arginine, or lysine; a monosaccharide, a disaccharide, and other carbohydrates including glucose, mannose, or dextrin; a chelating agent such as EDTA; a sugar such as sucrose, mannitol, trehalose or sorbitol; a salt-forming counter-ion such as sodium; a metal complex (e.g., Zn-protein complexes); and/or a non-ionic surfactant such as TWEEN™, PLURONICS™ or polyethylene glycol (PEG).

Antibody compositions can be lyophilized (See, e.g., U.S. Pat. No. 6,267,958). Antibody compositions can be aqueous antibody (See, e.g., U.S. Pat. No. 6,171,586 and WO06/044908).

The composition herein can also contain more than one active compound as necessary for the particular indication being treated. The active compounds can have complementary activities that do not adversely affect each other. For example, an active compound can provide antibodies that bind to other antigens. Alternatively, or additionally, the composition can comprise a chemotherapeutic agent, cytotoxic agent, cytokine, growth-inhibitory agent, anti-hormonal agent, anti-angiogenic agent, and/or cardioprotectant. Such molecules can be present in combination in amounts that are effective for the purpose intended. Active ingredients can be entrapped in microcapsules (e.g., hydroxymethylcellulose or gelatin-microcapsules and poly-(methylmethacylate). Active ingredients can be entrapped in microcapsules in colloidal drug delivery systems (e.g., liposomes, albumin microspheres, microemulsions, nano-particles and nanocapsules) by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nano-particles and nanocapsules) or in macroemulsions.

The formulation herein can also contain more than one active ingredient as necessary for the particular indication being treated (e.g., cancer).

Sustained-release preparations can be prepared. Examples of sustained-release preparations can include semipermeable matrices of solid hydrophobic polymers that can contain the antibody, in which the matrices can be in the form of shaped articles (e.g., films or microcapsules). Examples of sustained-release matrices include polyesters, hydrogels (e.g., poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(–)-3-hydroxybutyric acid.

The pharmaceutical composition to be used for in vivo administration can be generally sterile (e.g., by filtration through sterile filtration membranes). Sterilization can be accomplished by filtration through sterile filtration.

V. Methods of Treatment

An anti-TNFR2 antibody can be administered to a patient in a therapeutically effective amount (i.e., an amount that has the desired therapeutic effect). An anti-TNFR2 antibody can be used in vivo or ex vivo. An anti-TNFR2 antibody can be either the fully human or humanized variants as described herein. An anti-TNFR2 antibody can be administered parenterally. The dose and dosage regimen can depend upon the severity of the diagnosis and the characteristics of the particular antibody used (e.g., its therapeutic index, the patient, and the patient's history). An anti-TNFR2 antibody can be administered continuously over a specified period of time. An anti-TNFR2 antibody can be administered intravenously. An anti-TNFR2 antibody can be administered intravenously to treat immune cells. An anti-TNFR2 antibody can be administered cutaneously. An anti-TNFR2 antibody can be administered subcutaneously. An anti-TNFR2 antibody can be administered intraperitoneally. An anti-TNFR2 antibody can be administered subcutaneously and intraperitoneally to treat regional lymph nodes. An anti-TNFR2 antibody can be administered at the site of a tumor or affliction. The administration can be made during the course of adjunct therapy such as combined cycles of radiation, chemotherapeutic treatment, or administration of tumor necrosis factor, interferon or other cyto-protective or immunomodulatory agent.

For parenteral administration, the antibody can be formulated in a unit dosage injectable form (e.g., letter solution, suspension, emulsion) in association with a pharmaceutically acceptable parenteral vehicle. Such vehicles can be inherently nontoxic and non-therapeutic. Examples of such vehicles can be water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability (e.g., buffers and preservatives).

An anti-TNFR2 antibody pharmaceutical composition can be used in therapy that can be formulated and with dosages that can be established in a fashion consistent with good medical practice taking into account the disorder to be treated, the condition of the individual patient, the site of delivery of the composition, the method of administration and other factors known to practitioners. The anti-TNFR2 antibody pharmaceutical composition can be prepared according to the description of preparation described herein.

An anti-TNFR2 antibody can be used in the treatment of cancer. The cancer can be a cancer causing a tumor comprising regulatory T cells expressing TNFR2. The cancer can be a cancer causing a tumor comprising T-cells wherein the ratio of regulatory T cells to effector T cells is greater than 1 to 10. The cancer can be a cancer that secretes TNFα. The cancer can be colorectal cancer, hepatocellular cancer, pancreatic cancer, breast cancer, melanoma, ovarian cancer, lung cancer, renal cancer, glioblastoma, leukemia, or lymphoma. Non-limiting examples of other cancers can include Acute lymphoblastic leukemia (ALL); Acute myeloid leukemia; Adrenocortical carcinoma; Astrocytoma, childhood cerebellar or cerebral; Basal-cell carcinoma; Bladder cancer; Bone tumor, osteosarcoma/malignant fibrous histiocytoma; Brain cancer; Brain tumors, such as, cerebellar astrocytoma, malignant glioma, ependymoma, medulloblastoma, visual pathway and hypothalamic glioma; Brainstem glioma; Breast cancer; Bronchial adenomas/carcinoids; Burkitt's lymphoma; Cerebellar astrocytoma; Cervical cancer; Cholangiocarcinoma; Chondrosarcoma; Chronic lymphocytic leukemia; Chronic myelogenous leukemia; Chronic myeloproliferative disorders; Colon cancer; Cutaneous T-cell lymphoma; Endometrial cancer; Ependymoma; Esophageal cancer; Eye cancers, such as, intraocular melanoma and retinoblastoma; Gallbladder cancer; Glioma; Hairy cell leukemia; Head and neck cancer; Heart cancer; Hepatocellular (liver) cancer; Hodgkin lymphoma; Hypopharyngeal cancer; Islet cell carcinoma (endocrine pancreas); Kaposi sarcoma; Kidney cancer (renal cell cancer); Laryngeal cancer; Leukemia, such as, acute lymphoblastic, acute myeloid, chronic lymphocytic, chronic myelogenous and, hairy cell; Lip and oral cavity cancer; Liposarcoma; Lung cancer, such as, non-small cell and small cell; Lymphoma, such as, AIDS-related, Burkitt; Lymphoma, cutaneous T-Cell, Hodgkin and Non-Hodgkin, Macroglobulinemia, Malignant fibrous histiocytoma of bone/osteosarcoma; Melanoma; Merkel cell cancer; Mesothelioma; Multiple myeloma/plasma cell neoplasm; Mycosis fungoides; Myelodysplastic syndromes; Myelodysplastic/myeloproliferative diseases; Myeloproliferative disorders, chronic; Nasal cavity and paranasal sinus cancer; Nasopharyngeal carcinoma; Neuroblastoma; Oligodendroglioma; Oropharyngeal cancer; Osteosarcoma/malignant fibrous histiocytoma of bone; Ovarian cancer; Pancreatic cancer; Parathyroid cancer; Pharyngeal cancer; Pheochromocytoma; Pituitary adenoma; Plasma cell neoplasia; Pleuropulmonary blastoma; Prostate cancer; Rectal cancer; Renal cell carcinoma (kidney cancer); Renal pelvis and ureter, transitional cell cancer; Rhabdomyo sarcoma; Salivary gland cancer; Sarcoma, Ewing family of tumors; Sarcoma, Kaposi; Sarcoma, soft tissue; Sarcoma, uterine; Sézary syndrome; Skin cancer (non-melanoma); Skin carcinoma; Small intestine cancer; Soft tissue sarcoma; Squamous cell carcinoma; Squamous neck cancer with occult primary, metastatic; Stomach cancer; Testicular cancer; Throat cancer; Thymoma and thymic carcinoma; Thymoma;

Thyroid cancer; Thyroid cancer, childhood; Uterine cancer; Vaginal cancer; Waldenström macroglobulinemia; Wilms tumor and any combination thereof.

EXAMPLES

The following examples are included to further describe some aspects of the present disclosure, and should not be used to limit the scope of the invention.

Example 1

Method of Making a Humanized Anti-TNFR2 Antibody

This example describes one method of a making a humanized anti-TNFR2 antibody. A variable domain of a murine anti-TNFR2 antibody that is comprised of an anti-TNFR2 CDR which can bind to a TNFR2 and when bound, can reduce TNFR2 signaling as compared to the TNFR2 signaling resulting from TNFα binding to TNFR2, is identified. The DNA sequence that is encoded by this CDR sequence is cloned into a vector for use in the production of a humanized anti-TNFR2 antibody, in which the CDR sequence of the human antibody is replaced be this murine CDR sequence. This vector is transfected into mammalian cells. Humanized anti-TNFR2 antibody is expressed by the mammalian cells, and is then purified from these cells.

Alternatively, three CDRs from a heavy chain variable region and three CDRs from a light chain variable region of a murine anti-TNFR2 antibody which can bind to a TNFR2 and when bound, can reduce TNFR2 signaling as compared to the TNFR2 signaling resulting from TNFα binding to TNFR2, are identified. The CDRs are any one of SEQ ID NO: 10-SEQ ID NO: 63. The DNA sequences that are encoded by these CDR sequences are cloned into a vector for use in the production of a humanized anti-TNFR2 antibody, in which the CDR sequences of the human antibody are replaced by these murine CDR sequences. This vector is transfected into mammalian cells. Humanized anti-TNFR2 antibody is expressed by the mammalian cells, and is then purified from these cells.

The purified humanized anti-TNFR2 antibody is characterized to ensure expression of each of the murine CDR in the human antibody framework. This is characterized by reconstructed mass spectra of reduced light chain and heavy chain of the humanized antibody, in which the murine CDR is shown to have replaced the human CDR of the human antibody. The expected integration of the murine CDR into the human antibody is also confirmed by chromatography, in which cation exchange chromatography and/or size exclusion chromatography can be used. Cation exchange chromatography is used to show the anticipated differences in charge between the humanized anti-TNFR2 antibody, the murine anti-TNFR2 antibody, and the human antibody. This is shown by cation exchange chromatography of the antibodies in their native form, and cation exchange chromatography of the antibodies after digestion with carboxypeptidase B. Size exclusion chromatography is used to show the anticipated size differences between the humanized anti-TNFR2 antibody, the murine anti-TNFR2 antibody, and human antibody. The replacement of the human CDR with the murine CDR in the humanized anti-TNFR2 antibody is shown by these tests.

Example 2

Characterization of the Binding of an Anti-TNFR2 Antibody to Soluble TNFR2

This example shows characterization of the binding of a humanized anti-TNFR2 antibody. A humanized anti-TNFR2 antibody as described in EXAMPLE 1 is produced. The purified humanized anti-TNFR2 antibody is characterized for its ability to bind to soluble TNFR2 and block binding of human TNFα to TNFR2. This is shown by performing surface plasmon resonance experiments. Biotinylated human TNFα is immobilized on a streptavidin-coated surface. The ability of the humanized anti-TNFR2 antibody to block the binding of soluble TNFR2 fusion protein fused to an IgG1 Fc to immobilized TNFα is then measured by surface plasmon resonance using a Biacore instrument. The humanized anti-TNFR2 antibody is bound to soluble TNFR2 fusion protein fused to an IgG1 Fc, and therefore the interaction between the immobilized TNFα and soluble TNFR2 fusion protein fused to an IgG1 Fc is blocked. Additionally, this blocking by the humanized anti-TNFR2 antibody is shown to be dose-dependent and to have saturating kinetics with respect to its binding to the soluble TNFR2 fusion protein fused to an IgG1 Fc. As a control, an anti-TNFR2 control antibody that is known to bind to TNFR2, but not block TNFα from binding to TNFR2, is used to show the specificity of the humanized anti-TNFR2 antibody blocking. The immobilized TNFα binding to the soluble TNFR2 fusion protein fused to an IgG1 Fc is not blocked by the anti-TNFR2 control antibody. Therefore, the specificity of the humanized anti-TNFR2 antibody for binding to TNFR2 and blocking TNFα from binding to TNFR2 is shown by surface plasmon resonance experiments.

Similarly, a surface plasmon resonance experiment with human TNFα that is captured on a carboxymethylated dextran-coated chip is used to show soluble TNFR2 fusion protein fused to an IgG1 Fc is blocked from binding with the immobilized TNFα by the humanized anti-TNFR2 antibody. In this experiment, the humanized anti-TNFR2 antibody is bound to soluble TNFR2 fusion protein fused to an IgG1 Fc, and therefore the interaction between the immobilized TNFα and soluble TNFR2 fusion protein fused to an IgG1 Fc is blocked. Additionally, this blocking by the humanized anti-TNFR2 antibody is shown to be dose-dependent and to have saturating kinetics with respect to its binding to the soluble TNFR2 fusion protein fused to an IgG1 Fc. As a control, an anti-TNFR2 control antibody that is known to bind to TNFR2, but not block TNFα from binding to TNFR2, is used to show the specificity of the humanized anti-TNFR2 antibody blocking. The immobilized TNFα binding to the soluble TNFR2 fusion protein fused to an IgG1 Fc is not blocked by the anti-TNFR2 control antibody. Therefore, the specificity of the humanized anti-TNFR2 antibody for binding to TNFR2 and blocking TNFα from binding to TNFR2 is shown by surface plasmon resonance experiments.

Example 3

TNFR2 is not Agonized by Humanized Anti-TNFR2 Antibody

This example shows that TNFR2 is not agonized when bound by humanized anti-TNFR2 antibody. A humanized anti-TNFR2 antibody as described in EXAMPLE 1 is produced.

A clonal human Jurkat cell line is transfected to stably express human TNFR2. Soluble human TNFα is incubated with this Jurkat cell line. Cell death is induced in the Jurkat cell line culture by the soluble human TNFα. In contrast, purified humanized anti-TNFR2 antibody is incubated with this Jurkat cell line and soluble human TNFα, but the soluble human TNFα induced cell death is decreased as compared with the Jurkat cell line cultures cultured only with soluble human TNFα. Therefore, the effect of soluble human TNFα is blocked by humanized anti-TNFR2 antibody. Furthermore, humanized anti-TNFR2 antibody is incubated with this Jurkat cell line, and the cell death in the Jurkat cell line culture in comparison with the Jurkat cell line culture alone is not increased. Hence, TNFR2 is not agonized by humanized anti-TNFR2 antibody binding.

Example 4

A Subpopulation of Cynomolgus Monkey Whole Blood Cells are Bound by Humanized Anti-TNFR2 Antibody This example shows that a subpopulation of cynomolgus monkey whole blood cells are bound by humanized anti-TNFR2 antibody. A humanized anti-TNFR2 antibody as described in EXAMPLE 1 is produced. Flow cytometry is used to show that purified humanized anti-TNFR2 antibody is bound to cynomolgus monkey TNFR2 on a subpopulation of $CD3^+$ cells in cynomolgus monkey whole blood cells.

First, cynomolgus monkey whole blood cells are incubated with OKT3 antibody conjugated to a fluorochrome. Although the OKT3 antibody is specific for human CD3, it can also bind to cynomolgus monkey CD3. The sample is then run through a flow cytometer. A subpopulation of the cynomolgus monkey whole blood cells are identified as $CD3^+$.

Furthermore, cynomolgus monkey whole blood cells are incubated with both the OKT3 antibody conjugated to a fluorochrome, and with the humanized anti-TNFR2 antibody. The sample is then incubated with a secondary antibody that is conjugated to a fluorochrome and that is specific for the Fc region of the humanized anti-TNFR2 antibody. This sample is run through a flow cytometer. A subpopulation of $CD3^+$ $TNFR2^+$ cells in cynomolgus monkey whole blood cells is identified. Additionally, whole blood cells are incubated with OKT3 antibody conjugated to a fluorochrome and with varying concentrations of the humanized anti-TNFR2 antibody. These samples are also incubated with a secondary antibody that is conjugated to a fluorochrome and that is specific for the Fc region of the humanized anti-TNFR2 antibody, and then the samples are run in a flow cytometer. The humanized anti-TNFR2 antibody is bound TNFR2 on $CD3^+$ cells with dose-dependent and saturating kinetics. In comparison, a control antibody is not bound to TNFR2 on $CD3^+$ cells with dose-dependent and saturating kinetics after incubation of cynomolgus monkey whole blood cells with OKT3 antibody conjugated to a fluorochrome and with varying concentrations of the control antibody, and then being run on the flow cytometer. Therefore, humanized anti-TNFR2 antibody can bind to TNFR2 in a $CD3^+$ subpopulation of cynomolgus monkey whole blood cells.

Example 5

A Subpopulation of $CD3^+$ Human Whole Blood Cells are Bound by Anti-TNFR2 Antibody This example shows that a subpopulation of human whole blood cells are bound by humanized anti-TNFR2 antibody. A humanized anti-TNFR2 antibody as described in EXAMPLE 1 is produced. Flow cytometry is used to show that purified humanized anti-TNFR2 antibody is bound to human TNFR2 on a $CD4^+$ $CD25^+$ $Foxp3^+$ subpopulation of $CD3^+$ cells in human whole blood cells.

First, human whole blood cells are incubated with OKT3 antibody conjugated to a fluorochrome, which is an antibody is specific for human CD3. The sample is then run through a flow cytometer. A $CD3^+$ subpopulation of the human whole blood cells are identified. Furthermore, human whole blood cells are incubated with both the OKT3 antibody conjugated to a fluorochrome, and with the humanized anti-TNFR2 antibody. The sample is then incubated with a secondary antibody conjugated to a fluorochrome and specific for the Fc region of the humanized anti-TNFR2 antibody. This sample is run through a flow cytometer. A subpopulation of $CD3^+$ $TNFR2^+$ cells in human whole blood cells are identified. Additionally, whole blood cells are incubated with OKT3 antibody conjugated to a fluorochrome and with varying concentrations of the humanized anti-TNFR2 antibody. These samples are then incubated with a secondary antibody that is conjugated to a fluorochrome and that is specific for the Fc region of the humanized anti-TNFR2 antibody, and then the samples are run on a flow cytometer. The humanized anti-TNFR2 antibody are bound to TNFR2 on $CD3^+$ cells with dose-dependent and saturating kinetics. In comparison, a control antibody is not bound to TNFR2 on $CD3^+$ cells with dose-dependent and saturating kinetics after incubation of human whole blood cells with OKT3 antibody conjugated to a fluorochrome and with varying concentrations of the control antibody, and then being run on a flow cytometer. Therefore, humanized anti-TNFR2 antibody can bind to TNFR2 in a $CD3^+$ subpopulation of cynomolgus monkey whole blood cells.

Furthermore, human $CD4^+$ $CD25^+$ $Foxp3^+$ T regulatory cells (Treg cells) are purified from human whole blood. This purified population of human Treg cells are then incubated with humanized anti-TNFR2 antibody, which are incubated with a secondary antibody conjugated to a fluorochrome and specific for the Fc region of the humanized anti-TNFR2 antibody. Humanized anti-TNFR2 antibody are bound to human Treg cells. As a result, this data can show that human Treg cells express TNFR2.

Example 6

Effects of Anti-TNFR2 Antibody on Human $CD4^+$ $CD25^+$ $Foxp3^+$ Regulatory T Cells This example shows how human $CD4^+$ $CD25^+$ $Foxp3^+$ regulatory T cells (Tregs) are affected when bound by anti-TNFR2 antibody. A humanized anti-TNFR2 antibody as described in EXAMPLE 1 is produced. Cell culturing is used to show expansion of human $CD4^+$ $CD25^+$ $Foxp3^+$ regulatory T cells is prevented by humanized anti-TNFR2 antibody.

Human Treg cells are purified and incubated with recombinant human TNFα and IL-2. Then, these cells are incubated with either the purified humanized anti-TNFR2 antibody or a control antibody. Anti-CD3 and anti-CD28 are also added to these cultures to stimulate the human Treg cells to expand. After incubating together, the Treg cell numbers are assessed. This is done by labeling the human Treg cells from the culture with fluorochromes and then running the sample of the culture in a flow cytometer with counting beads. Tt The culture that is incubated with the purified humanized anti-TNFR2 antibody has a lower number of human Treg cells compared to the number of human Treg cells from the culture that is incubated with the control antibody. Therefore, expansion of recombinant-human- TNFα-treated human Treg cells is inhibited by purified humanized anti-TNFR2 antibody.

Cell culturing experiments are used to show that cell-surface expression levels of TNFR2 on human Treg cells are reduced by purified humanized anti-TNFR2 antibody. Human Treg cells are purified and are incubated with the purified humanized anti-TNFR2 antibody or a control antibody. The human Treg cells are then labeled with an anti-TNFR2 antibody conjugated to a fluorochrome and are run on a flow cytometer. The mean fluorescent intensity (MFI) of human Treg cells that are incubated with the purified humanized anti-TNFR2 antibody is lower for TNFR2 compared to the TNFR2 MFI of Treg cells from the culture that is incubated with the control antibody. A lower TNFR2 MFI can indicate lower expression of cell-surface TNFR2. Therefore, TNFR2 cell-surface expression on human Treg cells is reduced by purified humanized anti-TNFR2 antibody.

Cell culturing is used to show recombinant-human-TNFα-treated human Treg cells are prevented by humanized anti-TNFR2 antibody from suppressing CD8$^+$ T cell proliferation. Human Treg cells are purified and are incubated with recombinant human TNFα and either the purified humanized anti-TNFR2 antibody or a control antibody. Separately, peripheral blood mononuclear cells (PBMCs) containing CD8$^+$ T cells are labeled with carboxyfluorescein succinmidyl ester (CFSE). The recombinant-human-TNFα-treated human Treg cells from cell cultures incubated with either the purified humanized anti-TNFR2 antibody or a control antibody are separately added to cell cultures containing the CFSE-labeled PBMCs. These cell cultures are incubated with anti-CD3 antibodies and IL-2. Samples from these cell cultures are incubated with fluorochromes that label the CD8$^+$ T cell population, which are then run on a flow cytometer. Dilution of the CFSE in the CD8$^+$ T cell population is shown by flow cytometry. More specifically, the CFSE-labeling is diluted in a greater percentage of CD8$^+$ T cells from the culture that contained recombinant-human-TNFα-treated human Treg cells incubated with the humanized anti-TNFR2 antibody than the culture that contained recombinant human TNFα-treated Treg cells incubated with a control antibody. A greater percentage of CD8$^+$ T cells with diluted CFSE-labeling is indicative that more proliferation of those CD8$^+$ T cells. Therefore, recombinant-human-TNFα-treated human Treg cells are prevented from suppressing CD8$^+$ T cell proliferation by anti-TNFR2 antibody.

Cell culturing is used to show the percentage of recombinant-human-TNFα-treated human Treg cells that produce IFNγ is increased by anti-TNFR2 antibody. Human Treg cells are purified and are incubated with recombinant human TNFα and either the purified humanized anti-TNFR2 antibody or a control antibody. The human Treg cells are then stimulated with phorbol 12-myristate 13-acetate (PMA) and ionomycin. After stimulation, the human Treg cells are labeled intercellularly for IFNγ, and then run on a flow cytometer. IFNγ is produced by a higher percentage of human Treg cells when incubated with the purified humanized anti-TNFR2 antibody than human Treg cells incubated with a control antibody. Therefore, the percentage of recombinant-human-TNFα-treated human Treg cells that secrete IFNγ is increased by anti-TNFR2 antibody.

Example 7

Anti-TNFR2 Antibody Reverse TNFα-Mediated Enhancement of Human Myeloid-Derived Suppressive Cells' Suppressive Function This example shows that human myeloid-derived suppressor cells' (MDSCs) suppressive function is reversed by anti-TNFR2 antibody. MDSCs are generated by culturing human CD14$^+$ monocytes with 10 ng/mL of GM-CSF and 10 ng/mL of IL-6 for 7 days. MDSCs are then activated with soluble TNFα (300 ng/mL) or paraformaldehyde-fixed membrane bound TNFα-expressing CHO cells (CHO to MDSC ratio of 10:1) for 24 hours. In some experiments, MDSCs were pre-incubated with humanized anti-TNFR2 antibody or an isotype control for 30 min prior to TNFα stimulation. To assess MDSC suppressive function, titrating numbers of TNFα-stimulated MDSC were cultured with proliferation dye-labeled autologous T cells in the presence of anti-CD3/CD28-labeled beads. At 96 hours, T cell proliferation was assessed by flow cytometry. Increased T cell proliferation is shown by flow cytometry when the T cells and MDSCs are cultured with the humanized anti-TNFR2 antibody.

Example 8

Anti-TNFR2 Antibodies Bind to Human and Cynomolgus Monkey TNFR2 Extracellular Domain This example shows that anti-TNFR2 antibodies bind to human and cynomolgus monkey TNFR2 extracellular domain (ECD). Four different anti-TNFR2 antibodies were purified by size exclusion chromatography. These four antibodies were SBT-001, SBT-002, SBT-003, and SBT-004. SBT-001 was comprised of the heavy chain variable region SEQ ID NO: 1 paired with the light chain variable region SEQ ID NO: 2. SBT-002 was comprised of the heavy chain variable region SEQ ID NO: 3 and the light chain variable region SEQ ID NO: 4. SBT-003 was comprised of the heavy chain variable region SEQ ID NO: 5 and the light chain variable region SEQ ID NO: 6. SBT-004 was comprised of the heavy chain variable region SEQ ID NO: 7 and the light chain variable region SEQ ID NO: 8.

Analysis of binding to the human and cynomolgus TNFR2 ECD was performed using an Octet Red 96 Instrument™ (ForteBio). SBT-001, SBT-002, SBT-003, and SBT-004 were independently immobilized on anti-mouse Fc biosensors, and incubated with varying concentration of monomeric human or cynomolgus TNFR2 ranging from 1.2 nM to 1 µM in PBS. The experiments were performed using five steps: (1) baseline acquisition (60 s); (2) antibody loading on to anti-mouse Fc biosensors (120 s); (3) second baseline acquisition (60 s); (4) association of interacting monomeric human or cynomolgus TNFR2 ECD protein for $k_{on}$ measurement (120 s); and (5) dissociation of interacting monomeric human or cynomolgus TNFR2 ECD for $k_{off}$ measurement (240-3600 s).

The interacting monomeric human or cynomolgus TNFR2 ECD was used at 5-6 concentrations of a 3-fold concentration series. The data were analyzed using Octet Data Analysis Software 9.0 ™ (ForteBio) and fit to the 1:1 binding model. The equilibrium dissociation constants (Id) were calculated by the ratio of $k_{on}$ to $k_{off}$. The data showed that SBT-001, SBT-002, SBT-003, and SBT-004 bound to human TNFR2 and cynomolgus TNFR2. (See TABLE 8)

Furthermore, competition ELISA was used to evaluate the ability of SBT-001, SBT-002, SBT-003, and SBT-004 to block TNFα from binding to TNFR2. Soluble human TNFR2 was coated on Nunc-Immuno™ plates. TNFα was biotinylated using an Innova Lightning-Link™ kit. The antibody samples were titrated at a constant concentration of biotinylated TNFα. Unbiotinylated TNFα and Fc-TNFR2 were run as positive controls, and an control mouse IgG1 was run on each plate as a negative control. Bound TNFα- biotin was detected using a streptavidin-HRP conjugate. SBT-001, SBT-002, SBT-003, and SBT-004 were all successfully able to decrease TNFα from binding to TNFR2. In comparison, two anti-TNFR2 antibodies known to bind to TNFR2 but not block TNFα binding (SBT-005 and SBT-007), were not able to decrease binding between TNFα and TNFR2. $IC_{50}$ values are reported in nM.

FIG. 1 shows the binding of SBT-002, SBT-004, Fc-TNFR2, TNFα, and hIgG1 to TNFR2. The results indicate that SBT-002 had an $IC_{50}$ of 5.12 nM, SBT-004 had an $IC_{50}$ of 7.88 nM, Fc-TNFR2 had an $IC_{50}$ of 0.23 nM, and TNF-alpha had an $IC_{50}$ of 1.64 nM. The hIgG1 negative control had close to no binding to TNFR2.

Figure 2:
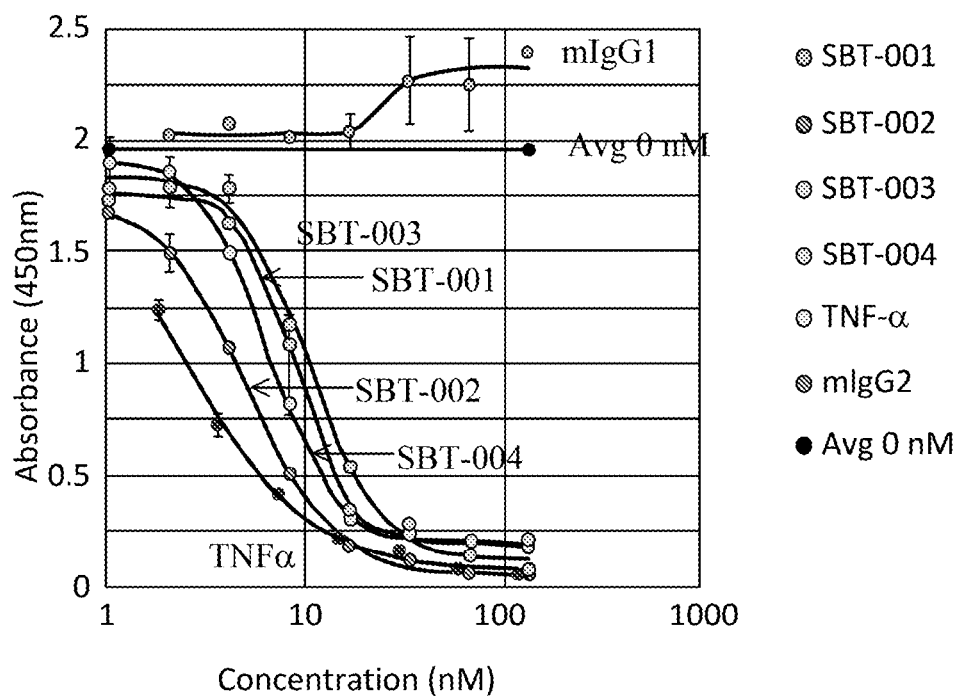
FIG. 2 shows the binding of SBT-001, SBT-002, SBT-003, SBT-004, TNFα, and mouse IgG1 to TNFR2. The results indicate that SBT-001 had an $IC_{50}$ of 9.04 nM, SBT-002 had an $IC_{50}$ of 5.08 nM, SBT-003 had an $IC_{50}$ of 10.48 nM, SBT-004 had an $IC_{50}$ of 6.59, and TNFα had an $IC_{50}$ of 2.61 nM. The mouse IgG1 negative control had close to no binding to TNFR2.

FIG. 2 shows the binding of SBT-001, SBT-002, SBT-003, SBT-004, TNFα, and mouse IgG1 to TNFR2. The results indicate that SBT-001 had an $IC_{50}$ of 9.04 nM, SBT-002 had an $IC_{50}$ of 5.08 nM, SBT-003 had an $IC_{50}$ of 10.48 nM, SBT-004 had an $IC_{50}$ of 6.59, and TNFα had an $IC_{50}$ of 2.61 nM. The mouse IgG1 negative control had close to no binding to TNFR2.

Figure 3:
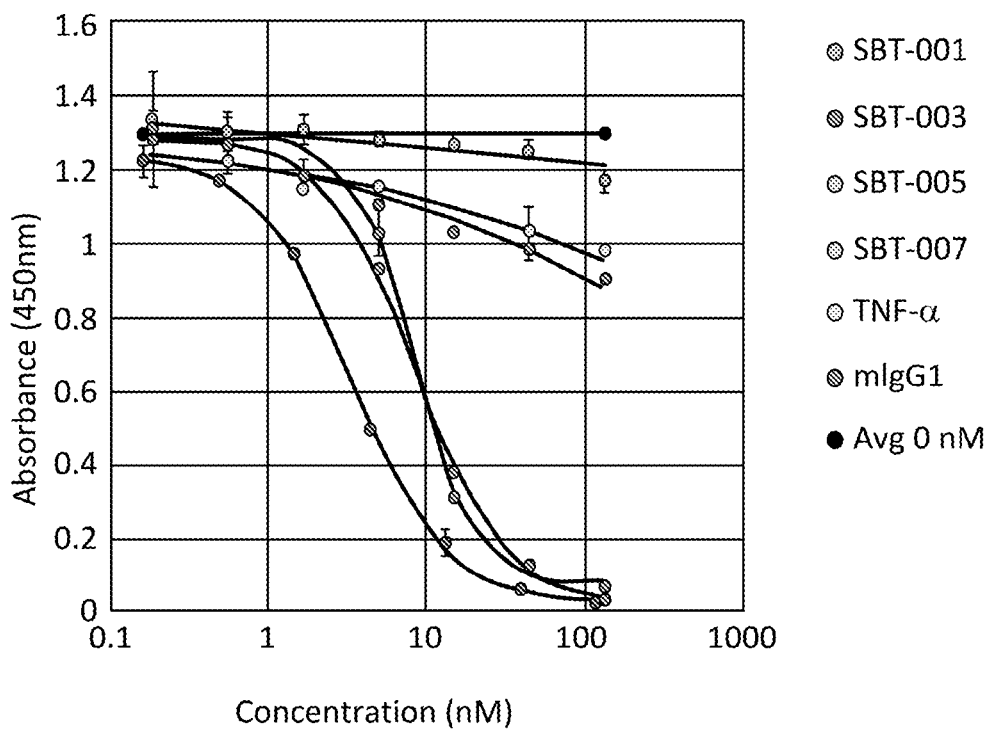
FIG. 3 shows that the biotinylated TNFα binding to the plate-bound soluble TNFR2 was blocked in a concentration-dependent manner by SBT-001, and SBT-003. The negative controls, SBT-005 and SBT-007, did not block binding. $IC_{50}$ values are reported in nM.

FIG. 3 shows that the biotinylated TNFα binding to the plate-bound soluble TNFR2 was blocked in a concentration-dependent manner by SBT-001, and SBT-003. The negative controls, SBT-005 and SBT-007, did not block binding. $IC_{50}$ values are reported in nM.

Example 9

Anti-TNFR2 Antibodies Block TNFα Induced Killing of Jurkat Cells Expressing TNFR2

This example shows anti-TNFR2 antibodies block TNFα induced killing of Jurkat cells that express TNFR2. The anti-TNFR2 antibodies were the same anti-TNFR2 antibodies used in EXAMPLE 7 (SBT-001, SBT-002, SBT-003, and SBT-004). To test the ability of SBT-001, SBT-002, SBT-003, and SBT-004 to block TNFα induced killing of cells, a clonal Jurkat cell line expressing human TNFR2 was used.

A clonal Jurkat cell line expressing human TNFR2 was generated by electroporation of Jurkat E6.1 cells with the expression vector pCMV6-neo containing a cDNA for human TNFR2 cloned into the expression cassette. After growth for 3 days in G418 to select for transfectants, the pool of surviving cells was expanded and cells expressing high levels of human TNFR2 were enriched by FACS cell sorting. The cells expressing high levels of TNFR2 were identified by first incubating with SBT-001 followed by an anti-mouse phycoerythrin (PE) conjugate. The cells were then sorted for those staining brightly for the PE. Single clones were generated by limiting the dilution into 96-well tissue culture plates and screening of aliquots of the cells after expansion using FACS staining as above. Clone H6 was selected as the highest-expressing TNFR2 cell line (FIG. 4), and parental Jurkat cells were used as controls for subsequent experiments.

Figure 4:
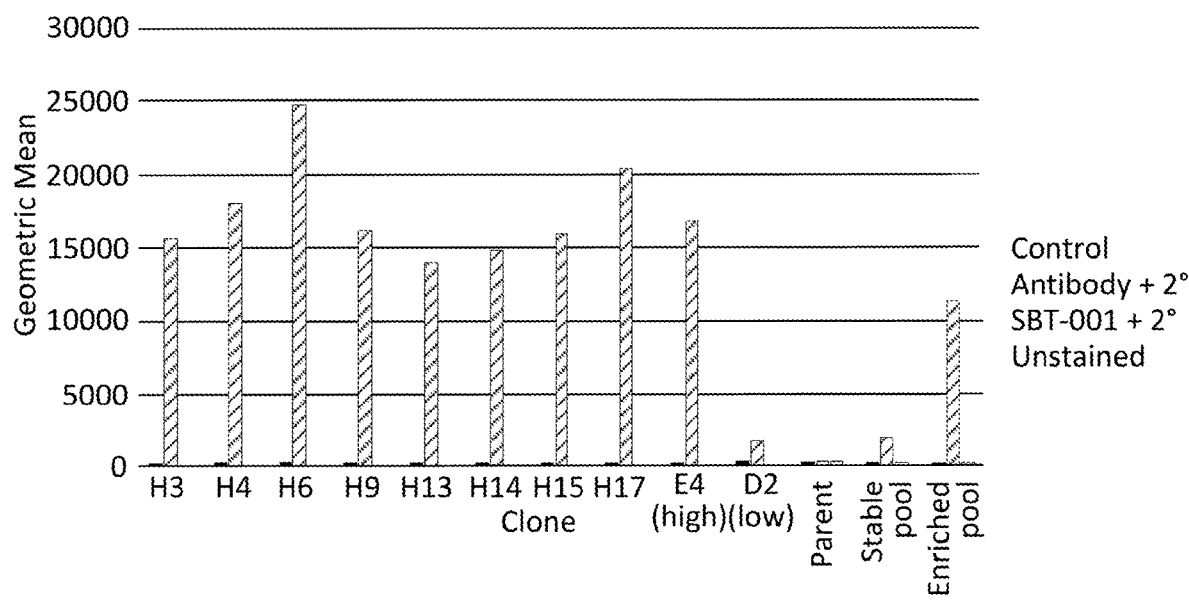
FIG. 4 shows the expression levels of TNFR2 on the different Jurkat cell clones that were isolated. The hatched bars indicate fluorescence from staining with SBT-001 and a secondary antibody, which correspond to the level of TNFR2 expression on the Jurkat cell clones. In contrast, the controls, the black bars and gray bars, indicate staining with a negative control antibody plus a secondary antibody and indicate unstained cells, respectively.

FIG. 4 shows the fluorescence level corresponding to binding of an antibody to different Jurkat cell clones using fluorescent activated cell sorting (FACS). The black bars indicate staining with a negative control antibody plus a fluorescently labeled secondary antibody. The hatched bars indicate the fluorescence of staining with SBT-001 plus a fluorescently labeled secondary antibody. The gray bars indicate unstained cells. This graph shows that neither the unstained control nor the negative control antibody had any fluorescence associated with antibody binding. In contrast, the Jurkat cell clones stained with SBT-001 showed different relative levels of fluorescence, indicating different levels of TNFR2 expression by different Jurkat cell clones.

Figure 5:
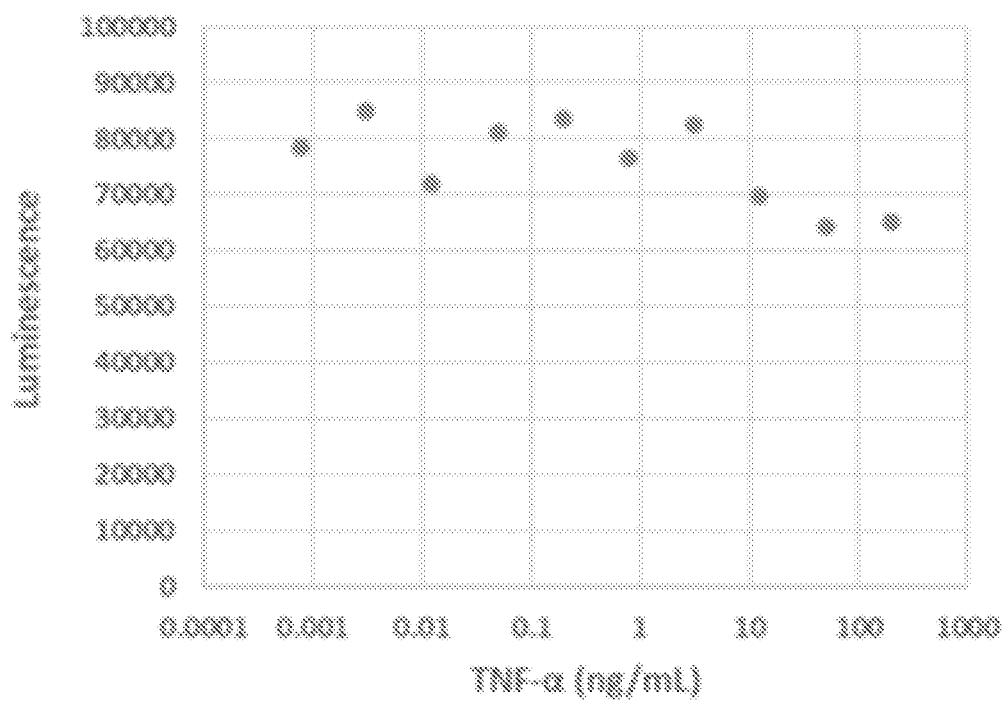
FIG. 5 shows dose titration of TNFα with the parental Jurkat cells, in which the cell viability was unaltered as indicated by luminescence signal using the reagent Cell Titer Glo™.
Figure 6:
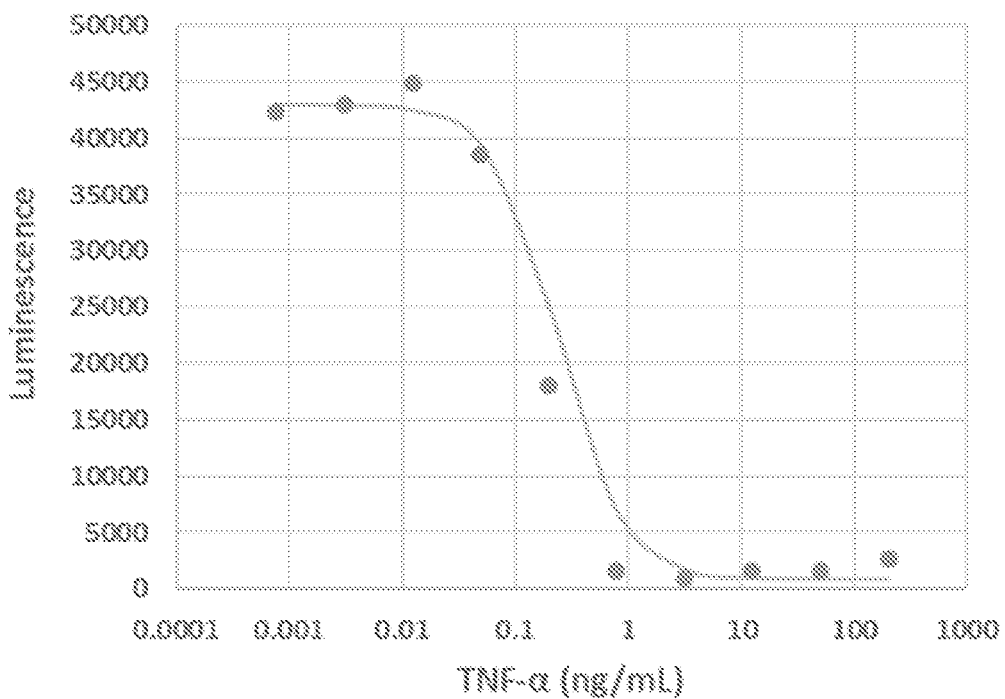
FIG. 6 shows dose titration of TNFα with the clonal H6 Jurkat cells, which demonstrated that clone H6 was greater than 2 logs more sensitive to TNFα addition as monitored by lowered generation of a luminescence signal using the reagent Cell Titer Glo™.
Figure 7:
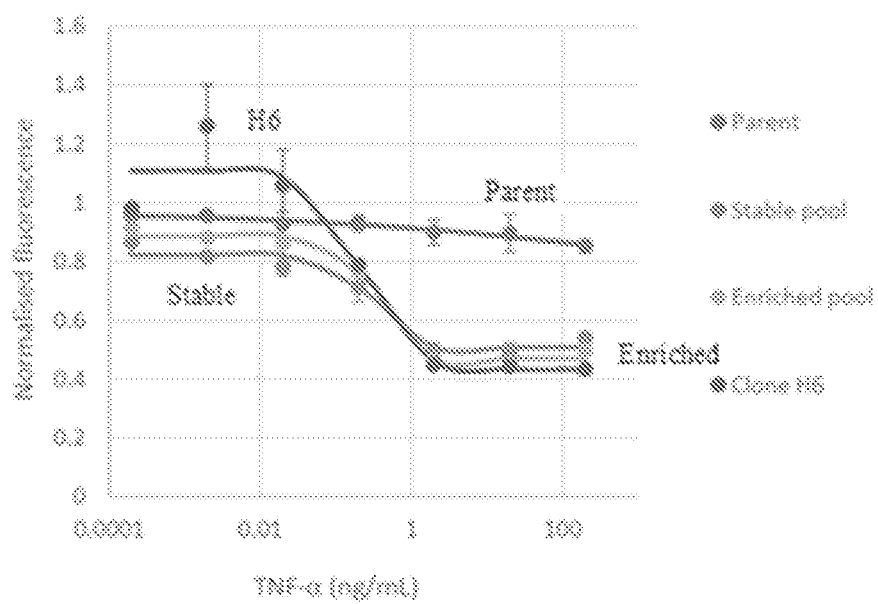
FIG. 7 shows that with increased concentrations of TNFα, the viability of the parent cells remained stable as indicated by a constant fluorescence reading. In contrast, the stable pool, the enriched pool, and H6 clone demonstrated decreased fluorescence due to decreased cell viability.

The clonal H6 Jurkat cells constitutively expressing TNFR2 were sensitive to exogenously applied TNFα, whereas the parental Jurkat cells (i.e., those that did not express TNFR2) were able to maintain unaltered cell viability in the presence of TNFα. This is shown in FIGS. 5 & 6. FIG. 5 shows dose titration of TNFα with the parental Jurkat cells, in which the cell viability was unaltered. In contrast, FIG. 6 shows dose titration of TNFα with the clonal H6 Jurkat cells, which demonstrated that clone H6 was greater than 2 logs more sensitive to TNFα addition as monitored by lowered generation of a luminescence signal using the reagent Cell Titer Glo™. This was difference in cell viability is also shown in FIG. 7, in which cell viability was assessed with Promega CellTiter Glo™ after a 24 hour incubation with TNFα. FIG. 7 shows that with increased concentrations of TNFα, the viability of the parent cells remained stable as indicated by a constant fluorescence reading. In contrast, the stable pool, the enriched pool, and H6 clone demonstrated decreased fluorescence due to decreased cell viability. In the absence of TNFα, SBT-001, SBT-002, SBT-003, and SBT-004 had no effect on the viability of TNFR2-expressing Jurkat cell lines.

Example 10

TNFR2 is not Agonized by Anti-TNFR2 Antibody in a Jurkat Cell Based Assay

This example shows that TNFR2 is not agonized by anti-TNFR2 antibody in a Jurkat cell based assay. The anti-TNFR2 antibodies were the same anti-TNFR2 antibodies used in EXAMPLE 8 (SBT-001, SBT-002, SBT-003, and SBT-004). The same clonal Jurkat cell line expressing human TNFR2 from EXAMPLE 9 was used to test whether TNFR2 is agonized by SBT-001, SBT-002, SBT-003, and SBT-004.

SBT-001, SBT-002, SBT-003, and SBT-004 were added by dose titration to 96-well tissue culture plates containing $10^4$ cells from clonal H6 Jurkat cell line (as described in EXAMPLE 9) in growth media either 2 hours before, or simultaneously with, addition of a constant amount of TNFα (2 ng/mL). This 2 ng/mL concentration of TNFα was sufficient to lower the cell viability by at least 95% as determined by the reduced luminescence signal as shown in FIG. 8.

Figure 8:
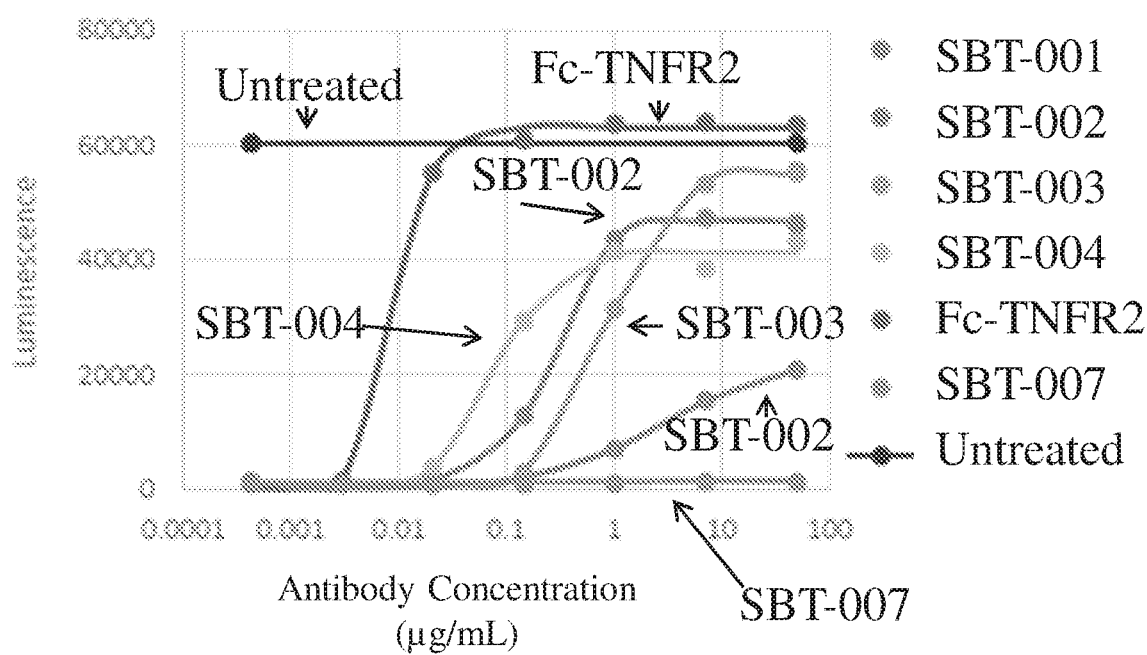
FIG. 8 shows SBT-001, SBT-002, SBT-003, and SBT-004 displayed antagonism of TNFα cellular activity as evidenced by the dose dependent increase in luminescence in the assay when the antibodies were added 2 hours prior to TNFα.
Figure 9:
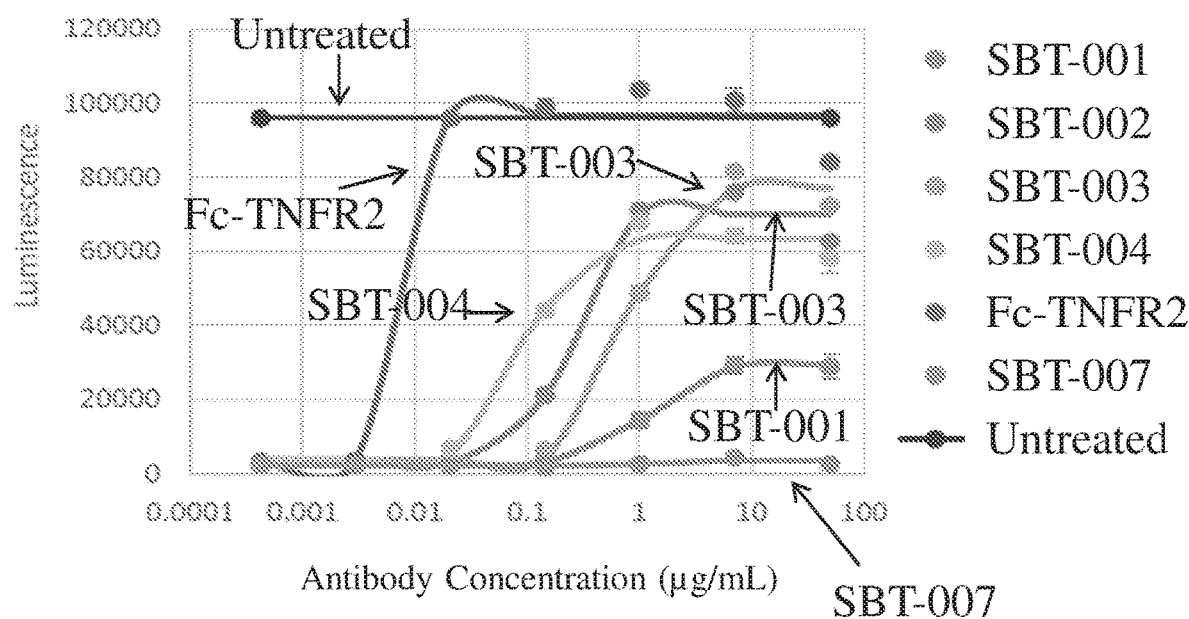
FIG. 9 shows SBT-001, SBT-002, SBT-003, and SBT-004 displayed antagonism of TNFα cellular activity as evidenced by the dose dependent increase in luminescence in the assay when the antibodies were added simultaneously with TNFα.

In FIG. 8, the wells received PBS only (untreated), soluble Fc-TNFR2 (positive control for TNFα blockade) or SBT-007 (an antibody reported to have neither agonist nor antagonist properties) as controls, or SBT-001, SBT-002, SBT-003 or SBT-004. As shown in FIG. 8, SBT-001, SBT-002, SBT-003, and SBT-004 displayed antagonism of TNFα cellular activity as evidenced by the dose dependent increase in luminescence in the assay when the antibodies were added 2 hours prior to TNFα. The calculated $IC_{50}$ for the antagonists are displayed in the table. FIG. 9 shows the same experiment except that the antibodies were added simultaneously with TNFα. The $IC_{50}$ values are shown in TABLE 7 below.

TABLE 7

| Antibody | IC$_{50}$ (µg/mL) (with pre-incubation) | IC$_{50}$ (µg/mL) (without pre-incubation) |
|---|---|---|
| SBT-001 | 3.03 | 2.53 |
| SBT-002 | 0.26 | 0.12 |
| SBT-003 | 0.89 | 0.88 |
| SBT-004 | 0.09 | 0.1 |
| Fc-TNFR2 | 0.0125 | 0.0115 |

IC$_{50}$ for binding to TNFR2

Figure 10:
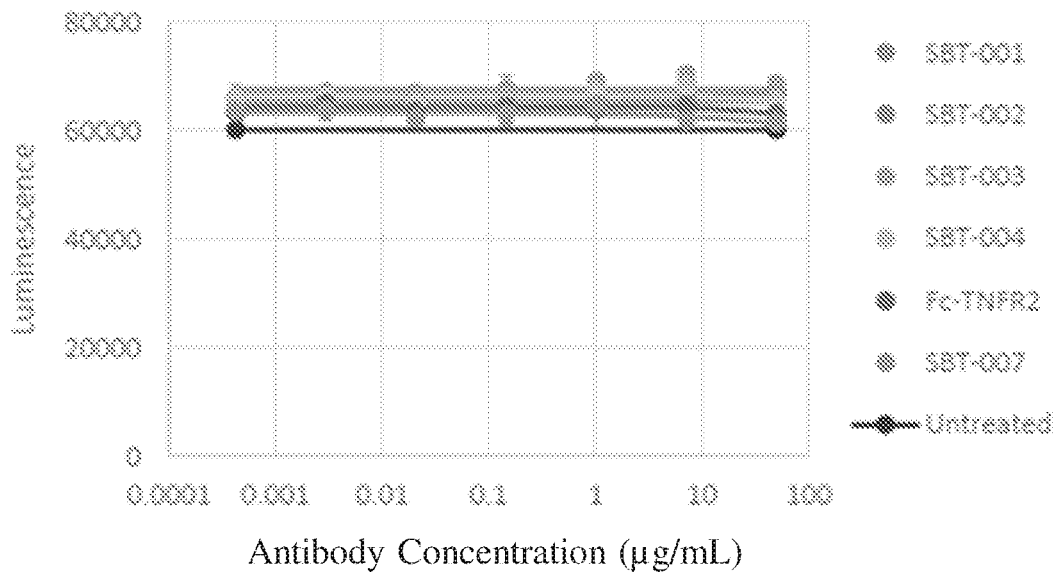
FIG. 10 shows a control experiment where the cells were not incubated with TNFα, and only with the antibodies. The luminescence signal remained constant indicating that the cell remained viable throughout the course of the experiment.

FIG. 10 shows a control experiment where the cells were not incubated with TNFα, and only with the antibodies. The luminescence signal remained constant indicating that the cell remained viable throughout the course of the experiment.

Example 11

Generation of Chimeric Anti-TNFR2 Antibody with a Human IgG1 Fc Domain

This example shows a method for generating a chimeric anti-TNFR2 antibody with a human IgG1 Fc domain. Four different anti-TNFR2 antibodies were purified by size exclusion chromatography. These four antibodies were mouse SBT-001, mouse SBT-002, mouse SBT-003, and rat SBT-004. SBT-001 was comprised of the heavy chain variable region SEQ ID NO: 1 paired with the light chain variable region SEQ ID NO: 2. SBT-002 was comprised of the heavy chain variable region SEQ ID NO: 3 and the light chain variable region SEQ ID NO: 4. SBT-003 was comprised of the heavy chain variable region SEQ ID NO: 5 and the light chain variable region SEQ ID NO: 6. SBT-004 was comprised of the heavy chain variable region SEQ ID NO: 7 and the light chain variable region SEQ ID NO: 8 or the light chain variable region SEQ ID NO: 9.

The variable heavy chains of SBT-001, SBT-002, SBT-003, and SBT-004 were genetically fused to a human IgG1 Fc domain to produce the heavy chain of chimeric SBT-001 (chSBT-001), chimeric SBT-002 (chSBT-002), chimeric SBT-003 (chSBT-003), and chimeric SBT-004 (chSBT-004) and chimeric SBT-004b (chSBT-004b) (the same heavy chain is used for both chSBT-004 and chSBT-004b, but chSBT-004 was comprised of the light chain variable region SEQ ID NO: 8 and chSBT-004b was comprised of the light chain variable region SEQ ID NO:9), respectively. These DNA constructs were cloned into the pcDNA3.1(+) expression vector. The heavy chain vector constructs together with the respective light chain vector constructs were transiently co-expressed in the CHO-S cell line to generate the chimeric antibodies with human IgG1 Fc domains, chSBT-001, chSBT-002, chSBT-003, chSBT-004, and chSBT-004b. The protein from the CHO-S supernatant was purified to homogeneity using protein A column on GE AKTA Pure™ system and confirmed for purity using SEC.

Example 12

Chimeric Anti-TNFR2 Antibody Binds to Human TNFR2 and Cynomolgus TNFR2 Extracellular Domain with Similar Affinity as Parental Anti-TNFR2 Antibody This example shows that chimeric anti-TNFR2 antibody binds to human TNFR2 and cynomolgus TNFR2 extracellular domain (ECD) with similar affinity as its parent anti-TNFR2 antibody. The chimeric antibodies were chSBT-001, chSBT-002, chSBT-003, chSBT-004, and chSBT-004b as described in EXAMPLE 11, and their corresponding parental antibodies were SBT-001, SBT-002, SBT-003, and SBT-004, as described in EXAMPLE 8.

Analysis of binding to the human and cynomolgus TNFR2 ECD was performed using an Octet Red 96 Instrument™ (ForteBio). The SBT-001, SBT-002, SBT-003, and SBT-004, and chSBT-001, chSBT-002, chSBT-003, chSBT-004, and chSBT-004b were immobilized on anti-mouse Fc, anti-rat, or anti-human Fc bio sensors, and incubated with varying concentration of monomeric human and cynomolgus TNFR2 ECD ranging from 1.2 nM to 1 µM in PBS. The experiments were performed using five steps: (1) baseline acquisition (60 s); (2) antibody loading on to anti-human or anti-mouse Fc biosensors (120 s); (3) second baseline acquisition (60 s); (4) association of interacting monomeric human or cynomolgus TNFR2 ECD protein for k$_{on}$ measurement (120 s); and (5) dissociation of interacting monomeric human or cynomolgus TNFR2 ECD for k$_{off}$ measurement (240-3600 s).

The interacting monomeric human or cynomolgus ECD was used at 5-6 concentrations of a 3-fold concentration series. The data were analyzed using Octet Data Analysis Software 9.0™ (ForteBio) and fit to the 1:1 binding model. The equilibrium dissociation constants (K$_d$) were calculated by the ratio of k$_{on}$ to k$_{off}$. The data are shown in TABLE 8 below. All the chimeric anti-TNFR2 antibodies had similar binding (K$_d$) as the parental anti-TNFR2 antibodies to monomeric human and cynomolgus TNFR2 ECD.

TABLE 8

Antibody K$_d$ for Human TNFR2 ECD and Cynomolgus (Cyno) TNFR2 ECD

| Antibody | Human TNFR2 K$_d$ | Cyno TNFR2 K$_d$ |
|---|---|---|
| SBT-001 | 2.7 nM | 53.1 nM |
| chSBT-001 | 1.8 nM | 58.3 nM |
| SBT-002 | 1.3 nM | 0.44 nM |
| chSBT-002 | 0.8 nM | 0.62 nM |
| SBT-003 | 1.2 nM | Weak, µM range |
| chSBT-003 | 0.25 nM | 0.47 µM |
| SBT-004 | 1.8 nM | undetermined |
| chSBT-004 | 3.6 nM | 3.4 nM |
| chSBT-004b | 2.8 nM | 7.9 nM |

Example 13

Generation of Chimeric Anti-TNFR2 Antibody with an Fc Domain that does not Bind to a Human Fcγ Receptor This example shows a method for generating a chimeric anti-TNFR2 antibody with a human Fcγ receptor (FcγR) binding null Fc domain. Four different anti-TNFR2 antibodies were purified by size exclusion chromatography. These four antibodies were mouse SBT-001, mouse SBT-002, mouse SBT-003, and rat SBT-004. SBT-001 was comprised of the heavy chain variable region SEQ ID NO: 1 paired with the light chain variable region SEQ ID NO: 2. SBT-002 was comprised of the heavy chain variable region SEQ ID NO: 3 and the light chain variable region SEQ ID NO: 4. SBT-003 was comprised of the heavy chain variable region SEQ ID NO: 5 and the light chain variable region SEQ ID NO: 6. SBT-004 was comprised of the heavy chain variable region SEQ ID NO: 7 and the light chain variable region SEQ ID NO: 8 or the light chain variable region SEQ ID NO: 9.

The variable heavy chains of SBT-001, SBT-002, SBT-003, and SBT-004 were genetically fused to a human IgG1 Fc domain that was null for binding to a FcγR to produce chimeric SBT-001 Fc null (chSBT-001n), chimeric SBT-002 Fc null (chSBT-002n), chimeric SBT-003 Fc null (chSBT-003n), and chimeric SBT-004 Fc null (chSBT-004n), respectively. The human IgG1 null Fc domain comprised the following mutations: L234A, L235A, G237A, and K322A. These DNA constructs were cloned into the pcDNA3.1(+) expression vector. The heavy chain vector constructs containing the Fc null mutations together with the respective light chain vector constructs were transiently co-expressed in the CHO-S cell line to generate chimeric antibodies with human IgG1 null Fc domains. The protein from the CHO-S supernatant was purified to homogeneity using protein A column on GE AKTA Pure™ system and confirmed for purity using SEC.

For each chimeric antibody, human FcγR interaction analysis was independently performed using an Octet Red 96 ™ instrument. For human FcγRI and FcγRIIA interactions, the chimeric antibody was immobilized on anti-human Fc biosensors and incubated with varying concentration of monomeric FcγR ranging from 1.2 nM to 1 µM in PBS. The experiments were performed using five steps: (1) baseline acquisition (60 s); (2) chimeric antibody loading onto anti-human Fc biosensor (120 s); (3) second baseline acquisition (60 s); (4) association of interacting protein for $k_{on}$ measurement (120 s); and (5) dissociation of interacting FcγR for $k_{off}$ measurement (300 s). The interacting monomeric FcγR was used at 5-6 concentrations of a 3-fold concentration series. The data were analyzed using Octet Data Analysis Software 9.0 (ForteBio)™ and fit to the 1:1 binding model. Equilibrium dissociation constants ($K_D$) were calculated by the ratio of $k_{on}$ to $k_{off}$. For human FcγRIIB/C, FcγRIIIA F158, FcγRIIIA V158 and FcγRIIIB interaction studies, the proteins were immobilized on anti-His tag biosensors and incubated with varying concentrations of the chimeric antibody ranging from 0.04 µM to 8 µM. The experiment was performed using five steps: (1) Baseline acquisition (30 s); (2) human FcγRs loading to the anti-His tag biosensor (120 s); (3) second baseline acquisition (30 s); (4) association of interacting mAbs for $k_{on}$ measurement (30 s); and (5) dissociation of interaction mAbs for $k_{off}$ measurement (30 s). The interacting monomeric FcγR was used at 4 concentrations of a 2-fold concentration series. The data were analyzed using Octet Data Analysis Software 9.0 (ForteBio)™ and fit to the avidity binding model. This fitting model generated two $K_d$s and only the predominant one was reported in the table below. Equilibrium dissociation constants ($K_d$) were calculated by the ratio of kon to koff. The chSBT-002n, chSBT-003n, and chSBT-004n did not bind to all the 6 different FcγRs unlike the parental antibodies where there was measurable binding observed for SBT-002 and SBT-003 to FcγRII1 and FcγRIIB/C and SBT-004 where is measurable binding to all the 6 different FcγR.

TABLE 9

$K_d$ of Chimeric Antibody Binding to FcγR.

| Antibody | Human TNFR2 $K_d$ (1-1) (nM) | FcγRI $K_d$ (1-1) (nM) | FcγRIIA $K_d$ (1-1) (nM) | FcγRIIB/C $K_d$ (avidity) (µM) | FcγRIIIA F158 $K_d$ (avidity) (µM) | FcγRIIIA V158 $K_d$ (avidity) (µM) | FcγRIIIB $K_d$ (avidity) (µM) |
|---|---|---|---|---|---|---|---|
| chSBT-002n | 2.5 | NB | NB | NB | NB | NB | NB |
| chSBT-003n | 1.0 | NB | NB | NB | NB | NB | NB |
| chSBT-004n | 5.0 | NB | NB | NB | NB | NB | NB |
| SBT-002 | 1.3 | NB | 330 | 0.29 | NB | NB | NB |
| SBT-003 | 1.2 | NB | 296 | 0.02 | NB | NB | NB |
| SBT-004 | 1.1 | 0.07 | 0.02 | 0.17 | 0.33 | 0.54 | 0.23 |

NB = No Binding

Example 14

Chimeric Anti-TNFR2 Antibody Blocks TNFα Binding to Human TNFR2 and Cynomolgus TNFR2

This example shows that chimeric anti-TNFR2 antibody blocks TNFα binding to human TNFR2 and cynomolgus TNFR2. The chimeric antibodies were chSBT-002, chSBT-003, and chSBT-004 as described in EXAMPLE 11, as well as a chimeric antibody produced by the same method as described in EXAMPLE 11 in which the heavy chain variable region SEQ ID NO: 7 and the light chain variable region SEQ ID NO:10 of were used produce chSBT-004b.

The chimeric antibodies were purified to >97% dimer species purity by preparative size-exclusion chromatography (SEC) using a GEHealthcare HiLoad™ 16/60 Superdex™ 200 pg preparative SEC column using 1×PBS as mobile phase.

Competition ELISA was used to evaluate the ability of chSBT-002, chSBT-003, chSBT-004 and SBT-004b to block TNFα from binding to TNFR2. Unbiotinylated TNFα and SBT-002, the parental antibody of chSBT-002, were used as positive controls. SBT-007, an antibody that binds to TNFR2 but does not block TNFα binding, and no antibody were used as negative controls. Soluble human TNFR2 (Sino Biological, 10417-H08H) or cynomolgus TNFR2 (Sino Biological, 90102-C08H) was coated on Nunc-Immuno™ plates at 0.1 µg/ml, 0.5 ug/ml, 1 µg/ml, and 5 µg/ml. TNFα was biotinylated using an Innova Lightning-Link™ kit (Innova, 704-0010). Biotinylated TNFα was titrated from 4 ug/ml in a 3-fold dilution series. Bound TNFα-biotin was detected using a streptavidin-HRP conjugate. Plates were developed using TMB and stopped with 3 M HCl. The level of bound TNFα was determined by reading absorbance at 450 nM.

Figure 11:
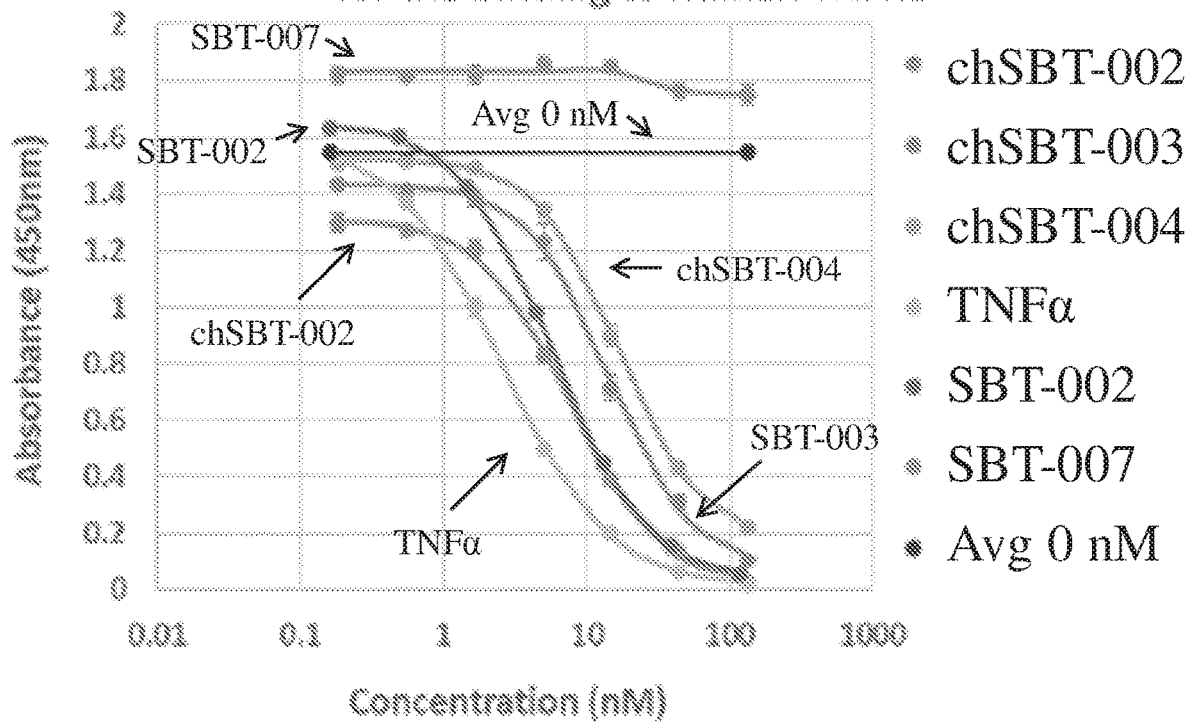
FIG. 11 shows that the biotinylated TNFα binding to the plate-bound soluble human TNFR2 was blocked in a concentration-dependent manner by chSBT-002, chSBT-003, and chSBT-004. The positive controls, TNFα and SBT-002, blocked biotinylated TNFα binding to the plate-bound soluble human TNFR2. The negative controls, SBT-007 and no antibody (Avg 0 nM), did not block binding.
Figure 12:
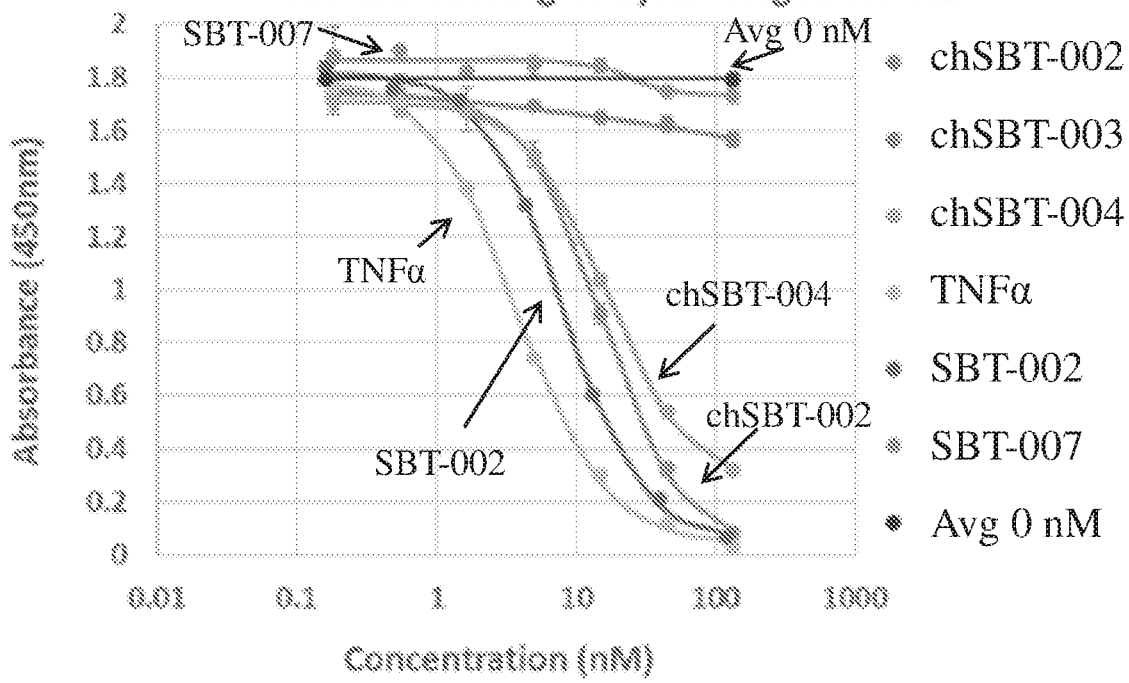
FIG. 12 shows that the biotinylated TNFα binding to the plate-bound soluble cynomolgus TNFR2 was blocked in a concentration-dependent manner by chSBT-002 and chSBT-004. However, biotinylated TNFα binding to the plate-bound soluble cynomolgus TNFR2 was not blocked in a concentration-dependent manner by chSBT-003. The positive controls, TNFα and SBT-002, blocked biotinylated TNFα binding to the plate-bound soluble human TNFR2. The negative controls, SBT-007 and no antibody (Avg 0 nM), did not block binding.
Figure 13:
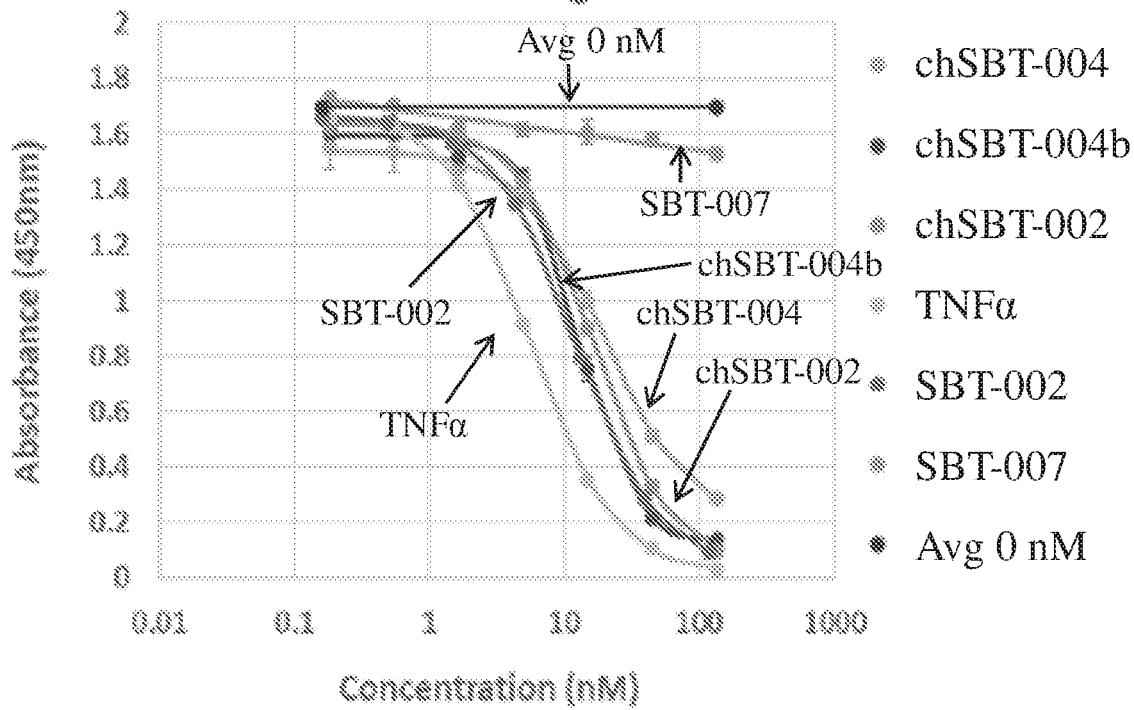
FIG. 13 shows that the biotinylated TNFα binding to the plate-bound soluble human TNFR2 was blocked in a concentration-dependent manner by chSBT-004, chSBT-004b, and chSBT-002. The positive controls, TNFα and SBT-002, blocked biotinylated TNFα binding to the plate-bound soluble human TNFR2. The negative controls, SBT-007 and no antibody (Avg 0 nM), did not block binding. $IC_{50}$ values are reported in nM.
Figure 14:
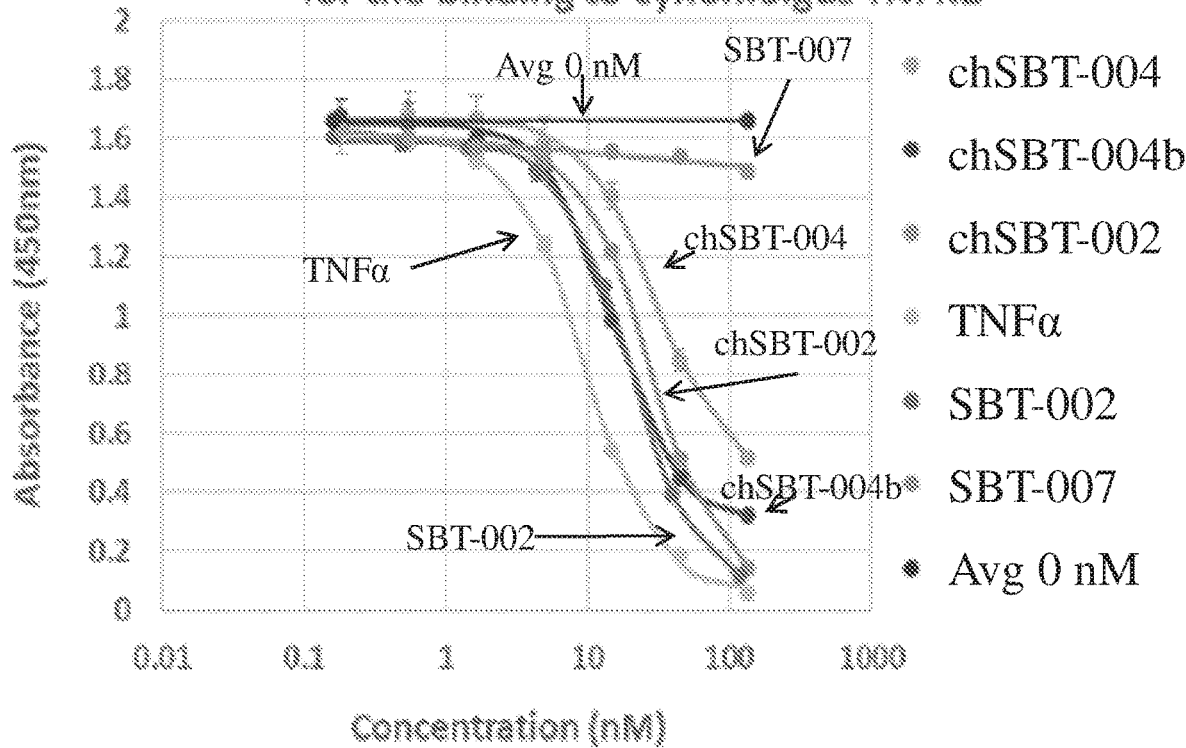
FIG. 14 shows that the biotinylated TNFα binding to the plate-bound soluble cynomolgus TNFR2 was blocked in a concentration-dependent manner by chSBT-004, chSBT-004b, and chSBT-002. The positive controls, TNFα and SBT-002, blocked biotinylated TNFα binding to the plate-bound soluble human TNFR2. The negative controls, SBT-007 and no antibody (Avg 0 nM), did not block binding. $IC_{50}$ values are reported in nM.

FIG. 11 shows that the biotinylated TNFα binding to the plate-bound soluble human TNFR2 was blocked in a concentration-dependent manner by chSBT-002, chSBT-003, and chSBT-004. The positive controls, TNFα and SBT-002, blocked biotinylated TNFα binding to the plate-bound soluble human TNFR2. The negative controls, SBT-007 and no antibody (Avg 0 nM), did not block binding. FIG. 12 shows that the biotinylated TNFα binding to the plate-bound soluble cynomolgus TNFR2 was blocked in a concentration-dependent manner by chSBT-002 and chSBT-004. However, biotinylated TNFα binding to the plate-bound soluble cynomolgus TNFR2 was not blocked in a concentration-dependent manner by chSBT-003. The positive controls, TNFα and SBT-002, blocked biotinylated TNFα binding to the plate-bound soluble human TNFR2. The negative controls, SBT-007 and no antibody (Avg 0 nM), did not block binding. FIG. 13 shows that the biotinylated TNFα binding to the plate-bound soluble human TNFR2 was blocked in a concentration-dependent manner by chSBT-004, chSBT-004b, and chSBT-002. The positive controls, TNFα and SBT-002, blocked biotinylated TNFα binding to the plate-bound soluble human TNFR2. The negative controls, SBT-007 and no antibody (Avg 0 nM), did not block binding. $IC_{50}$ values are reported in nM. FIG. 14 shows that the biotinylated TNFα binding to the plate-bound soluble cynomolgus TNFR2 was blocked in a concentration-dependent manner by chSBT-004, chSBT-004b, and chSBT-002. The positive controls, TNFα and SBT-002, blocked biotinylated TNFα binding to the plate-bound soluble human TNFR2. The negative controls, SBT-007 and no antibody (Avg 0 nM), did not block binding. $IC_{50}$ values are reported in nM. The below TABLE 10 and TABLE 11 show the average relative $IC_{50}$ values for chSBT-002, chSBT-003, chSBT-004, chSBT-004b, SBT-002, SBT-007, and TNFα binding to human TNFR2 and cynomolgus TNFR2, respectively.

TABLE 10

Average Relative $IC_{50}$ Values for Binding to human TNFR2

| Antibody | Average Relative IC50 (nM) |
|---|---|
| chSBT-002 | 2.91 |
| chSBT-003 | 5.33 |
| chSBT-004 | 5.07 |
| chSBT-004b | 2.93 |
| TNFα | 1.00 |
| SBT-002 | 2.19 |
| SBT-007 | — |

TABLE 11

Average Relative $IC_{50}$ Values for Binding to cynomolgus TNFR2

| Antibody | Average Relative IC50 (nM) |
|---|---|
| chSBT-002 | 3.38 |
| chSBT-003 | — |
| chSBT-004 | 3.64 |
| chSBT-004b | 1.56 |
| TNFα | 1.00 |
| SBT-002 | 1.98 |
| SBT-007 | — |

Example 15

Chimeric Anti-TNFR2 Antibody Block TNFR2-Mediated TNFα-Induced Cell Death in a Jurkat Cell Based Assay This example shows that chimeric anti-TNFR2 antibody antagonized TNFR2 activation by TNFα in a Jurkat cell based assay. The chimeric antibodies were chSBT-002, chSBT-003, and chSBT-004 as described in EXAMPLE 11, as well as a chimeric antibody produced by the same method as described in EXAMPLE 7 in which the heavy chain variable region SEQ ID NO: 7 and the light chain variable region SEQ ID NO: 9 of were used produce chSBT-004b.

The clonal H6 Jurkat cell line as described in EXAMPLE 10 was used, and cell viability was assessed with Promega CellTiter Glo™. chSBT-002, chSBT-003, chSBT-004, and chSBT-004b were added by dose titration along with a constant amount of TNFα (2 ng/ml) to 96-well tissue culture plates containing $10^4$ cells from the clonal H6 Jurkat cell line in growth media followed by a 24 hour incubation prior to performing the cell viability assay. Cells that were not cultured with TNFα (untreated) served as a cell viability baseline, and addition of Fc-TNFR2 or a parent antibody (SBT-002, SBT-003, SBT-004, or SBT-004b) was used as a positive control. An antibody that does not interfere with TNFα binding to TNFR2, SBT-007, was used as a negative control.

Figure 15:
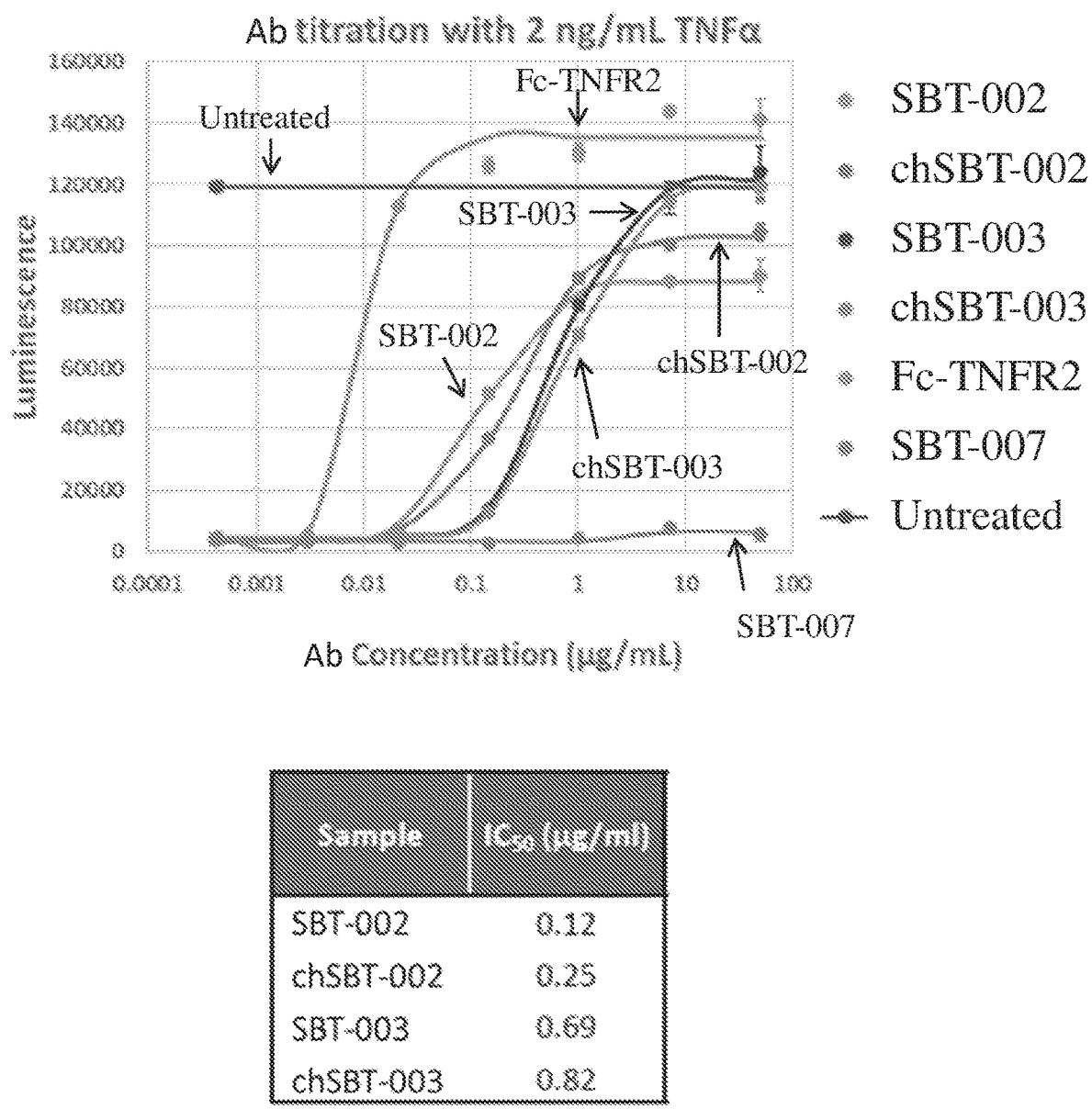
FIG. 15 shows chSBT-002 and chSBT-003 were antagonists of TNFR2 activation by TNFα as evidenced by the increase in luminescence in the assay when the dose of added antibodies was increased. SBT-002, SBT-003, and Fc-TNFR2 also showed a dose dependent increase in luminescence. Luminescence of untreated cells (cells not cultured with TNFα) were used as the viability baseline. SBT-007 did not show a dose dependent increase in luminescence.
Figure 16:
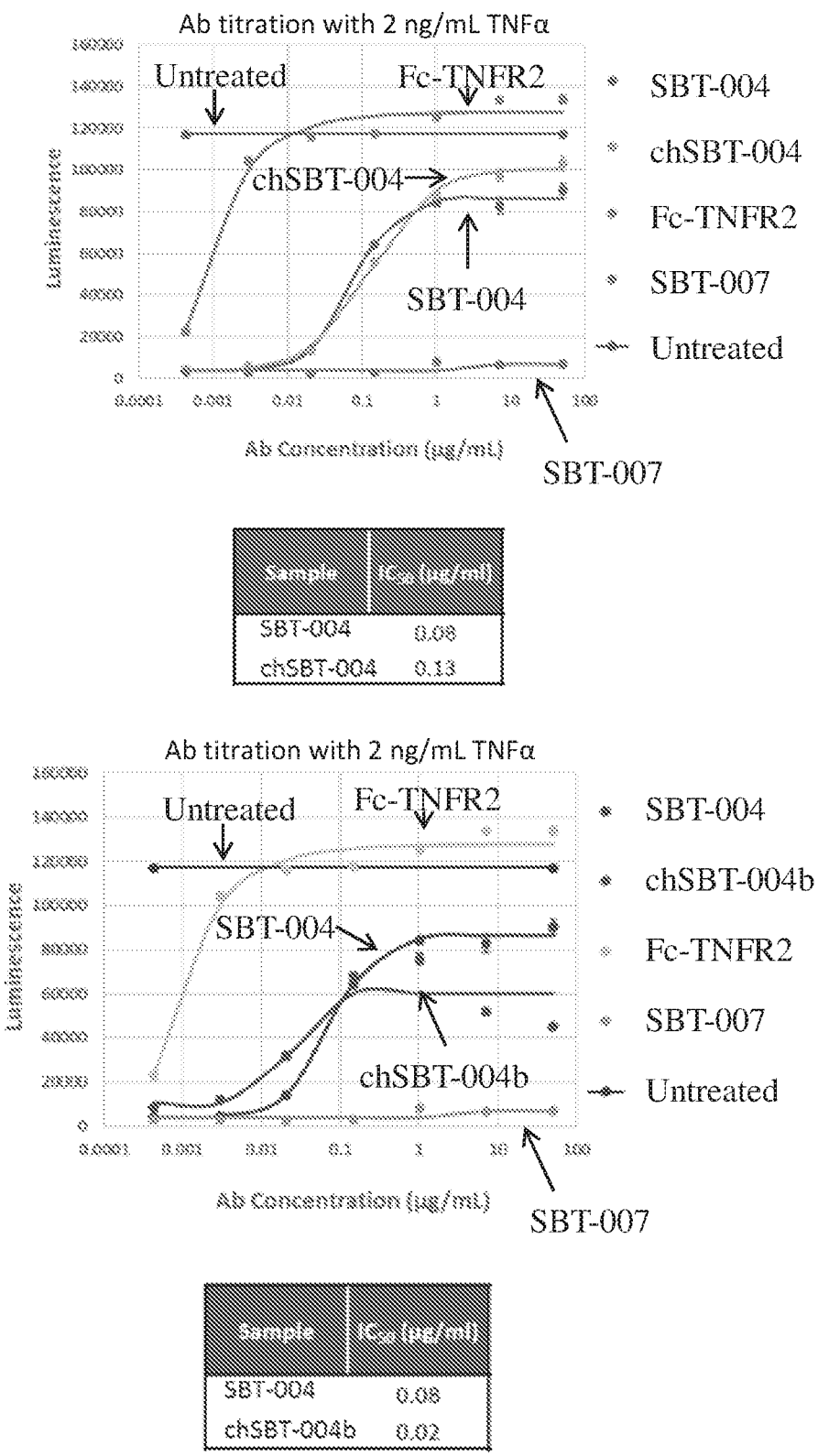
FIG. 16 shows chSBT-004 and chSBT-004b were antagonists of TNFR2 activation by TNFα as evidenced by the dose dependent increase in luminescence in the assay when the antibody was added. SBT-004, and Fc-TNFR2 also showed a dose dependent increase in luminescence. SBT-007 did not show a dose dependent increase in luminescence. Luminescence of untreated cells (cells not cultured with TNFα) were used as the viability baseline.

FIG. 15 shows chSBT-002 and chSBT-003 were antagonists of TNFR2 activation by TNFα as evidenced by the increase in luminescence in the assay when the dose of added antibodies was increased. SBT-002, SBT-003, and Fc-TNFR2 also showed a dose dependent increase in luminescence. Luminescence of untreated cells were used as the viability baseline. SBT-007 did not show a dose dependent increase in luminescence. FIG. 16 shows chSBT-004 and chSBT-004b were antagonists of TNFR2 activation by TNFα as evidenced by the dose dependent increase in luminescence in the assay when the antibody was added. SBT-004, and Fc-TNFR2 also showed a dose dependent increase in luminescence. SBT-007 did not show a dose dependent increase in luminescence. Luminescence of untreated cells were used as the viability baseline.

Example 16

Chimeric Anti-TNFR2 Antibodies Bind to Subsets of Cynomolgus Peripheral $CD4^+$ T Cells and $CD8^+$ T Cells This example shows that chimeric anti-TNFR2 antibodies bind to TNFR2 on cynomolgus $CD4^+$ T cells and $CD8^+$ T cells. The chimeric antibodies were chSBT-003, chSBT-002, chSBT-004, and chSBT-004b. Flow cytometry was used to show that these chimeric anti-TNFR2 antibodies bound to cynomolgus TNFR2 on a $CD4^+$ T cell population and a $CD8^+$ T cell population in cynomolgus whole blood cells.

Figure 17:
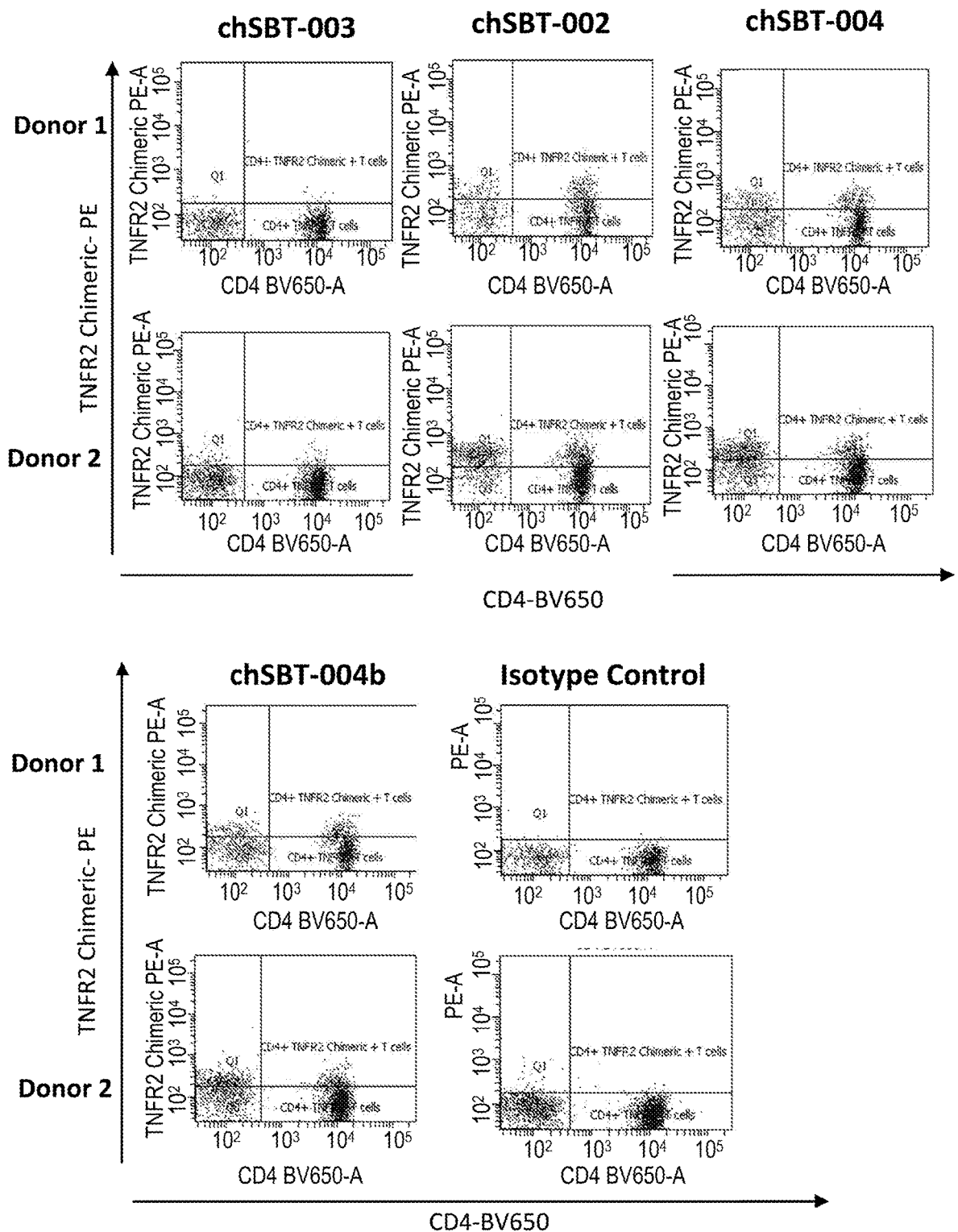
FIG. 17 shows chSBT-002 bound the highest percentage of CD4$^+$ T cells, followed by chSBT-004 and chSBT-004b. In contrast, chSBT-003 had little binding CD4$^+$ T cell activity compared to the isotype control, which was an antibody that targets a growth factor receptor expressed on epithelial cells.
Figure 18:
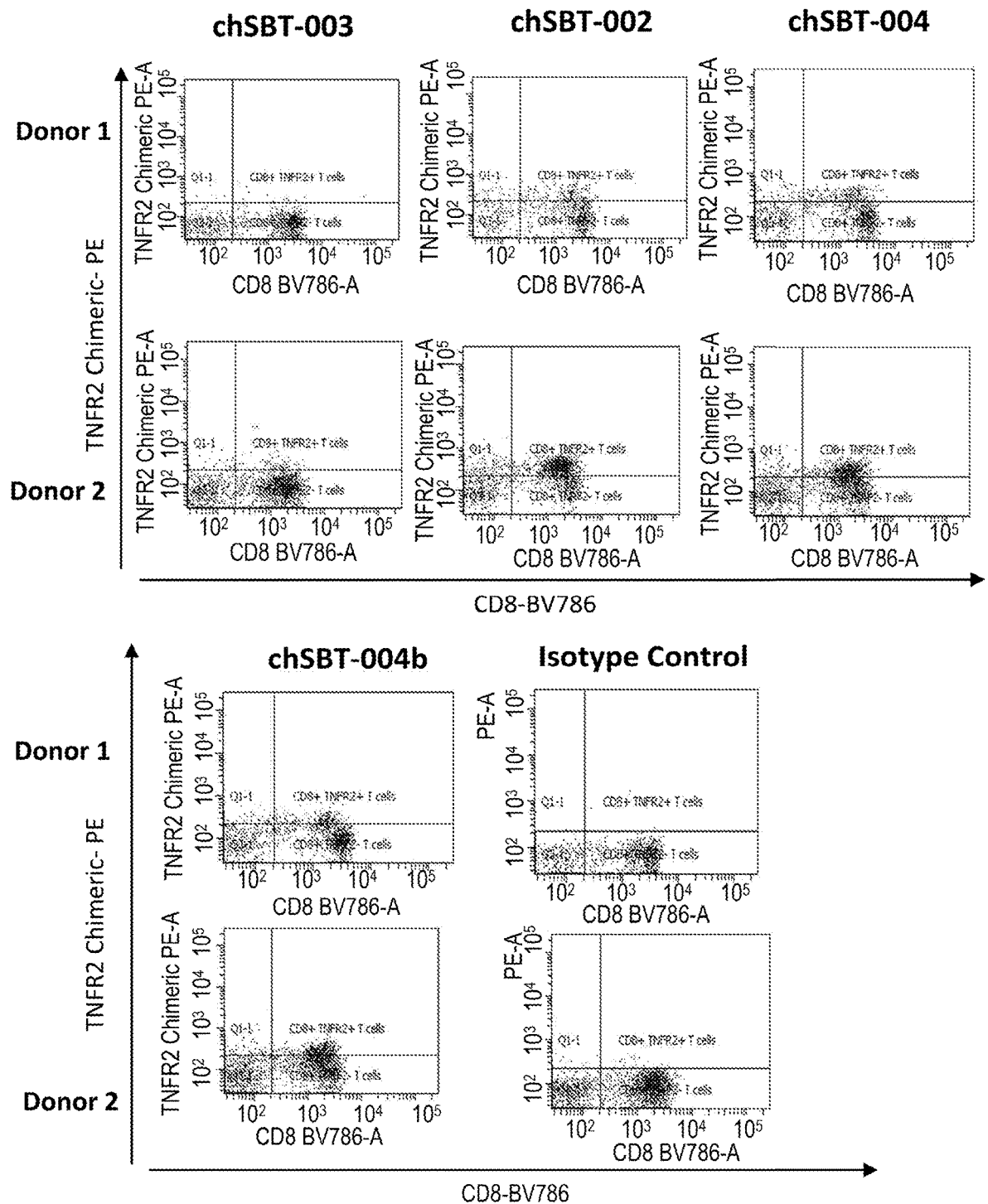
FIG. 18 shows chSBT-002 bound the highest percentage of CD8$^+$ T cells, followed by chSBT-004 and chSBT-004b. In contrast, chSBT-003 had little binding CD8$^+$ T cell activity compared to the isotype control, which was an antibody that targets a growth factor receptor expressed on epithelial cells.

Cynomolgus peripheral blood mononuclear cells (PBMCs) from two independent donors were isolated by diluting whole blood (SNBL USA) 1:1 in PBS (Lonza), layering over Ficoll-Paque Plus (GE Healthcare), and centrifuging for 35 minutes at 400×g. The PBMC fraction was removed, washed 3 times in 2% FBS PBS and counted. $0.3 \times 10^6$ PBMC were resuspended in Fixable Viability Stain 575V (BD) diluted 1:1000 in PBS and incubated for 10 minutes. PBMC were then washed twice in PBS to remove residual viability stain, resuspended in Horizon Brilliant Stain Buffer (BD) with 10 uL per test of human Fc receptor binding inhibitor (eBioscience), and incubated on ice for 20 minutes to block Fc receptors. Fluorochrome-conjugated antibodies to CD3-BV510 clone SP34-2 (BD), CD4-BV650 clone L200 (BD) and CD8-BV786 clone RPA-T8 (BD) or isotype controls were added to PBMCs at a final dilution of 1:50 together with chSBT-003, chSBT-002, chSBT-004, chSBT-004b, or isotype control, which was an antibody that targets a growth factor receptor expressed on epithelial cells, at 10 ug/mL. PBMC were incubated 20 minutes on ice and then washed three times with 2% FBS PBS. To visualize TNFR2 chimeric antibody binding, PBMC were resuspended in goat anti-human Fc-PE F(ab')$_2$ secondary reagent (Jackson ImmunoResearch) diluted 1:200 in 2% FBS PBS and incubated on ice for 20 minutes. Cells were then washed three times in 2% FBS PBS and resuspended in 200 uL 2% FBS PBS for flow cytometry analysis using a BD FACS Celesta instrument and FACS Diva software. T cells were analyzed for chimeric TNFR2 binding by gating on viable cells defined as lymphocytes using forward and side scatter and as T cells by anti-CD3 staining. CD4$^+$ and CD8$^+$ subsets were identified using commercial specific antibody conjugates. FIG. 17 shows chSBT-002 bound the highest percentage of CD4$^+$ T cells, followed by chSBT-004 and chSBT-004b. In contrast, chSBT-003 had little binding CD4$^+$ T cell activity compared to the isotype control, which was an antibody that targets a growth factor receptor expressed on epithelial cells. FIG. 18 shows chSBT-002 bound the highest percentage of CD8$^+$ T cells, followed by chSBT-004 and chSBT-004b. In contrast, chSBT-003 had little binding CD8$^+$ T cell activity compared to the isotype control, which was an antibody that targets a growth factor receptor expressed on epithelial cells. TABLE 12 below is a summary of antibody binding to CD4$^+$ antibody$^+$ T cells and CD8$^+$ antibody$^+$ T cells.

TABLE 12

Percentage of CD4$^+$ antibody$^+$ (ab$^+$) cells

| Antibody | % CD4$^+$ ab$^+$ Donor 1 | % CD4$^+$ ab$^+$ Donor 2 | % CD8$^+$ ab$^+$ Donor 1 | % CD8$^+$ ab$^+$ Donor 2 |
|---|---|---|---|---|
| chSBT-003 | 0.7 | 1.2 | 0.6 | 2.1 |
| chSBT-002 | 9.0 | 14.1 | 9.5 | 29.0 |
| chSBT-004 | 10.2 | 7.6 | 11.2 | 18.4 |
| chSBT-004b | 8.0 | 5.5 | 9.2 | 11.0 |
| Isotype Control (Negative Control) | 0.2 | 0.5 | 0.2 | 0.6 |

Example 17

Chimeric Anti-TNFR2 Antibodies Bind to Subsets of Human Peripheral CD4$^+$ T Cells and CD8$^+$ T Cells This example shows that chimeric anti-TNFR2 antibodies bind to TNFR2 on human CD4$^+$ T cells and CD8$^+$ T cells. The chimeric antibodies were chSBT-003, chSBT-002, chSBT-004, and chSBT-004b. Flow cytometry was used to show that these chimeric anti-TNFR2 antibodies bound to human TNFR2 on a CD4$^+$ T cell population and a CD8$^+$ T cell population in human whole blood cells.

Figure 19:
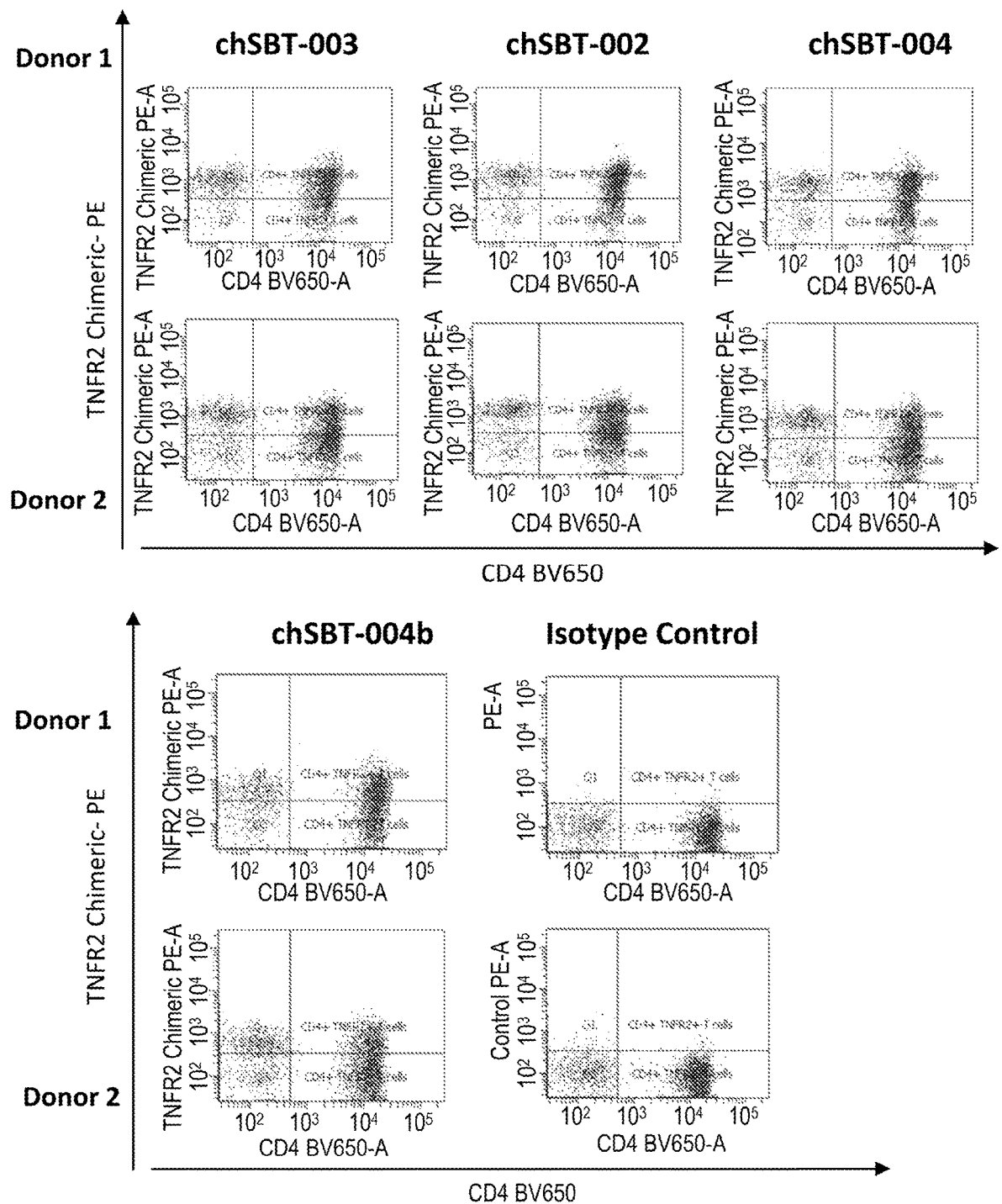
FIG. 19 shows chSBT-003, chSBT-002, chSBT-004, and chSBT-004b bound to a population of CD4$^+$ T cells. An antibody that targets a growth factor receptor expressed on epithelial cells, which was used as the isotype negative control, did not bind to a population of CD4$^+$ T cells.
Figure 20:
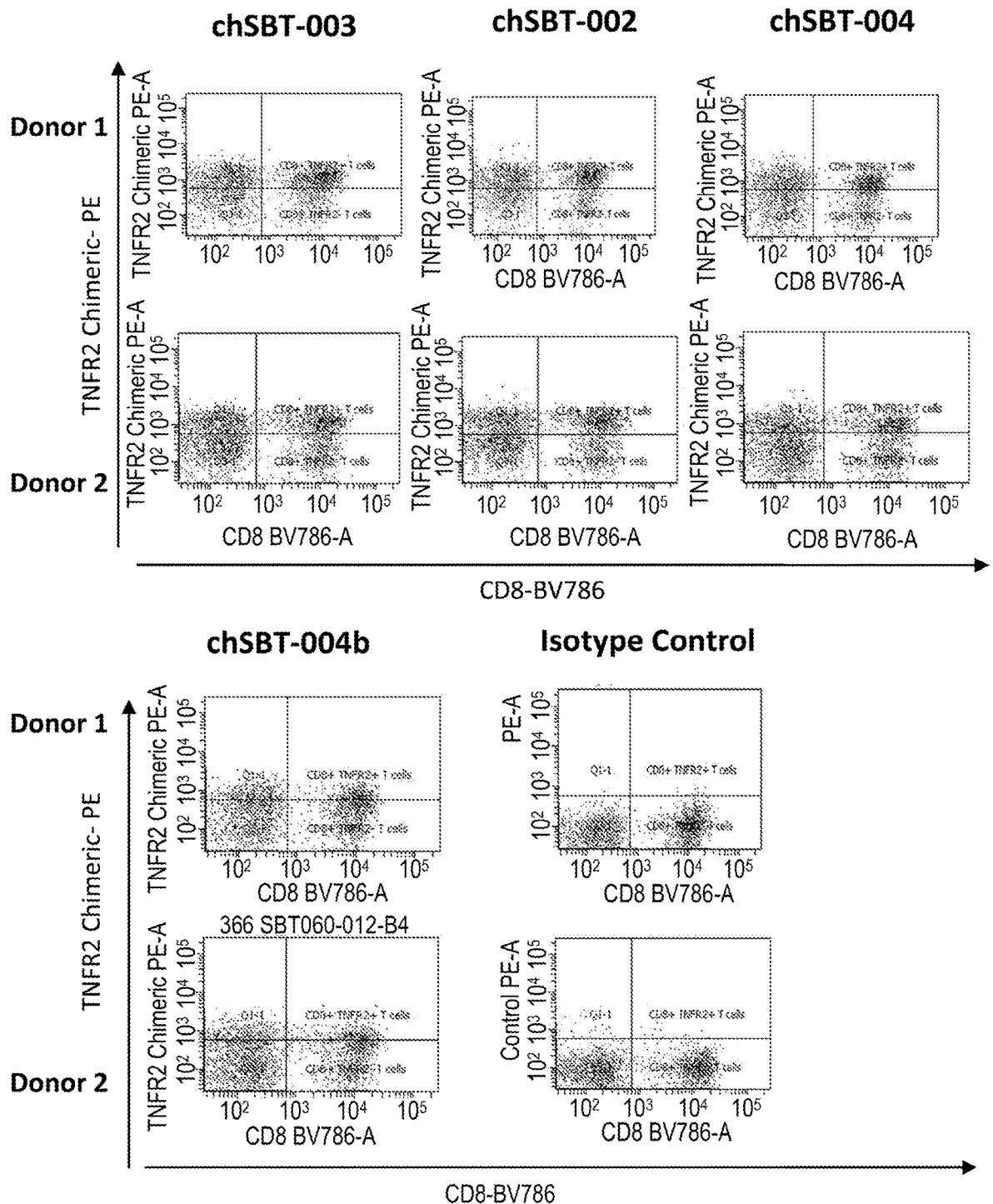
FIG. 20 shows chSBT-003, chSBT-002, chSBT-004, and chSBT-004b bound to a population of CD8$^+$ T cells. An antibody that targets a growth factor receptor expressed on epithelial cells, which was used as the isotype negative control, did not bind to a population of CD8$^+$ T cells.

Human peripheral blood mononuclear cells (PBMCs) from two independent donors were thawed and cultured overnight in RPM1 1640 (Lonza) with 10% heat inactivated FBS (Gibco). The following day 0.3×10$^6$ PBMC were counted and washed with PBS (Lonza). PBMCs were resuspended in Fixable Viability Stain 575V (BD) diluted 1:1,000 in PBS and incubated for 10 minutes. PBMCs were then washed twice in PBS to remove residual viability stain. PBMCs were then resuspended in Horizon Brilliant Stain Buffer (BD) with 10 uL per test of human Fc receptor binding inhibitor (eBioscience) and incubated on ice for 20 minutes to block Fc receptors. Fluorochrome-conjugated antibodies to CD3-BV510 clone SP34-2 (BD), CD4-BV650 clone L200 (BD) and CD8-BV786 clone RPA-T8 (BD) or isotype controls were added to PBMCs at a final dilution of 1:50 together with TNFR2 chimeric antibodies chSBT-003, chSBT-002, chSBT-004, SBT-004b, or isotype negative control, which was an antibody that targets a growth factor receptor expressed on epithelial cells, an anti-HER2 antibody with the same isotype as the chimeric antibodies, at 10 ug/mL. PBMCs were incubated 20 minutes on ice and then washed three times with 2% FBS PBS. To visualize TNFR chimeric antibody binding, PBMCs were resuspended in goat anti-human Fc-PE F(ab')$_2$ secondary reagent (Jackson ImmunoResearch) diluted 1:200 in 2% FBS PBS and incubated on ice for 20 minutes. Cells were then washed three times in 2% FBS PBS and resuspended in 200 uL 2% FBS PBS for flow cytometry analysis using a BD FACS Celesta instrument and FACS Diva software. T cells were analyzed for chimeric TNFR2 binding by gating on viable cells defined as lymphocytes using forward and side scatter and as T cells by anti-CD3 staining. CD4$^+$ and CD8$^+$ subsets were identified by commercially available specific antibody conjugates. FIG. 19 shows chSBT-003, chSBT-002, chSBT-004, and SBT-004b bound to a population of CD4$^+$ T cells. An antibody that targets a growth factor receptor expressed on epithelial cells, which was used as the isotype negative control, did not bind to a population of CD4$^+$ T cells. FIG. 20 shows chSBT-003, chSBT-002, chSBT-004, and SBT-004b bound to a population of CD8$^+$ T cells. An antibody that targets a growth factor receptor expressed on epithelial cells, which was used as the isotype negative control, did not bind to a population of CD8$^+$ T cells. TABLE 13 below is a summary of antibody binding to CD4$^+$ antibody$^+$ T cells and CD8$^+$ antibody$^+$ T cells.

TABLE 13

Percentage of CD4$^+$ antibody$^+$ (ab$^+$) cells

| Antibody | % CD4$^+$ ab$^+$ Donor 1 | % CD4$^+$ ab$^+$ Donor 2 | % CD8$^+$ ab$^+$ Donor 1 | % CD8$^+$ ab$^+$ Donor 2 |
|---|---|---|---|---|
| chSBT-003 | 44.4 | 35.0 | 23.8 | 17.7 |
| chSBT-002 | 47.6 | 38.3 | 24.3 | 18.9 |
| chSBT-004 | 38.4 | 26.4 | 18.8 | 16.1 |
| chSBT-004b | 29.3 | 18.4 | 9.1 | 11.4 |
| Isotype Control (Negative Control) | 0.7 | 0.7 | 0.5 | 0.7 |
| TNFR2-PE (Positive Control) | 14.9 | | 14.6 | |

Example 18

Humanization of Antibodies

This example shows one method for humanizing non-human antibodies. Four different anti-TNFR2 antibodies are humanized. These four antibodies are mouse SBT-001, mouse SBT-002, mouse SBT-003, and rat SBT-004. SBT-001 is comprised of the heavy chain variable region SEQ ID NO: 1 paired with the light chain variable region SEQ ID NO: 2. SBT-002 is comprised of the heavy chain variable region SEQ ID NO: 3 and the light chain variable region SEQ ID NO: 4. SBT-003 is comprised of the heavy chain variable region SEQ ID NO: 5 and the light chain variable region SEQ ID NO: 6. SBT-004 is comprised of the heavy chain variable region SEQ ID NO: 7 and the light chain variable region SEQ ID NO: 8 or the light chain variable region SEQ ID NO: 9.

These antibodies are humanized by inserting their CDRs into human germline framework sequences to reduce potential immunogenicity of the final therapeutic antibody. Two versions of each antibody are made, in which one version is made with CDRs according to Kabat, and the other version is made with CDRs according to the international ImMunoGeneTics information system (IMGT). For the humanized SBT-001 Kabat antibody (hkSBT-001), the CDRs from the heavy chain are SEQ ID NO: 10, SEQ ID NO: 11, and SEQ ID NO: 12 according to Kabat and the CDRs from the light chain were SEQ ID NO: 13, SEQ ID NO: 14, and SEQ ID NO: 15 according to Kabat. For the humanized SBT-001 IMGT antibody (hiSBT-001) the CDRs from the heavy chain are SEQ ID NO: 16, SEQ ID NO: 17, and SEQ ID NO: 18 according to IMGT and the CDRs from the light chain are SEQ ID NO: 19, SEQ ID NO: 20, and SEQ ID NO: 21 according to IMGT. For the humanized SBT-002 Kabat antibody (hkSBT-002), the CDRs from the heavy chain are SEQ ID NO: 22, SEQ ID NO: 23, and SEQ ID NO: 24 according to Kabat and the CDRs from the light chain were SEQ ID NO: 25, SEQ ID NO: 26, and SEQ ID NO: 27 according to Kabat. For the humanized SBT-002 IMGT antibody (hiSBT-002) the CDRs from the heavy chain are SEQ ID NO: 28, SEQ ID NO: 29, and SEQ ID NO: 30 according to IMGT, and the CDRs from the light chain are SEQ ID NO: 31, SEQ ID NO: 32, and SEQ ID NO: 33 according to IMGT. For the humanized SBT-003 Kabat antibody (hkSBT-003), the CDRs from the heavy chain are SEQ ID NO: 34, SEQ ID NO: 35, and SEQ ID NO: 36 according to Kabat and the CDRs from the light chain are SEQ ID NO: 37, SEQ ID NO: 38, and SEQ ID NO: 39 according to Kabat. For the humanized SBT-003 IMGT antibody (hiSBT-003), the CDRs from the heavy chain are SEQ ID NO: 40, SEQ ID NO: 41, and SEQ ID NO: 42 according to IMGT and the CDRs from the light chain are SEQ ID NO: 43, SEQ ID NO: 44, and SEQ ID NO: 45 according to IMGT. For the humanized SBT-004a Kabat antibody (hkSBT-004), the CDRs from the heavy chain are SEQ ID NO: 46, SEQ ID NO: 47, and SEQ ID NO: 48 according to Kabat and the CDRs from the light chain are SEQ ID NO: 49, SEQ ID NO: 50, or SEQ ID NO: 51 according to Kabat. For humanized SBT-004a IMGT antibody (hiSBT-004), the CDRs from the heavy chain are SEQ ID NO: 55, SEQ ID NO: 56, SEQ ID NO: 57 according to IMGT and the CDRs from the light chain are SEQ ID NO: 58, SEQ ID NO: 59, and SEQ ID NO: 60 according to IMGT. For the humanized SBT-004b Kabat antibody (hkSBT-004b), the CDRs from the heavy chain are SEQ ID NO: 46, SEQ ID NO: 47, and SEQ ID NO: 48 according to Kabat and the CDRs from the light chain are SEQ ID NO: 52, SEQ ID NO: 53, or SEQ ID NO: 54 according to Kabat. For humanized SBT-004b IMGT antibody (hiSBT-004b), the CDRs from the heavy chain are SEQ ID NO: 55, SEQ ID NO: 56, SEQ ID NO: 57 according to IMGT and the CDRs from the light chain are SEQ ID NO: 61, SEQ ID NO: 62, and SEQ ID NO: 63 according to IMGT.

To identify human germline genes for CDR grafting, alignments of the variable heavy and variable light regions are generated with human variable sequences from V BASE (MRC Centre for Protein Engineering), and single or multiple germline sequences are selected for CDR grafting based on high framework homology. A 3-D structural model for each antibody is generated to evaluate any differences between the human and non-human framework residues. Differing framework residues are assessed for their ability to influence antigen binding in the CDRs, and any differences deemed important are evaluated by inserting murine framework residues into the human framework sequences. The resulting humanized antibody sequences are evaluated for any potential major degradation or modification sites, and any isomerization (DG), deamidation (NG), oxidation (S), glycosylation (NXS/T), or free cysteines (C) were considered for mutation to decrease potential heterogeneity in the final antibody sequence.

Humanized $V_H$ and $V_L$ constructs are fused with human IgG1 Fc null and human Ck domains respectively. They are then cloned into the expression vector, pcDNA3.1(+) and transiently expressed in CHO-S cell line to generate humanized antibodies. The protein from the CHO-S supernatant is purified to homogeneity using protein A column on GE AKTA Pure™ system, and confirmed for purity using SEC. Each protein is then analyzed for binding to human and cynomolgus TNFR2 ECD using Octet Red 96 ™ instrument (ForteBio). $K_D$ values are obtained for each humanized antibody.

Example 19

Humanization of SBT-002

This example shows the humanization of SBT-002 to produce hSBT-002a, hSBT-002b, hSBT-002c, hSBT-002d, and hSBT-002e. SBT-002 was humanized by inserting the mouse CDRs into human germline framework sequences to reduce potential immunogenicity of the final therapeutic antibody. To identify human germline genes for CDR grafting, alignments of the variable heavy and variable light regions were generated with human variable sequences from V BASE (MRC Centre for Protein Engineering). VKI-O18, JK4 was chosen for grafting the variable light chain and VH2-70, JH6 was chosen for grafting the variable heavy chain based on high framework homology. A 3-D structural model was generated to evaluate any differences between the human and mouse framework residues. Differing framework residues were assessed for their potential ability to influence antigen binding in the CDRs, and any differences deemed important were evaluated by inserting mouse framework residues into the human framework sequences. Framework back mutations inserted into either the variable light or variable heavy sequence were prioritized based on their specific interaction with the CDR region and clustered together based on their proximity to each other in the 3D structural model. Framework back mutations I2V, K45R, Y49H, V58I, T69R, F71Y, T72S and R66Q, V79F, T81K, M82L, N82bS, M82cV, I95L were evaluated in the variable light chains and variable heavy chains, respectively. Humanized VH constructs were produced with SEQ ID NO: 64, SEQ ID NO: 66, or SEQ ID NO: 68. Humanized VL constructs were produced with SEQ ID NO: 65, SEQ ID NO: 67, or SEQ ID NO: 69. These humanized $V_H$ and $V_L$ constructs were fused with human IgG1 Fc null and human Ck domains, respectively. Each were then independently cloned into the expression vector, pcDNA3.1(+) and transiently expressed in CHO-S cell line to generate humanized antibodies. The humanized anti-TNFR2 antibody produced was SBT-002a (SEQ ID NO: 64 paired with SEQ ID NO: 65); SBT-002b (SEQ ID NO: 66 paired with SEQ ID NO: 67); SBT-002c (SEQ ID NO: 68 and SEQ ID NO: 67); SBT-002d (SEQ ID NO: 66 paired with SEQ ID NO: 69); or SBT-002e (SEQ ID NO: 68 paired with SEQ ID NO: 69).

The supernatant from each expression was collected on day 5 and analyzed for titer and binding affinity.

Example 20

Humanized Anti-TNFR2 Antibody Binds to Human TNFR2 Extracellular Domain

This example shows that humanized anti-TNFR2 antibody binds to human TNFR2 extracellular domain (ECD) The humanized anti-TNFR2 antibodies were hSBT-002a, hSBT-002b, hSBT-002c, hSBT-002d, and hSBT-002e as described in EXAMPLE 19, and a corresponding chimeric antibody, chSBT-002n, as described in EXAMPLE 13, was used as a positive control.

Analysis of binding to human TNFR2 ECD was performed using Octet Red 96 instrument (ForteBio). The Octet systems use propriety BLI to analyze biomolecular interaction. CHO supernatants of hSBT-002a, hSBT-002b, hSBT-002c, hSBT-002d, hSBT-002e, and chSBT-002n were diluted to 20 ug/ml based on titers with expression media and immobilized using anti-human Fc biosensors. These were incubated with 100 nM monomeric human TNFR2 in PBS. The experiments comprised of 5 steps: (1) baseline acquisition (60 s); (2) antibodies loading onto anti-human Fc biosensor (120 s); (3) second baseline acquisition (60 s); (4) association of interacting monomeric human TNFR2 ECD protein for $k_{on}$ measurement (120 s); (5) Dissociation of interacting monomeric human TNFR2 ECD for $k_{off}$ measurement (300 s). Data were analyzed using Octet Data Analysis Software 9.0 (ForteBio) and fitted to the 1:1 binding model. Equilibrium dissociation constants ($K_d$) were calculated by the ratio of $k_{on}$ to $k_{off}$. $K_d$ and $k_{off}$ values are shown in TABLE 14. hSBT-002a, hSBT-002b, hSBT-002c, hSBT-002d, and hSBT-002e had similar or slightly lower $K_d$ and similar or slightly slower $k_{off}$ than chSBT-002n.

TABLE 14

Antibody $K_d$ and $k_{off}$ for Human TNFR2 ECD

| Antibody | $K_d$ (M) | $k_{off}$ (1/s) |
|---|---|---|
| chSBT-002n | 1.92E-09 | 3.61E-04 |
| hSBT-002a | 4.89E-09 | 7.22E-04 |
| hSBT-002b | 2.44E-09 | 4.24E-04 |
| hSBT-002c | 2.27E-09 | 4.46E-04 |
| hSBT-002d | 1.73E-09 | 3.01E-04 |
| hSBT-002e | 1.54E-09 | 2.68E-04 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmacological composition comprising a humanized anti-TNFα Receptor 2 (anti-TNFR2) antibody that blocks TNFα binding to TNFR2, and a pharmaceutically acceptable carrier, wherein the anti-TNFR2 antibody comprises a set of three heavy chain complementary determining regions (HCDRs) and three light chain complementary determining regions (LCDRs), wherein the set of three HCDRs and three LCDRs are selected from the group consisting of:
   (a) SEQ ID NOs: 22-24 (HCDRs) and SEQ ID NOs: 25-27 (LCDRs); and
   (b) SEQ ID NOs: 28-30 (HCDRs) and SEQ ID NOs: 31-33 (LCDRs).

2. The pharmacological composition of claim 1, wherein said anti-TNFR2 antibody comprises a variable region heavy chain ($V_H$) comprising three heavy chain complementary determining regions (HCDRs) and a variable region light chain ($V_L$) comprising three light chain complementary determining regions (LCDRs), wherein the $V_H$ comprises an amino acid sequence having at least 90% sequence identity to the amino acid sequence of SEQ ID NO: 66 or 68, and the three HCDRs have the amino acid sequences of SEQ ID NOs: 22-24 or SEQ ID NOs: 28-30; and the $V_L$ comprises an amino acid sequence having at least 90% sequence identity to the amino acid sequence of SEQ ID NO: 67 or 69, and the three LCDRs have the amino acid sequences of SEQ ID NOs: 25-27 or SEQ ID NOs: 31-33.

3. The pharmacological composition of claim 1, wherein said anti-TNFR2 antibody comprises a human IgG1 Fc domain.

4. The pharmacological composition of claim 3, wherein said human IgG1 Fc domain is null for binding to an Fcγ receptor.

5. The pharmacological composition of claim 2, wherein said anti-TNFR2 antibody comprises a variable region heavy chain ($V_H$) and a variable region light chain ($V_L$), wherein the $V_H$ comprises the amino acid sequence set forth in SEQ ID NO:66 and the $V_L$ comprises the amino acid sequence set forth in SEQ ID NO:67; the $V_H$ comprises the amino acid sequence set forth in SEQ ID NO:68 and the $V_L$ comprises the amino acid sequence set forth in SEQ ID NO:67; the $V_H$ comprises the amino acid sequence set forth in SEQ ID NO:66 and the $V_L$ comprises the amino acid sequence set forth in SEQ ID NO:69; or the $V_H$ comprises the amino acid sequence set forth in SEQ ID NO:68 and the $V_L$ comprises the amino acid sequence set forth in SEQ ID NO:69.

6. The pharmacological composition of claim 2, wherein the $V_H$ comprises an amino acid sequence having at least 95% sequence identity to the amino acid sequence of SEQ ID NO: 66 or 68.

7. The pharmacological composition of claim 2, wherein the $V_H$ comprises an amino acid sequence having at least 98% sequence identity to the amino acid sequence of SEQ ID NO: 66 or 68.

8. The pharmacological composition of claim 2, wherein the $V_L$ comprises an amino acid sequence having at least 95% sequence identity to the amino acid sequence of SEQ ID NO: 67 or 69.

9. The pharmacological composition of claim 2, wherein the $V_L$ comprises an amino acid sequence having at least 98% sequence identity to the amino acid sequence of SEQ ID NO: 67 or 69.

10. A humanized anti-TNFR2 antibody that blocks TNFα binding to TNFR2 and has a dissociation constant (Kd) for TNFR2 extracellular domain (ECD) ranging from 5 nM to 1.5 nM, wherein the anti-TNFR2 antibody comprises a set of three heavy chain complementary determining regions (HCDRs) and three light chain complementary determining regions (LCDRs), wherein the set of three HCDRs and three LCDRs are selected from the group consisting of:
  (a) SEQ ID NOs: 22-24 (HCDRs) and SEQ ID NOs: 25-27 (LCDRs); and
  (b) SEQ ID NOs: 28-30 (HCDRs) and SEQ ID NOs: 31-33 (LCDRs).

11. The humanized anti-TNFR2 antibody of claim 10, wherein said anti-TNFR2 antibody comprises a variable region heavy chain ($V_H$) comprising three heavy chain complementary determining regions (HCDRs) and a variable region light chain ($V_L$) comprising three light chain complementary determining regions (LCDRs), wherein the $V_H$ comprises an amino acid sequence having at least 90% sequence identity to the amino acid sequence of SEQ ID NO: 66 or 68, and the three HCDRs have the amino acid sequences of SEQ ID NOs: 22-24 or SEQ ID NOs: 28-30; and the $V_L$ comprises the amino acid sequence of at least 90% sequence identity to the amino acid sequence of SEQ ID NO: 67 or 69, and the three LCDRs have the amino acid sequences of SEQ ID NOs: 25-27 or SEQ ID NOs: 31-33.

12. The humanized anti-TNFR2 antibody of claim 11, wherein said anti-TNFR2 antibody comprises a variable region heavy chain ($V_H$) and a variable region light chain ($V_L$), wherein the $V_H$ comprises the amino acid sequence set forth in SEQ ID NO:66 and the $V_L$ comprises the amino acid sequence set forth in SEQ ID NO:67; the $V_H$ comprises the amino acid sequence set forth in SEQ ID NO:68 and the $V_L$ comprises the amino acid sequence set forth in SEQ ID NO:67; the $V_H$ comprises the amino acid sequence set forth in SEQ ID NO:66 and the $V_L$ comprises the amino acid sequence set forth in SEQ ID NO:69; or the $V_H$ comprises the amino acid sequence set forth in SEQ ID NO:68 and the $V_L$ comprises the amino acid sequence set forth in SEQ ID NO:69.

13. The humanized anti-TNFR2 antibody of claim 11, wherein the $V_H$ comprises an amino acid sequence having at least 95% sequence identity to the amino acid sequence of SEQ ID NO: 66 or 68.

14. The humanized anti-TNFR2 antibody of claim 11, wherein the $V_H$ comprises an amino acid sequence having at least 98% sequence identity to the amino acid sequence of SEQ ID NO: 66 or 68.

15. The humanized anti-TNFR2 antibody of claim 11, wherein the $V_L$ comprises an amino acid sequence having at least 95% sequence identity to the amino acid sequence of SEQ ID NO: 67 or 69.

16. The humanized anti-TNFR2 antibody of claim 11, wherein the $V_L$ comprises an amino acid sequence having at least 98% sequence identity to the amino acid sequence of SEQ ID NO: 67 or 69.

17. A method of eliciting an immune response against a tumor in a patient, comprising administering to the patient a pharmaceutical composition of claim 1.

* * * * *

SEQUENCE LISTING

```
<160> NUMBER OF SEQ ID NOS: 69

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Asp Ile Asn Pro Asn Tyr Glu Ser Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Val Arg Ser Leu Thr Ser Glu Asp Thr Ala Val Phe Tyr Cys
                85                  90                  95

Ala Arg Asp Lys Gly Trp Tyr Phe Asp Val Trp Gly Ala Gly Thr Thr
            100                 105                 110

Val Thr Val Ser Ser
        115

<210> SEQ ID NO 2
```

<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Val Lys Asn Met
            20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Leu Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Lys Phe Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Leu Thr Ser Val Val Thr Ala Asp Thr Ala Thr Tyr Tyr
                85                  90                  95

Cys Ala Arg Leu Thr Gly Thr Arg Tyr Phe Asp Tyr Trp Gly Gln Gly
            100                 105                 110

Thr Thr Leu Thr Val Ser Ser
        115

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Val Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Lys Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Gly Asn Leu Trp Thr
                85                  90                  95

Phe Gly Gly Gly Thr Lys Leu Glu Ile Thr
            100                 105

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
 50                  55                  60

Lys Gly Arg Phe Ala Phe Ser Ser Glu Thr Ser Thr Ser Thr Ala Tyr
 65                  70                  75                  80

Leu Gln Ile Asn Asn Leu Lys Asn Asp Asp Thr Thr Thr Tyr Phe Cys
                85                  90                  95

Ala Thr Tyr Tyr Gly Ser Ser Tyr Val Pro Asp Tyr Trp Gly Gln Gly
            100                 105                 110

Thr Ser Leu Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser His Lys Phe Met Ser Thr Ser Val Gly
 1               5                  10                  15

Asp Arg Val Ser Ile Thr Cys Lys Ala Ser Gln Asn Val Gly Thr Ala
                20                  25                  30

Val Ala Trp Tyr Gln His Lys Pro Gly Gln Ser Pro Lys Leu Leu Ile
            35                  40                  45

Tyr Trp Thr Ser Ser Arg His Thr Gly Val Pro Asp Arg Phe Thr Gly
 50                  55                  60

Ser Gly Ser Gly Thr Glu Phe Thr Leu Thr Ile Ser Asn Val Gln Ser
 65                  70                  75                  80

Glu Asp Leu Ala Asp Tyr Phe Cys His Gln Tyr Ser Asp Tyr Pro Tyr
                85                  90                  95

Thr Phe Gly Gly Gly Thr Lys Leu Glu Ile Lys
        100                 105

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Gln Ser Gly Pro Glu Val Arg Pro Gly Ser
1               5                   10                  15

Ser Val Lys Ile Ser Cys Lys Ala Ser Gly Tyr Thr Phe Thr Asp Tyr
                20                  25                  30

Ile Met His Trp Val Lys Gln Ser Pro Gly Gln Gly Leu Glu Trp Ile
            35                  40                  45

Gly Trp Val Asp Pro Glu Tyr Gly Ser Thr Tyr Ala Glu Lys Phe
    50                  55                  60

Lys Lys Lys Ala Thr Leu Thr Ala Asp Thr Ser Ser Asn Thr Ala Tyr
65                  70                  75                  80

Ile Gln Leu Ser Ser Leu Thr Ser Glu Asp Thr Ala Thr Tyr Phe Cys
                85                  90                  95

Ala Arg Asp Asp Gly Ser Tyr Ser Pro Phe Asp Tyr Trp Gly Gln Gly
            100                 105                 110

Val Met Val Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile Asn Lys Tyr
                20                  25                  30

Ile Ala Trp Tyr Gln Gln Lys Pro Gly Lys Ala Pro Arg Leu Leu Ile
            35                  40                  45

Arg Tyr Thr Ser Thr Leu Glu Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Val Asn Leu Leu Thr
                85                  90                  95

Phe Gly Ala Gly Thr Lys Leu Glu Ile Lys
            100                 105

<210> SEQ ID NO 9
<211> LENGTH: 107
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 9

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 10

Asp Tyr Asn Met Asp
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 11

Asp Ile Asn Pro Asn Tyr Glu Ser Thr Ser Tyr Asn Gln Lys Phe Lys
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 12

Asp Lys Gly Trp Tyr Phe Asp Val
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 13

Arg Ala Ser Ser Ser Val Lys Asn Met Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ser Asn Leu Ala Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Phe Thr Ser Ser Pro Tyr Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Thr Phe Thr Asp Tyr Asn
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Asn Pro Asn Tyr Glu Ser Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Asp Lys Gly Trp Tyr Phe Asp Val
1               5

<210> SEQ ID NO 19
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 19

Ser Ser Val Lys Asn
1               5

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Thr Ser
1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Phe Thr Ser Ser Pro Tyr Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Ser Gly Met Gly Val Gly
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Ile Trp Trp Asp Asp Asp Lys Phe Tyr Asn Pro Ser Leu Lys Ser
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Gly Thr Arg Tyr Phe Asp Tyr
1               5
```

```
<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ala Ser Gln Asp Ile Asn Lys Phe Ile Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Thr Ser Thr Leu Gln Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Tyr Gly Asn Leu Trp Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Phe Ser Leu Ser Thr Ser Gly Met Gly
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Ile Trp Trp Asp Asp Asp Lys
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Ala Arg Leu Thr Gly Thr Arg Tyr Phe Asp Tyr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Asp Ile Asn Lys Phe Ile
1               5

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Thr Ser
1

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Gln Tyr Gly Asn Leu Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Tyr Ser Met His
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Asn Thr Glu Thr Gly Glu Pro Thr Tyr Ala Asp Asp Phe Lys
1               5                   10                  15

Gly

<210> SEQ ID NO 36
<211> LENGTH: 10

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Tyr Gly Ser Ser Tyr Val Pro Asp Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ala Ser Gln Asn Val Gly Thr Ala Val Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Thr Ser Ser Arg His Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Gln Tyr Ser Asp Tyr Pro Tyr Thr Phe
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Thr Phe Thr Asp Tyr Ser
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Asn Thr Glu Thr Gly Glu Pro

```
1               5
```

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Ala Thr Tyr Tyr Gly Ser Ser Tyr Val Pro Asp Tyr
1               5                   10
```

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gln Asn Val Gly Thr Ala
1               5
```

<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Trp Thr Ser
1
```

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gln Tyr Ser Asp Tyr Pro Tyr Thr
1               5
```

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Asp Tyr Ile Met His
1               5
```

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Trp Val Asp Pro Glu Tyr Gly Ser Thr Asp Tyr Ala Glu Lys Phe Lys
1               5                   10                  15

Lys Lys

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Gly Ser Tyr Ser Pro Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ala Ser Gln Asn Ile Asn Lys Tyr Ile Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Thr Ser Thr Leu Glu Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Gln Tyr Val Asn Leu Leu Thr
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Ala Ser Glu Asn Val Val Thr Tyr Val Ser
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ala Ser Asn Arg Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gln Gly Tyr Ser Tyr Pro Tyr Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Tyr Thr Phe Thr Asp Tyr
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Val Asp Pro Glu Tyr Gly Ser
1               5

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Asp Asp Gly Ser Tyr Ser Pro Phe Asp Tyr
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 58

Gln Asn Ile Asn Lys Tyr
1               5

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Thr Ser
1

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Gln Tyr Val Asn Leu Leu Thr
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Asn Val Val Thr Tyr
1               5

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ala Ser
1

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gln Gly Tyr Ser Tyr Pro Tyr Thr
1               5

<210> SEQ ID NO 64
<211> LENGTH: 119
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 64

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Phe Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Thr Gly Thr Arg Tyr Phe Asp Tyr Trp Gly Gln Gly
            100                 105                 110

Thr Thr Val Thr Val Ser Ser
            115

<210> SEQ ID NO 65
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Phe
            20                  25                  30

Ile Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Gly Asn Leu Trp Thr
                85                  90                  95

Phe Gly Gly Gly Thr Lys Val Glu Ile Lys
            100                 105

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30
```

Gly Met Gly Val Gly Trp Ile Arg Gln Pro Pro Gly Lys Ala Leu Glu
            35                  40                  45

Trp Leu Ala His Ile Trp Trp Asp Asp Asp Lys Phe Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Thr Gly Thr Arg Tyr Phe Asp Tyr Trp Gly Gln Gly
            100                 105                 110

Thr Thr Val Thr Val Ser Ser
            115

<210> SEQ ID NO 67
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Val Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Phe
            20                  25                  30

Ile Ala Trp Tyr Gln Gly Lys Pro Gly Lys Ala Pro Lys Leu Leu Ile
            35                  40                  45

His Tyr Thr Ser Thr Leu Gln Pro Gly Ile Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Gly Asn Leu Trp Thr
                85                  90                  95

Phe Gly Gly Gly Thr Lys Val Glu Ile Lys
            100                 105

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Asp Lys Phe Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

-continued

```
Cys Ala Arg Leu Thr Gly Thr Arg Tyr Phe Asp Tyr Trp Gly Gln Gly
            100                 105                 110
Thr Thr Val Thr Val Ser Ser
        115

<210> SEQ ID NO 69
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Val Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Phe
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Gly Asn Leu Trp Thr
                85                  90                  95

Phe Gly Gly Gly Thr Lys Val Glu Ile Lys
            100                 105
```